(12) United States Patent
Husnu et al.

(10) Patent No.: US 9,139,316 B2
(45) Date of Patent: Sep. 22, 2015

(54) CLOSED VIAL FILL SYSTEM FOR ASEPTIC DISPENSING

(75) Inventors: Mehmet Husnu, Phoenix, AZ (US); Dennis Eshima, Phoenix, AZ (US); Derrick Alcaide, Los Angeles, CA (US); Scott N. Danhof, Plain City, OH (US); Jim Gleeson, Columbus, OH (US); Eric Hassenpflug, Westerville, OH (US); Jim Prescott, Columbus, OH (US)

(73) Assignee: Cardinal Health 414, LLC, Dublin, OH (US)

( * ) Notice: Subject to any disclaimer, the term of this patent is extended or adjusted under 35 U.S.C. 154(b) by 498 days.

(21) Appl. No.: 13/339,226

(22) Filed: Dec. 28, 2011

(65) Prior Publication Data
US 2012/0222774 A1 Sep. 6, 2012

Related U.S. Application Data

(60) Provisional application No. 61/428,041, filed on Dec. 29, 2010, provisional application No. 61/508,409, filed on Jul. 15, 2011.

(51) Int. Cl.
*B65B 1/04* (2006.01)
*B65B 37/06* (2006.01)
*B65B 3/00* (2006.01)

(52) U.S. Cl.
CPC ............... *B65B 37/06* (2013.01); *B65B 3/003* (2013.01)

(58) Field of Classification Search
CPC ................................ B65B 37/06; B65B 3/003
USPC .................... 141/234–238, 244; 604/131, 151
See application file for complete search history.

(56) References Cited

U.S. PATENT DOCUMENTS 3,959,172 A 5/1976 Brownell et al.
4,754,786 A * 7/1988 Roberts .............................. 141/1
4,794,178 A 12/1988 Coenen et al.
(Continued)

FOREIGN PATENT DOCUMENTS

EP 2059443 B1 5/2009
WO WO 95/12203 A1 5/1995
(Continued)

OTHER PUBLICATIONS

International Search Report dated May 1, 2012, PCT Application No. PCT/US11/67650, 13 pages.
(Continued)

*Primary Examiner* — Timothy L Maust

(57) ABSTRACT

A closed path vial fill system includes a bulk product vial, a peristaltic pump operated by a stepper motor, a dispensing manifold assembly to which may be coupled at least one final product vial, an optional quality check station, and an optional waste collection system. A concentration, activity, and volume (CAV) sensor may be incorporated into the system to receive a radiopharmaceutical product directly from a synthesizing unit. A control system may be integrated into the system to provide automated control of various aspects of the radiopharmaceutical dispensing process. The system is used to aseptically dispense finished radiopharmaceuticals into receiving vessels, such as a Quality Control vial, a sterility vial, and/or final product vials, while providing users an efficient means for removing and discarding contaminated disposable components.

49 Claims, 61 Drawing Sheets

(56) References Cited

U.S. PATENT DOCUMENTS

| | | | |
|---|---|---|---|
| 4,967,811 | A | 11/1990 | DiGianfilippo et al. |
| 5,029,479 | A | 7/1991 | Bryan |
| 5,139,731 | A | 8/1992 | Hendry |
| 5,171,132 | A | 12/1992 | Miyazaki et al. |
| 5,211,678 | A | 5/1993 | Stephenson et al. |
| 5,356,378 | A | 10/1994 | Doan |
| 5,373,844 | A | 12/1994 | Smith et al. |
| 5,428,470 | A | 6/1995 | Labriola, II |
| 5,429,133 | A | 7/1995 | Thurston et al. |
| 5,519,635 | A | 5/1996 | Miyake et al. |
| 5,527,473 | A | 6/1996 | Ackerman |
| 5,540,081 | A | 7/1996 | Takeda et al. |
| 5,580,523 | A | 12/1996 | Bard |
| 5,605,251 | A | 2/1997 | Retti |
| 5,626,172 | A * | 5/1997 | Schumacher et al. ........ 141/236 |
| 5,648,268 | A | 7/1997 | Batchelder et al. |
| 5,659,171 | A | 8/1997 | Young et al. |
| 5,800,784 | A | 9/1998 | Horn |
| 5,866,907 | A | 2/1999 | Drukier et al. |
| 5,911,252 | A | 6/1999 | Cassel |
| 5,932,178 | A | 8/1999 | Yamazaki et al. |
| 5,937,364 | A | 8/1999 | Westgard et al. |
| 6,021,341 | A | 2/2000 | Scibilia et al. |
| 6,135,955 | A | 10/2000 | Madden et al. |
| 6,172,207 | B1 | 1/2001 | Damhaut et al. |
| 6,227,809 | B1 | 5/2001 | Forster et al. |
| 6,359,952 | B1 | 3/2002 | Alvord |
| 6,531,705 | B2 | 3/2003 | White et al. |
| 6,559,440 | B2 | 5/2003 | Yarnall et al. |
| 6,565,815 | B1 | 5/2003 | Chang et al. |
| 6,567,492 | B2 | 5/2003 | Kiselev et al. |
| 6,599,484 | B1 | 7/2003 | Zigler et al. |
| 6,643,538 | B1 | 11/2003 | Majewski et al. |
| 6,644,944 | B2 | 11/2003 | Karp |
| 6,658,946 | B2 | 12/2003 | Lipscomb et al. |
| 6,771,802 | B1 | 8/2004 | Patt et al. |
| 6,787,786 | B2 | 9/2004 | Kalas et al. |
| 6,827,095 | B2 | 12/2004 | O'Connor et al. |
| 6,828,143 | B1 | 12/2004 | Bard |
| 6,845,137 | B2 | 1/2005 | Ruth et al. |
| 6,915,823 | B2 * | 7/2005 | Osborne et al. ................. 141/27 |
| 6,917,044 | B2 | 7/2005 | Amini |
| 6,986,649 | B2 | 1/2006 | Dai et al. |
| 6,991,214 | B2 | 1/2006 | Richter |
| 7,018,614 | B2 | 3/2006 | Kiselev et al. |
| 7,025,323 | B2 | 4/2006 | Krulevitch et al. |
| 7,030,399 | B2 | 4/2006 | Williamson et al. |
| 7,056,477 | B1 | 6/2006 | Schwalbe et al. |
| 7,104,768 | B2 | 9/2006 | Richter et al. |
| 7,118,917 | B2 | 10/2006 | Bergh et al. |
| 7,127,023 | B2 | 10/2006 | Wieland |
| 7,170,072 | B2 | 1/2007 | Schwarz et al. |
| 7,172,735 | B1 | 2/2007 | Lowe et al. |
| 7,200,198 | B2 | 4/2007 | Wieland et al. |
| 7,206,715 | B2 | 4/2007 | Vanderveen et al. |
| 7,235,216 | B2 | 6/2007 | Kiselev et al. |
| 7,279,676 | B2 | 10/2007 | Twomey |
| 7,347,617 | B2 | 3/2008 | Pugia et al. |
| 7,378,659 | B2 | 5/2008 | Burr et al. |
| 7,418,981 | B2 * | 9/2008 | Baker et al. ........................ 141/9 |
| 7,419,653 | B2 | 9/2008 | Walsh et al. |
| 7,435,392 | B2 | 10/2008 | Oberbeck et al. |
| 7,445,650 | B2 | 11/2008 | Weil et al. |
| 7,445,926 | B2 | 11/2008 | Mathies et al. |
| 7,468,165 | B2 | 12/2008 | Oberbeck et al. |
| 7,476,883 | B2 | 1/2009 | Nutt |
| 7,485,454 | B1 | 2/2009 | Jury et al. |
| 7,512,206 | B2 | 3/2009 | Wieland |
| 7,577,228 | B2 | 8/2009 | Jackson |
| 7,586,102 | B2 | 9/2009 | Mourtada et al. |
| 7,607,641 | B1 | 10/2009 | Yuan |
| 7,622,509 | B2 | 11/2009 | Tonkovich et al. |
| 7,624,642 | B2 | 12/2009 | Romo |
| 7,634,378 | B2 | 12/2009 | Kaplit |
| 7,638,059 | B2 | 12/2009 | Kim et al. |
| 7,641,860 | B2 | 1/2010 | Matteo |
| 7,659,522 | B2 | 2/2010 | Kim et al. |
| 7,766,883 | B2 | 8/2010 | Rellly et al. |
| 7,829,032 | B2 | 11/2010 | Van Dam et al. |
| 7,832,429 | B2 | 11/2010 | Young et al. |
| 7,863,035 | B2 | 1/2011 | Clemens et al. |
| 7,917,313 | B2 | 3/2011 | Ziegler et al. |
| 7,987,726 | B2 | 8/2011 | Dannhauer |
| 2001/0055812 | A1 | 12/2001 | Mian et al. |
| 2002/0043638 | A1 | 4/2002 | Kao et al. |
| 2002/0048536 | A1 | 4/2002 | Bergh et al. |
| 2002/0128734 | A1 | 9/2002 | Dorsett |
| 2002/0148957 | A1 | 10/2002 | Lingren et al. |
| 2003/0007588 | A1 | 1/2003 | Kiselev et al. |
| 2003/0034456 | A1 | 2/2003 | McGregor |
| 2003/0057381 | A1 | 3/2003 | Hirayanagi |
| 2003/0057391 | A1 | 3/2003 | Krulevitch et al. |
| 2003/0175947 | A1 | 9/2003 | Liu et al. |
| 2003/0194039 | A1 | 10/2003 | Kiselev et al. |
| 2004/0022696 | A1 | 2/2004 | Zigler et al. |
| 2004/0028573 | A1 | 2/2004 | Schmitz et al. |
| 2004/0037739 | A1 | 2/2004 | McNeely et al. |
| 2004/0054248 | A1 | 3/2004 | Kimchy et al. |
| 2004/0084340 | A1 | 5/2004 | Morelle et al. |
| 2004/0120836 | A1 | 6/2004 | Dai et al. |
| 2004/0136878 | A1 | 7/2004 | Meier et al. |
| 2004/0209354 | A1 | 10/2004 | Mathies et al. |
| 2004/0258615 | A1 | 12/2004 | Buchanan et al. |
| 2004/0262158 | A1 | 12/2004 | Alvord et al. |
| 2005/0072946 | A1 | 4/2005 | Studer et al. |
| 2005/0084055 | A1 | 4/2005 | Alvord et al. |
| 2005/0191184 | A1 | 9/2005 | Vinson |
| 2005/0232387 | A1 | 10/2005 | Padgett et al. |
| 2005/0232861 | A1 | 10/2005 | Buchanan et al. |
| 2005/0260130 | A1 | 11/2005 | Elmaleh et al. |
| 2006/0004491 | A1 | 1/2006 | Welch et al. |
| 2006/0076068 | A1 | 4/2006 | Young et al. |
| 2006/0132068 | A1 | 6/2006 | Norling et al. |
| 2006/0150385 | A1 | 7/2006 | Gilligan et al. |
| 2006/0231519 | A1 | 10/2006 | Py et al. |
| 2006/0263293 | A1 | 11/2006 | Kolb et al. |
| 2007/0027637 | A1 | 2/2007 | Delenstarr et al. |
| 2007/0048217 | A1 | 3/2007 | McBride et al. |
| 2007/0217561 | A1 | 9/2007 | Wieland et al. |
| 2007/0217963 | A1 | 9/2007 | Elizarov et al. |
| 2008/0050283 | A1 | 2/2008 | Chou et al. |
| 2008/0064110 | A1 | 3/2008 | Elizarov et al. |
| 2008/0122390 | A1 | 5/2008 | Lidestri |
| 2008/0123808 | A1 | 5/2008 | Caffrey |
| 2008/0171999 | A1 | 7/2008 | Baplue et al. |
| 2008/0172024 | A1 | 7/2008 | Yow |
| 2008/0177126 | A1 | 7/2008 | Tate et al. |
| 2008/0181829 | A1 | 7/2008 | Matteo |
| 2008/0233018 | A1 | 9/2008 | Van Dam et al. |
| 2008/0233653 | A1 | 9/2008 | Hess et al. |
| 2008/0249510 | A1 | 10/2008 | Mescher et al. |
| 2008/0277591 | A1 | 11/2008 | Shahar et al. |
| 2008/0281090 | A1 | 11/2008 | Lee et al. |
| 2009/0005617 | A1 | 1/2009 | Maeding et al. |
| 2009/0036668 | A1 | 2/2009 | Elizarov et al. |
| 2009/0056822 | A1 | 3/2009 | Young et al. |
| 2009/0056861 | A1 | 3/2009 | Young et al. |
| 2009/0094940 | A1 | 4/2009 | Py |
| 2009/0095635 | A1 | 4/2009 | Elizarov et al. |
| 2009/0139310 | A1 | 6/2009 | Santiago et al. |
| 2009/0157040 | A1 | 6/2009 | Jacobson et al. |
| 2009/0159807 | A1 | 6/2009 | Waller |
| 2009/0165477 | A1 | 7/2009 | Sturken et al. |
| 2009/0181411 | A1 | 7/2009 | Battrell et al. |
| 2009/0185955 | A1 | 7/2009 | Nellissen |
| 2009/0218520 | A1 | 9/2009 | Nutt |
| 2009/0247417 | A1 | 10/2009 | Haas et al. |
| 2009/0288497 | A1 | 11/2009 | Ziegler et al. |
| 2009/0305431 | A1 | 12/2009 | Hodges et al. |
| 2009/0314365 | A1 | 12/2009 | McAvoy et al. |
| 2009/0314972 | A1 | 12/2009 | McAvoy et al. |
| 2010/0008834 | A1 | 1/2010 | Lohf et al. |
| 2010/0101783 | A1 | 4/2010 | Vinegar et al. |
| 2010/0145630 | A1 | 6/2010 | Ball et al. |

(56) References Cited

U.S. PATENT DOCUMENTS

| | | |
|---|---|---|
| 2010/0187452 A1 | 7/2010 | Mukaddam et al. |
| 2010/0217011 A1 | 8/2010 | Dinkelborg et al. |
| 2010/0243972 A1 | 9/2010 | Voccia et al. |
| 2010/0286512 A1 | 11/2010 | Dhawale et al. |
| 2010/0304494 A1 | 12/2010 | Tokhtuev et al. |
| 2010/0307616 A1 | 12/2010 | Liou et al. |
| 2011/0003981 A1 | 1/2011 | Hirano et al. |
| 2011/0008215 A1 | 1/2011 | Elizarov et al. |
| 2011/0041935 A1 | 2/2011 | Zhou et al. |
| 2011/0087439 A1 | 4/2011 | Ziegler et al. |
| 2011/0098465 A1 | 4/2011 | Ball et al. |
| 2011/0126911 A1 | 6/2011 | Kobrin et al. |
| 2011/0150714 A1 | 6/2011 | Elizarov et al. |
| 2011/0178359 A1 | 7/2011 | Hirschman et al. |
| 2012/0074330 A1 | 3/2012 | Bouton et al. |
| 2012/0222774 A1* | 9/2012 | Husnu et al. .................. 141/69 |

FOREIGN PATENT DOCUMENTS

| | | |
|---|---|---|
| WO | WO 00/62919 A1 | 10/2000 |
| WO | WO 02/33296 A2 | 4/2002 |
| WO | WO 02/083210 A1 | 10/2002 |
| WO | WO 2005/025519 A2 | 3/2005 |
| WO | WO 2007/041486 A2 | 4/2007 |
| WO | WO 2008/028260 A2 | 3/2008 |
| WO | WO 2008/083313 A2 | 7/2008 |
| WO | WO 2008/101305 A1 | 8/2008 |
| WO | WO 2008/128306 A1 | 10/2008 |
| WO | WO 2009/003251 A1 | 1/2009 |
| WO | WO 2010/072342 A2 | 7/2010 |

OTHER PUBLICATIONS

Blaine R. Copenheaver, International Search Report & Written Opinion issued in Application No. PCT/US12/46910, mailed Sep. 28, 2012, 10 pages.

Lee W. Young, International Search Report & Written Opinion issued in Application No. PCT/US12/46943, mailed Sep. 28, 2012, 8 pages.

Lee W. Young, International Search Report & Written Opinion issued in Application No. PCT/US12/46968, mailed Oct. 2, 2012, 15 pages.

Lee W. Young, International Search Report & Written Opinion issued in Application No. PCT/US12/46955, mailed Dec. 7, 2012, 12 pages.

Blaine R. Copenheaver, International Search Report & Written Opinion issued in Application No. PCT/US12/54229, mailed Dec. 31, 2012, 12 pages.

Lee W. Young, International Search Report & Written Opinion issued in Application No. PCT/US12/46933, mailed Feb. 11, 2013, 13 pages.

Pacak et al. "Synthesis of 2-Deoxy-2-fluoro-D-glucose." Journal of the Chemical Society D: Chemical Communications, 1969, issue 2, p. 77.

Ido et al. "Labeled 2-deoxy-D-glucose analogs, 18F-labeled 2-deoxy-2-fluoro-D-glucose, 2-deoxy-2-fluoro-D-mannose and 14C-2-deoxy-2-fluoro-D-glucose." Journal of Labelled Compounds and Radiopharmaceuticals, 1978, vol. 14, issue 2, pp. 175-183.

Muehllehner. "Effect of Crystal Thickness on Scintillation Camera Performance." Journal of Nuclear Medicine, 1979, vol. 20, issue 9, pp. 992-994.

Gomzina et al. "Optimization of Automated Synthesis of 2-[18F] Fluoro-2-deoxy-D-glucose Involving Base Hydrolysis." Radiochemistry, 2002, vol. 44, issue 4, pp. 403-409.

GE Medical Systems Benelux s.a., "TRACERlab MX FDG," Operator manual, Technical Publications, Direction 2335255-100, Version I, Last updated: Mar. 2003, pp. 1-61.

Project Fact Sheet. Lab-on-a-chip implementation of production processes for new molecular Imaging agents. Universite De Liege. Http://cordis.europa.eu/fetch?CALLER=FP6_PROJ&ACTION=D &RCN=75854&DOC=. Last updated on Dec. 8, 2009, accessed on May 12, 2010, 2 pages.

Peng et al. "Design study of a high-resolution breast-dedicated Pet system built from cadmium zinc telluride detectors." Physics in Medicine and Biology, 2010, vol. 55, issue 9, pp. 2761-2788.

Bubble col. reactor. Wikipedia, last modified on Oct. 26 2010, accessed on May 4, 2011, 1 page.

Vinke et al. "Thick monolithic scintillation crystals for TOF-PET with depth-of-interaction measurement." IEEE Nuclear Science Symposium Conference Record, Oct. 30, 2010-Nov. 6, 2010, pp. 1981-1984.

Blaine R. Copenheaver, Invitation to Pay Additional Fees and, Where Applicable, Protest Fee. Issued in Application No. PCT/US12/54229, mailed Nov. 2, 2012, 2 pages.

Lee W. Young, Invitation to Pay Additional Fees and, Where Applicable, Protest Fee. Issued in Application No. PCT/US12/46933, mailed Dec. 3, 2012, 2 pages.

Jill Warden, International Preliminary Report on Patentability. Issued in Application No. PCT/US12/46933, mailed Jul. 18, 2014, 25 pages.

Trasis sa. "A solution for the preparation of unit doses of PET and SPECT radiopharmaceuticals." http://www.rsllabin.com/TRASIS-DISPENSER.pdf. Revision date Oct. 2009. 8 pages.

* cited by examiner

"Bubble point"

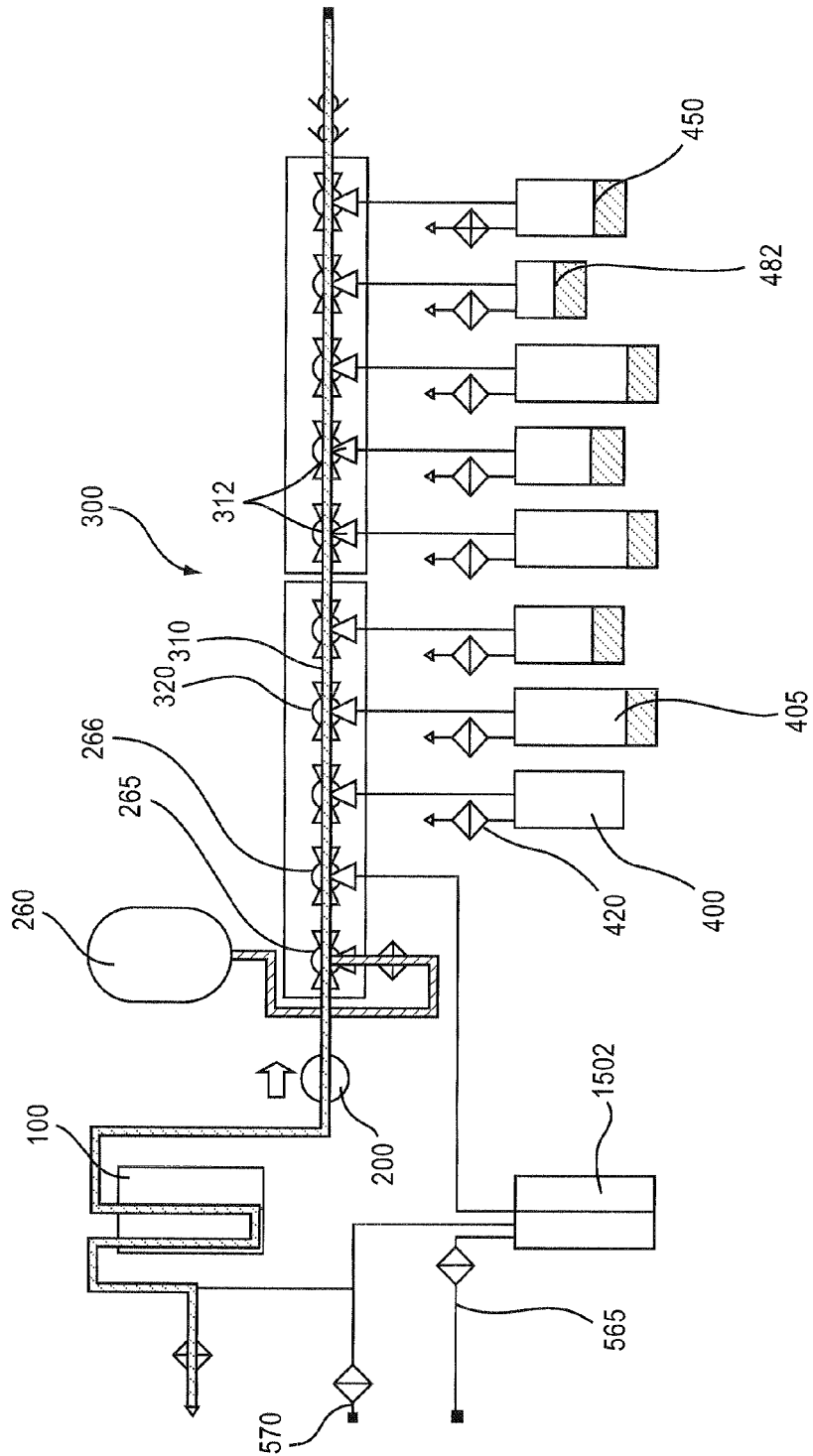

CLOSED VIAL FILL SYSTEM FOR ASEPTIC DISPENSING

This application claims priority to U.S. Provisional Application No. 61/428,041 entitled "CLOSED VIAL FILL SYSTEM FOR ASEPTIC DISPENSING" filed on Dec. 29, 2010, and to U.S. Provisional Application No. 61/508,409 entitled "CLOSED VIAL FILL SYSTEM FOR ASEPTIC DISPENSING" filed on Jul. 15, 2011, the entirety of each is incorporated by reference herein.

BACKGROUND OF THE INVENTION

1. Field of the Invention

Aspects of the present invention relate generally to a vial filling system and methods of use thereof. More specifically, particular aspects of the invention relate to a device for filling vials with measured quantities of a substance or substances, for use in the diagnostic imaging field of nuclear medicine.

2. Description of Related Art

Positron Emission Tomography (PET) is a nuclear medicine imaging technique in which a positron-emitting radionuclide, such as carbon-11, nitrogen-13, oxygen-15 or fluorine-18, is chemically incorporated into a compound normally used by the body, such as glucose, water or ammonia. The compound may then be injected into a patient, for example, so that a targeted biological process of the body will naturally distribute the compound. The radionuclide serves as a tracer for subsequent imaging by a scanner, wherein the decay of the radioisotope produces a record of the concentration of the tissue in the area being imaged, providing a practitioner detailed views of a targeted anatomy in a patient when combined with a Computerized Tomography (CT) study (CT/PET).

Nuclear medicine requires special considerations in the preparation, handling and delivery of radioactive materials for use in various medical procedures. For example, fluorodeoxyglucose (FDG), an analogue of glucose, is commonly used for the chemical incorporation of the radioisotope fluorine-18 for use in PET procedures. Production of the radioisotope fluorine-18 for use in the radiopharmaceutical is often difficult and/or expensive, requiring specialized equipment such as a cyclotron. Thus, the production of the radioisotope often occurs at a remote facility by a third party, from which the hospital or lab receives patient doses ready to inject. Even if the radioisotope happens to be produced on site, final production of the radiopharmaceuticals used in many diagnostic imaging procedures requires manual preparation in a special aseptic environment to ensure a safe injectable product free of environmental contaminants and for precise accounting of the radioactive nature of the radionuclide to be used in the radiopharmaceutical for each procedure, recognizing that the bulk radionuclide product is continuously decaying over time. Furthermore, during preparation of the radiopharmaceutical, the radiopharmacists must be shielded from the ionizing radiation of the radioisotope, and the purity of the radiopharmaceutical must be ensured by filtering and/or avoiding contamination through contact with particles in the air, on a surface, and/or when mixing with a diluting liquid, for example. Thus, because of the short half-life of the radionuclide, the efficient scheduling of patients, for example, along with a safe and efficient preparation of the radiopharmaceutical by technicians is critical in order to avoid wasting the prepared bulk product of the radionuclide.

To create an aseptic environment for the production of pharmaceuticals, a special clean air "canopy" or laminar flow hood, for example, is often used, wherein high-efficiency particulate air (HEPA) filters are provided in conjunction with a closed containment structure, within which the pharmaceuticals can be prepared. The interior environment of the containment structure is closely monitored, for example, by a particle counter, to determine the airborne particulate density of possible contaminates. However, when preparation of the pharmaceutical includes a radioactive material, the aseptic environment described above must also be shielded. It is very difficult to combine a shielded enclosure with a filtered environment without compromising the ability to produce a radiopharmaceutical compound efficiently.

Furthermore, present procedures for dispensing radiopharmaceuticals into final product vials for delivery to one or more patients often involves accessing and extracting the radionuclide product for an individual procedure from a bulk product vial. The bulk product vial may already contain other components, such as sterile water for injection of the radioactive component, or other components may be added to the bulk product vial as necessary or contained/added to each individual vial for mixing with the radionuclide. The bulk product vial, which is contained in a shielded enclosure to minimize exposure of the technician to radiation, is typically accessed by one or more technicians using a syringe to puncture a resealable membrane of the bulk product vial in order to extract a quantity of the radioactive component. Thus, each time a quantity of the radioactive component is extracted in this manner, there is a chance that contaminants can be introduced into the bulk product vial as the syringe punctures and/or is removed from the bulk product vial.

To decrease the chance of contamination by multiple punctures of a syringe, it has been proposed to use an automated syringe that automatically draws material from the bulk product vial into each of the individual vials. However, even if a syringe pump, for example, reduces the chance of contamination by reducing the number of times the bulk product vial membrane is punctured, each plunge of the syringe after the initial plunge risks contamination through airborne particles, for example, being drawn in through the back of the syringe.

Thus, the use of syringes in the preparation of a radiopharmaceutical has inherent drawbacks in preserving the quality and accuracy of a dose to be dispensed for use in a medical procedure, for example. Additionally, syringes can limit the size of a dose being dispensed. For example, when the goal is to withdraw the product from the bulk product vial with one plunge in order to reduce the risk of contamination, a requirement for a 100 ml dose of a product would require the use of an unusually large syringe.

Accordingly, there is a need for a system and associated methods for providing an aseptic, closed path vial fill system that may overcome one or more of the problems discussed above. In particular, there is a need for improved vial filling systems that may promote a more efficient setup and procedure for dispensing radiopharmaceuticals in a safe and effective manner that guarantees the integrity of the radiopharmaceutical every time.

SUMMARY OF THE INVENTION

In accordance with aspects of the present invention, a closed path vial fill system may include a bulk product vial, a peristaltic pump operated by a stepper motor, a dispensing manifold assembly to which may be coupled to at least one final product vial, an optional quality check station, and an optional waste collection system. A control system may be integrated into the system to provide automated control of various aspects of the radiopharmaceutical dispensing process. The system is used to aseptically dispense finished radiopharmaceuticals from a bulk product vial into receiving vessels, such as a Quality Control syringe, a sterility vial, and/or final product vials.

Additional features of various exemplary implementations of the invention will be set forth in part in the description which follows. It will become readily apparent to those skilled in the art from the following detailed description, wherein it is shown and described only in exemplary configurations of a closed vial fill system, that variations of the invention may include other and different aspects of a closed vial fill system capable of modification in various other respects, all without departing from the spirit and scope hereof. Accordingly, the drawings and the detailed description are to be regarded as illustrative in nature and not as restrictive.

BRIEF DESCRIPTION OF THE DRAWINGS

The accompanying drawings, which are incorporated in and constitute a part of this specification, illustrate various exemplary implementations consistent with aspects of the invention, and, together with the description, serve to explain the principles thereof.

FIG. 23A is an illustration of a branched multiple vial connection, in accordance with certain aspects of the present invention;

FIG. 65 is a schematic diagram to illustrate exemplary aspects of a closed vial fill system incorporating a CAV sensor and a method of using the closed vial fill system, in accordance with certain aspects of the present invention.

DETAILED DESCRIPTION

Figure 1:
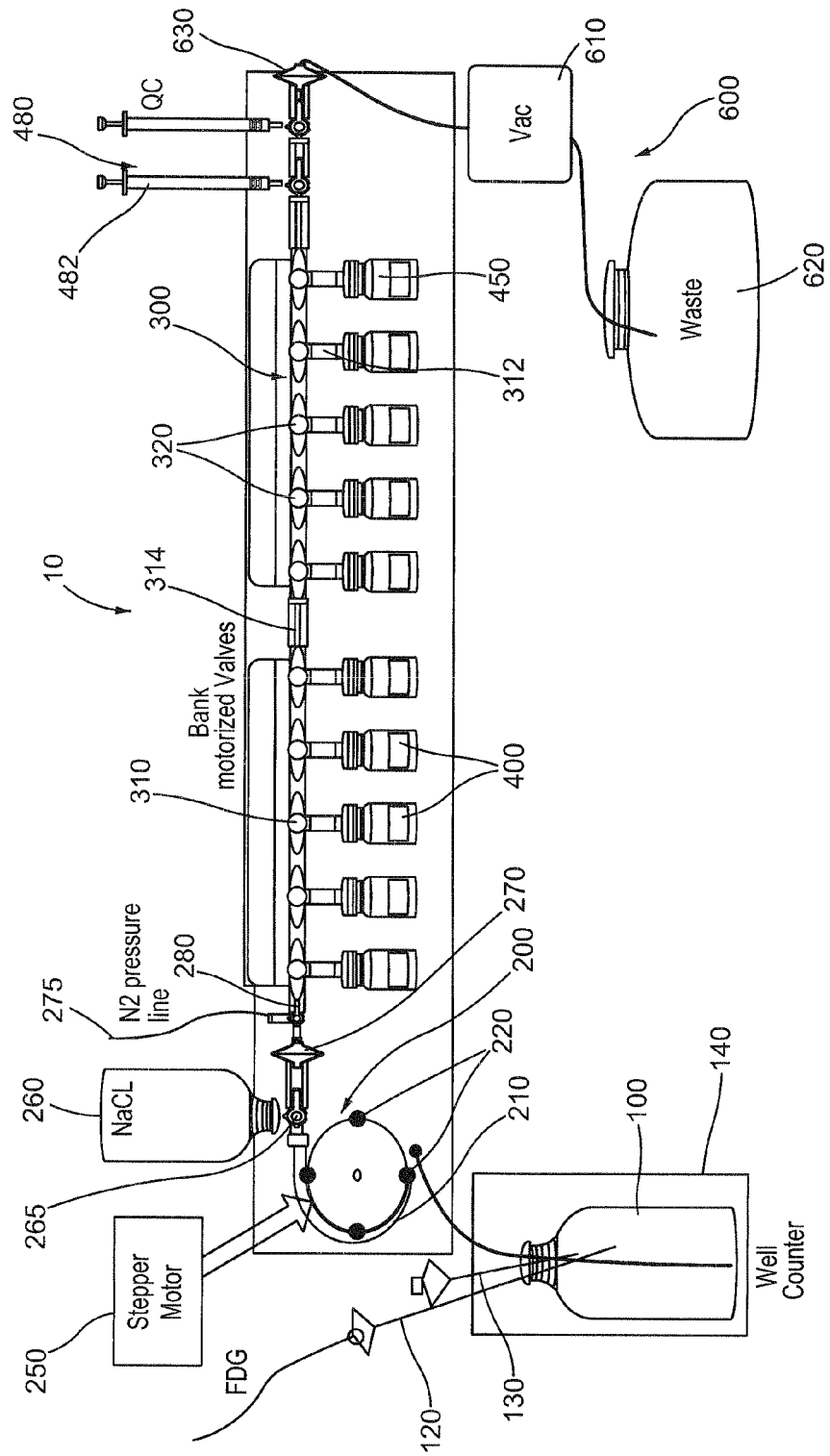
FIG. 1 is an illustration of a closed path vial fill system, in accordance with certain aspects of the present invention.

Various aspects of a closed path vial fill system may be illustrated by describing components that are coupled, attached, and/or joined together. As used herein, the terms "coupled", "attached", and/or "joined" are interchangeably used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements shown in said examples.

Relative terms such as "lower" or "bottom" and "upper" or "top" may be used herein to describe one element's relationship to another element illustrated in the drawings. It will be understood that relative terms are intended to encompass different orientations of a closed path vial fill system in addition to the orientation depicted in the drawings. By way of example, if aspects of a closed path vial fill system shown in the drawings are turned over, elements described as being on the "bottom" side of the other elements would then be oriented on the "top" side of the other elements as shown in the relevant drawing. The term "bottom" can therefore encompass both an orientation of "bottom" and "top" depending on the particular orientation of the drawing.

Various aspects of a closed path vial fill system may be illustrated with reference to one or more exemplary implementations. As used herein, the term "exemplary" means "serving as an example, instance, or illustration," and should not necessarily be construed as preferred or advantageous over other variations of the devices, systems, or methods disclosed herein.

As shown in FIG. 1, an exemplary closed path vial fill system 10 may include a bulk product vial 100, a peristaltic pump 200, a dispensing manifold assembly 300 to which may be coupled at least one final product vial 400, a sterility vial 450, an optional quality check station 480, and an optional waste collection system 600. A control system 700 (e.g., see FIG. 27) may be integrated into the system 10 to provide automatic and/or manual control over various aspects of the radiopharmaceutical dispensing process. Although described herein as having one pump 200 or one bulk product vial 100, for example, the system may encompass multiple pumps feeding multiple fluid pathways for dispensing multiple different products without cross contamination. The potential exposure of technicians may be further reduced, as the necessity to enter the shielded environment in order to change out disposable components of the system 10 between batches (radiation safety hazard) may be further reduced.

As shown in FIG. 1, the peristaltic pump 200 may be a simple mechanical pump comprising a replaceable tube element 210 and rollers 220, for example. The rollers 220 are conventionally provided at intervals along a radial track and rotate about a central axis to exert localized pressure on the tube element 210, which in turn pushes a fluid through the tube element 210 and creates a negative pressure at an inlet of the tube element 210 for drawing additional fluid into the tube element 210. Control of the fluid flow may be by way of a standard motor (not shown) coupled to the peristaltic pump 200. However, as shown in FIG. 1, by attaching a stepper motor 250, for example, to the peristaltic pump 200, aspects of the present invention permit a much more refined degree of control over the fluid flow parameters through the tube element 210. For example, by calibrating the rotation of the pump 200 in accordance with the rotation of the stepper motor 250, as determined by a number of pulses applied by the stepper motor 250 over a given period of time, a control algorithm may be determined to accurately predict and control the amount of fluid being pushed through the tube element 210 as a function of the number of pulses of the stepper motor 250.

In accordance with another aspect of the invention, the control system 700 may be used to store calibration data for each position of a final product vial 400 along the dispensing manifold assembly 300, permitting very precise control of the fluid flow parameters into each final product vial 400 without the need for individual flow meters for each final product vial 400. Although referred to herein as a final product vial 400, the final product vial 400 may be any suitable vessel for receiving a quantity of the radiopharmaceutical product, including a sterility vial, final product vial, or a quality control syringe, for example.

According to another aspect of the present invention, the stepper motor 250 may be used to operate the peristaltic pump 200 in reverse. As such, the closed path vial fill system 10 may be used to draw a diluting solution, such as a sterile saline solution, from a dilution container 260, for diluting the bulk radionuclide product in the bulk product vial 100. The dilution container 260 may be a flexible, sterile bag comprised of a resilient PVC material, for example. As shown in FIG. 1, the dilution container 260 may be integrated into the system 10, preferably between the peristaltic pump 200 and the dispensing manifold assembly 300, by way of a valve 265. The valve 265 may be a three-port solenoid valve, a diverter valve, or a stopcock valve, for example, and provides closed fluid communication between the peristaltic pump 200 and the dispensing manifold assembly 300 when selectively actuated to a first position, and closed fluid communication between the dilution container 260 and the peristaltic pump 200 when selectively actuated to a second position.

Figure 2:
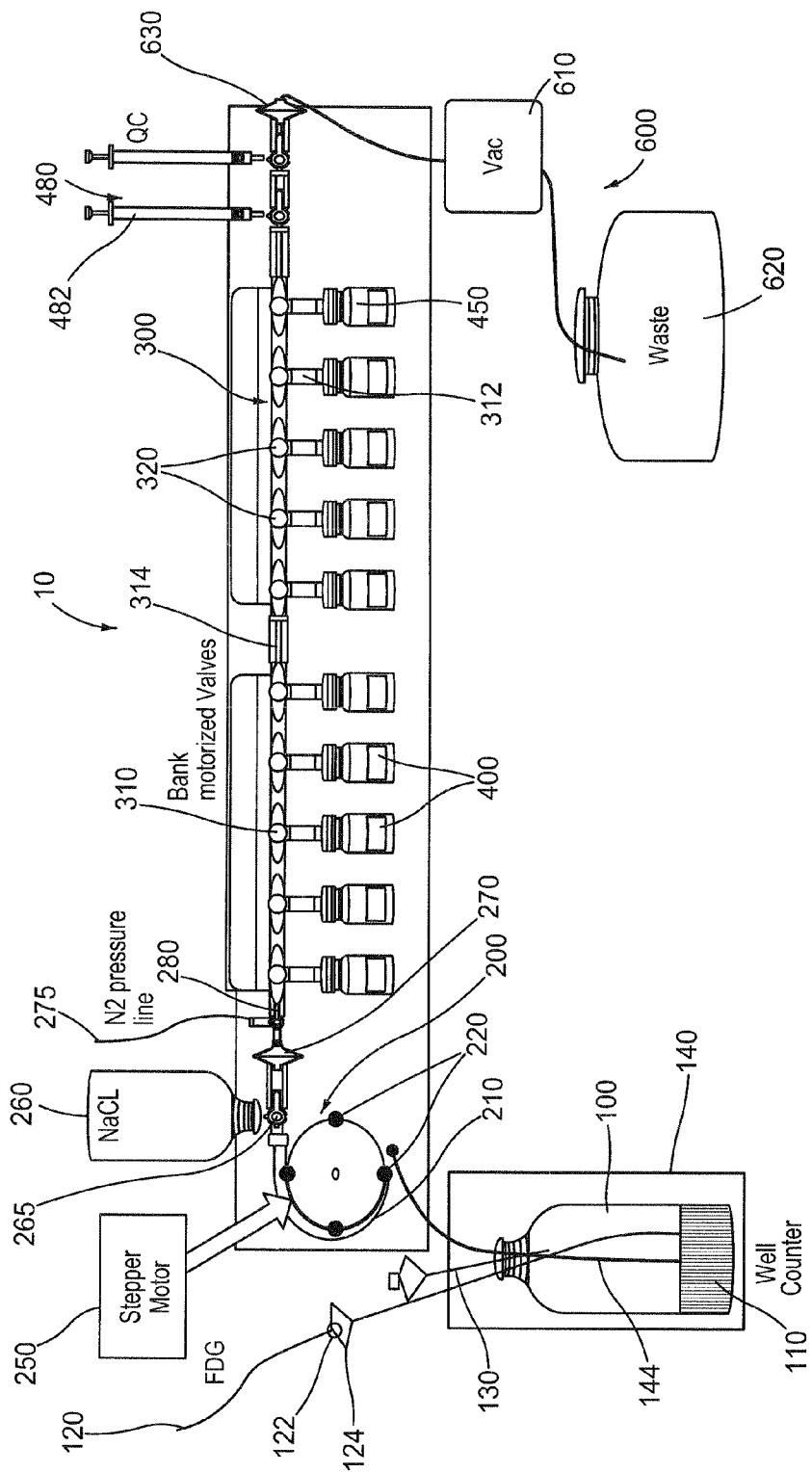
FIG. 2 is another illustration of the closed path vial fill system of FIG. 1, in accordance with certain aspects of the present invention.

As shown in FIG. 2, for example, a typical deposit of the bulk radiopharmaceutical product 110 may include a select amount of the radiopharmaceutical product 110, such as FDG (fluorodeoxyglucose) or FMISO (fluoromisonidazole), for example, delivered from a chemistry synthesis unit (CSU) through a section of tubing 120, an air eliminating filter (AEF) 122, and a sterilizing filter 124, such as a 0.2 µm liquid filter, into the bulk product vial 100. A filtered vent needle 130 may be provided to vent the interior of the bulk product vial 100 as the radiopharmaceutical product 110 is loaded into the bulk product vial 100. An aspirating needle 144, for example, may be used to puncture the septum of the bulk product vial 100 for connection to the tube element 210, such as by way of a luer lock, for example (see also FIG. 10). With the aspirating needle 144 inserted to place an intake near a bottom surface of the bulk product vial 100, the dispensing manifold assembly 300 is placed in fluid communication with the bulk product vial 100 to pull substantially all of the bulk product from the bulk product vial 100. The bulk product vial 100 may be enclosed by a shielded box, 140, and a well counter (not shown), for example, or any suitable dose calibrator, may be provided to assay the radioactivity level of the deposited bulk radiopharmaceutical product 110 in the bulk product vial 100. In accordance with the measured radioactivity level of the deposited bulk radiopharmaceutical product 110, the stepper motor 250 may be activated to operate the peristaltic pump 200 in reverse to provide a predetermined amount of the dilution solution to the bulk product vial 100.

Figure 3:
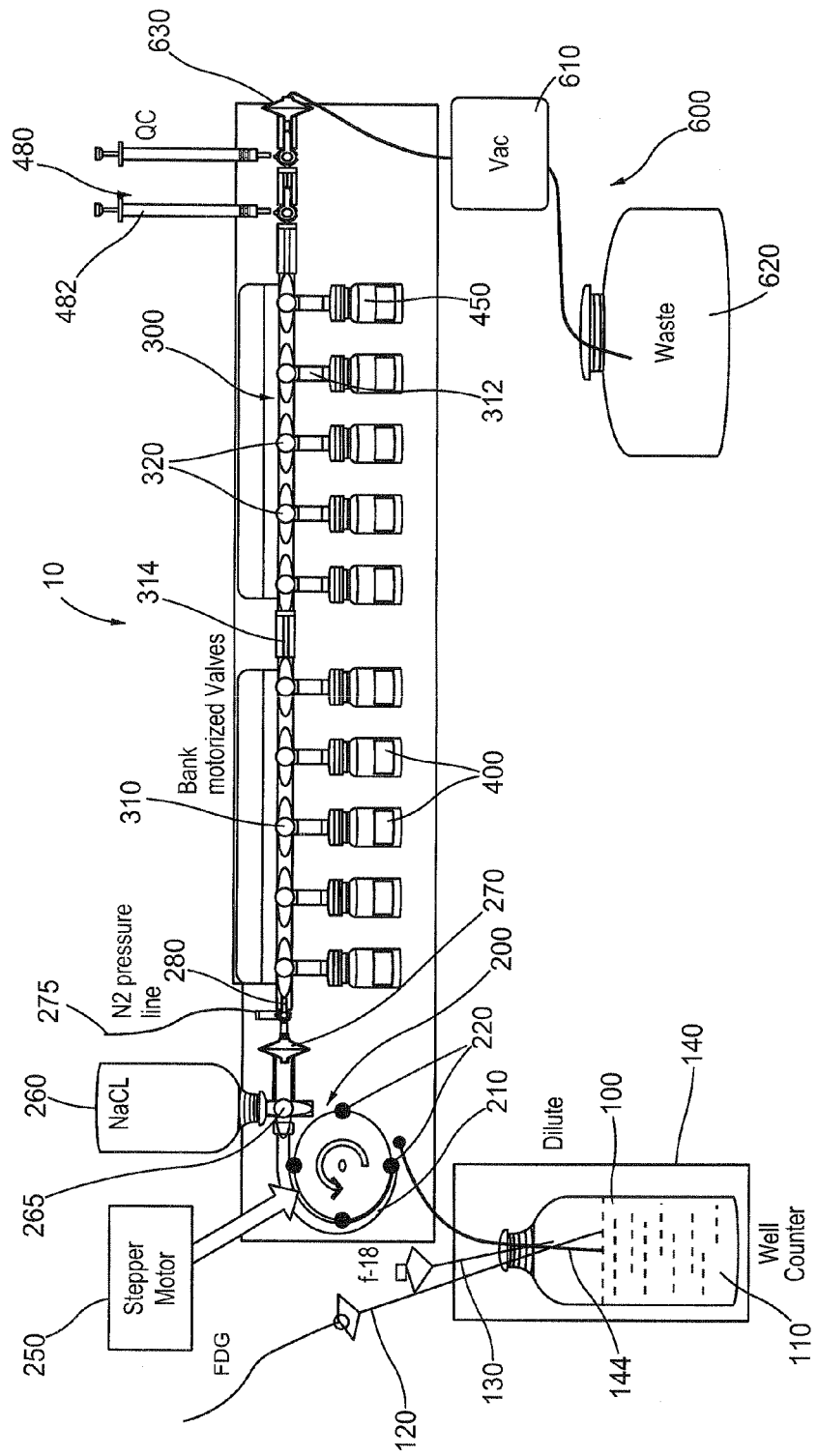
FIG. 3 is another illustration of the closed path vial fill system of FIG. 1, in accordance with certain aspects of the present invention.

As shown in FIG. 3, with the valve 265 closed to the dispensing manifold assembly 300 and open to the dilution container 260, the stepper motor 250 may be controlled to operate the pump 200 for a predetermined time to deliver the predetermined amount of dilution solution into the bulk product vial 100. The control system 700 may be used to store calibration data with respect to an initial void of fluid in the pump 200 when the stepper motor 250 is initially activated. For example, by accounting for the dimensions of the tube element 210, the system 10 may be controlled to deliver a precise amount of dilution solution from the dilution container 260 into the bulk product vial 100, accounting for the initial volume of air in the tube element 210. In accordance with another aspect of the present invention, a fluid sensor may be provided at a specific point near the entrance and/or exit of the peristaltic pump 200, so that specific stepper motor control over the fluid flow through the pump is not initiated until the fluid sensor senses a liquid flow, indicating the pump has cleared any air in the tube element 210. With the deposited radiopharmaceutical product 110 in the bulk product vial 100 thus diluted for injection, the valve 265 may be closed to the dilution container 260 and opened to the dispensing manifold assembly 300 for extracting the diluted solution from the bulk product vial 100 and dispensing the radiopharmaceutical solution into the individual final product vials 400 for use in a procedure.

As shown in FIGS. 1-3, the dispensing manifold assembly 300 may include one or more central manifold tubes 310. Each central manifold tube 310 may include a central flow tube and a number of dispensing ports 312 for dispensing an injection solution into an individual vial 400. In accordance with another aspect of the present invention, each end of the manifold tube 310 may include a connecting means 314, such as a luer connection, or an externally threaded end, for example, for secure attachment of tubes, connectors, and/or another manifold tube 310, to permit efficient expansion of the system 10, if desired. Although depicted in FIGS. 1-3 as having two manifold tubes 310, with each manifold tube 310 having five dispensing ports 312 in a linear arrangement, the system 10 may include one or more manifold tubes 310, with each manifold tube 310 having one or more dispensing ports 312. In accordance with yet other aspects of the present invention, the system 10 may be configured to provide the dispensing ports 312 in a variety of arrangements. For example, the manifold tubes 310 may be formed in a circular shape, or a y-connector and valve assembly may be used to provide multiple manifold tubes 310 in a parallel arrangement. The manifold tubes 310 may be formed from any suitable high-strength, hard plastic, such as nylon, polypropylene, polycarbonate and/or polyvinylidene fluoride (PVDF), which allows sterilization of the tubes 310, such as by steam sterilization or gamma radiation sterilization, and easy removal and disposal of the manifold tubes 310 after each dispensing run, for example.

Valves 320, such as three-port solenoid valves, for example, may be provided at the junction of each dispensing port 312 and the manifold tube 310. Each valve 320 may be selectively actuated between multiple operational positions, including a first valve position, which shuts off fluid flow to the dispensing port 312 and allows unimpeded, substantially laminar fluid flow through the manifold tube 310, and a second valve position, which diverts the fluid flow in the manifold tube 310 toward the dispensing port 312 associated with the valve 320. Each valve 320 may be pneumatically, hydraulically, and/or electrically actuated between operational positions, and control may be automated through the control system 700. In this manner, each valve 320 may be provided with a dedicated control motor, for example, or a single source of power may be provided to actuate all valves 320.

As shown in FIGS. 1-3, a sterilization filter 270, such as a 0.22 micron antimicrobial filter, may be provided between the valve 265 and the dispensing manifold assembly 300. Alternatively, the filter 270 may be located prior to the pump 200, or in any location along the closed path between the bulk product vial 100 and the vials 400. Any of the radiopharmaceutical products intended for dispensing into a final product vial 400 must pass through the sterilization filter 270, which is required by government regulation to ensure the integrity of the final radiopharmaceutical product planned for injection into a subject. Furthermore, the integrity of the sterilization filter 270 must be tested and verified following use in the system 10.

Figure 4:
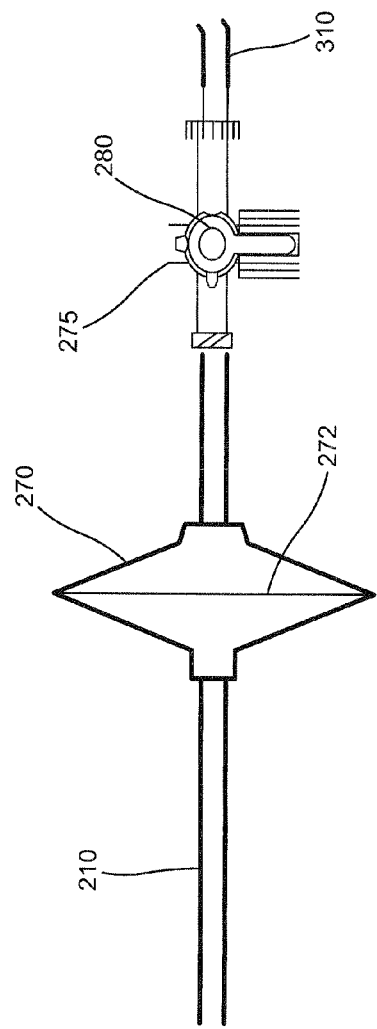
FIG. 4 is an illustration of an in-situ filter testing assembly, in accordance with certain aspects of the present invention.
Figure 5:
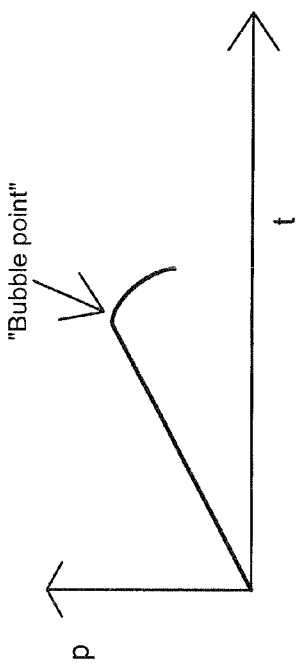
FIG. 5 is a pressure graph to illustrate aspects of the in-situ filter testing assembly, in accordance with certain aspects of the present invention.

Aspects of the present invention may optionally include an in-situ filter integrity testing system. Normally, following the dispensing process, a technician must dismantle and remove the filter from the dispensing system to apply a nitrogen pressure test to the filter as an integrity test. The procedure may introduce additional exposure risk to the technician. The in-situ filter integrity testing system of the present invention includes a pressurized gas line 275 that may be connected through a diverter valve 280, for example, to enter the fluid flow path on a downstream side of the sterilization filter 270, between the filter 270 and the first manifold assembly 310. As shown in FIG. 4, in-situ filter integrity testing may be provided by opening the diverter valve 280 to allow pressurized gas, preferably nitrogen gas, to flow from the pressurized line 275 upstream toward the sterilization filter 270. As shown in FIG. 5, a pressure on the downstream side of the sterilization filter 270 will presumably increase until the filter fails, such as by puncture failure of a diaphragm element 272, for example. Any suitable pressure sensor may be provided to record the pressure on the downstream side of the filter 270. Because a failure pressure (i.e., bubble point) has been predetermined for the filter 270, which may be in the range of 40-50 psi for a typical 0.22 micron filter, for example, as long as the pressure on the downstream side of the filter increases as expected to a minimum threshold value, the test may be considered a success and the integrity of the filter 270 validated. However, if the pressure on the downstream side of the filter 270 fails to increase as expected, or increases but fails to reach the minimum threshold value, the test may reveal a failure in the filter 270 and the integrity of the dispensed radiopharmaceutical products may be suspect. The filter 270 may then be removed from the system 10, for example, and retested to verify the results.

According to another aspect of the present invention, in-situ filter integrity testing may be provided by installing a suitable gas flow detector element on the upstream side of the filter 270, i.e., the side closest to the pump 200. Accordingly, when the downstream side of the filter 270 is pressurized by opening of the diverter valve 280, if the gas flow detector senses any gas flow, or a gas flow through the filter 270 above a minimum flow threshold, for example, the filter 270 may be determined to have failed the integrity test and the radiopharmaceutical product dispensed through the filter declared suspect. Additional testing on the filter and/or dispensed product may be ordered to determine if the product may be contaminated or is safe for injection.

Figure 6:
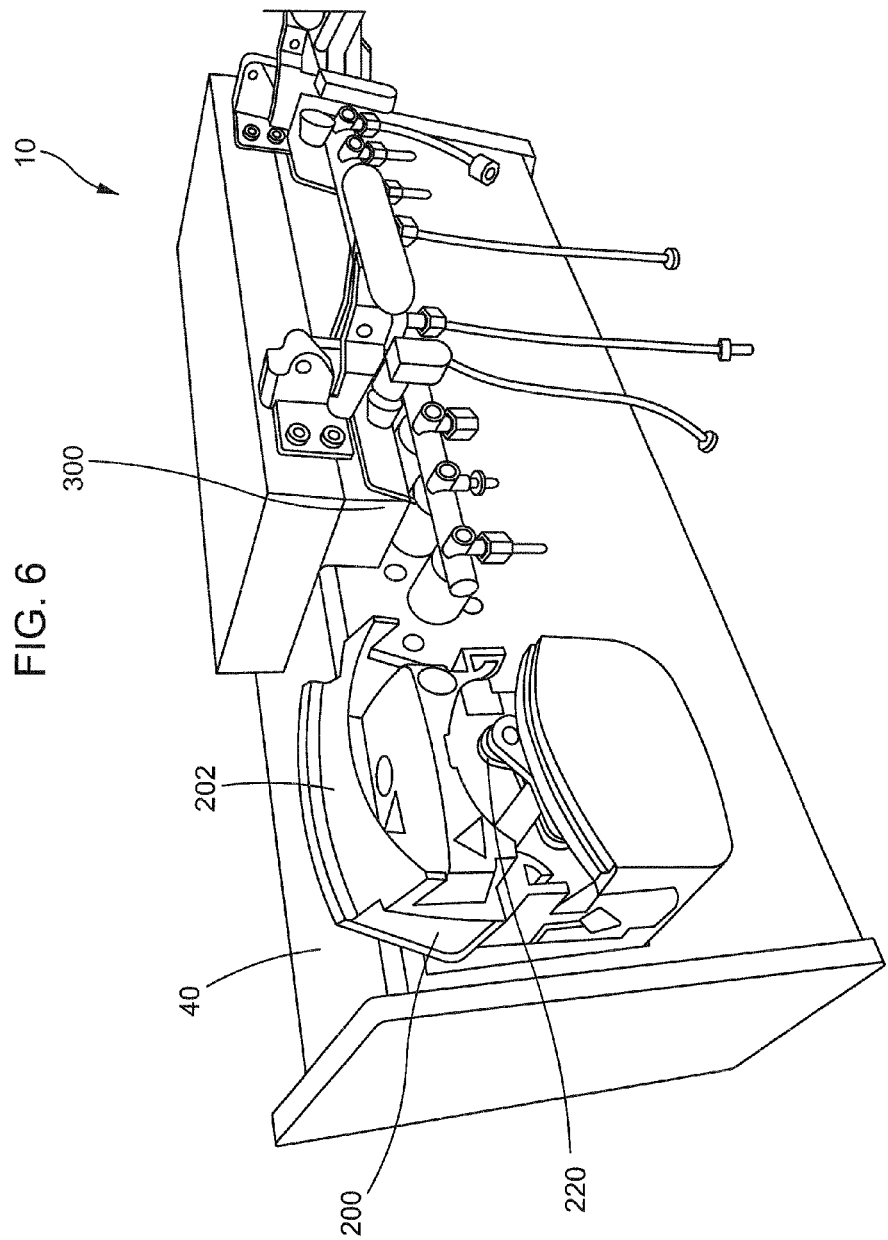
FIG. 6 is a perspective view of a partially assembled closed path vial fill system, in accordance with certain aspects of the present invention.
Figure 7:
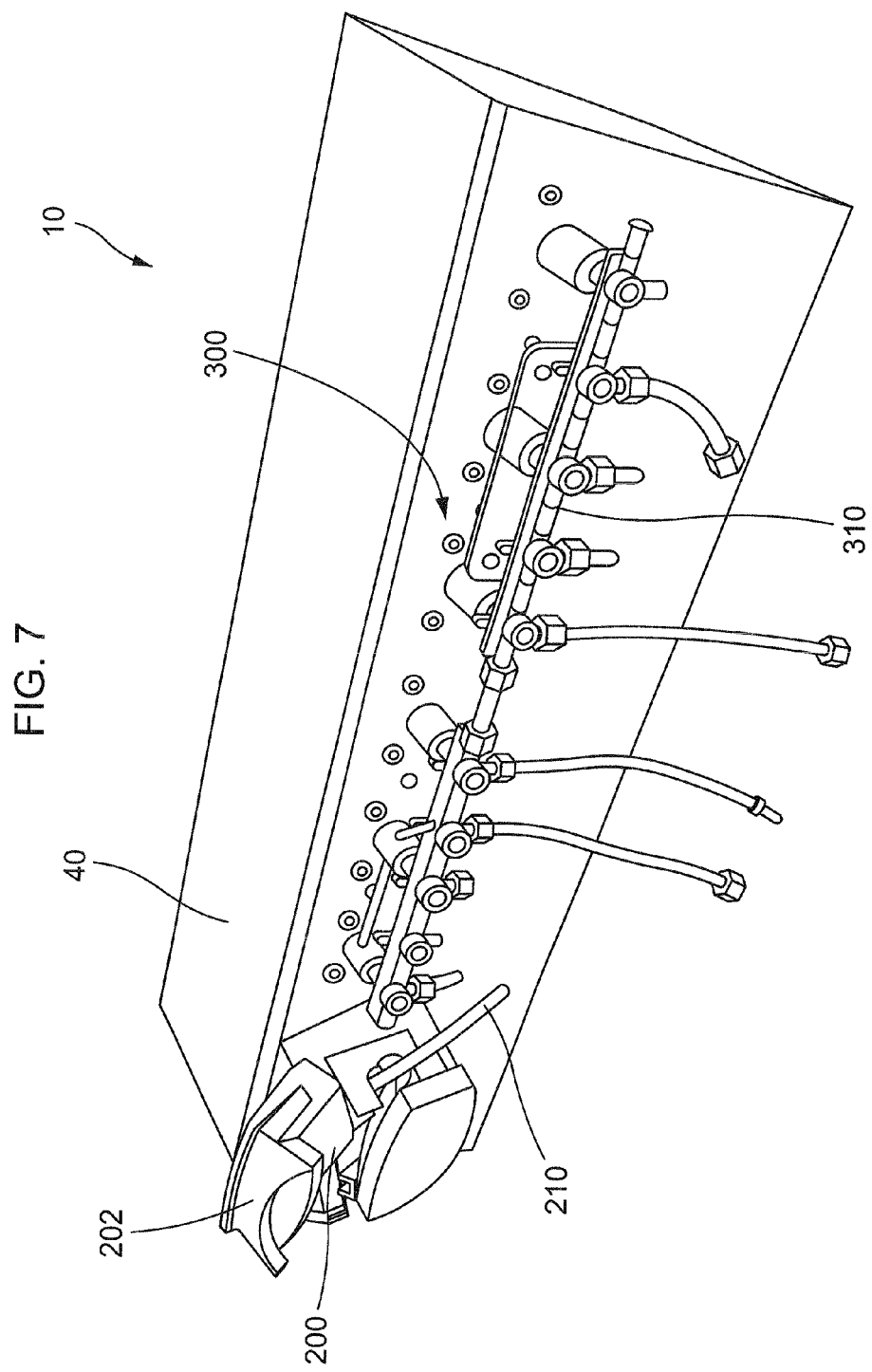
FIG. 7 is a top perspective view of a partially assembled closed path vial fill system, in accordance with certain aspects of the present invention.
Figure 8:
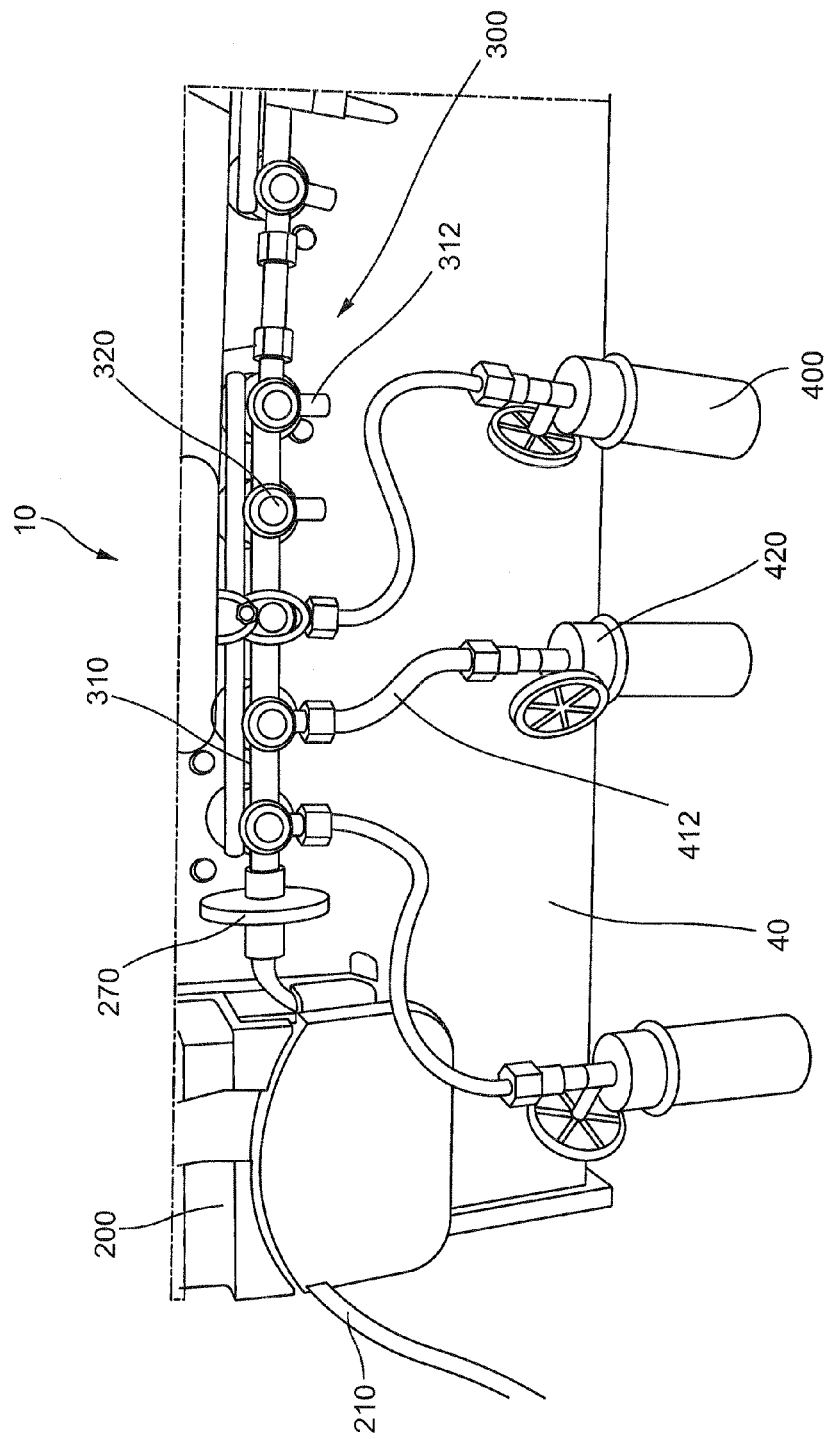
FIG. 8 is a front view of aspects of a partially assembled closed path vial fill system, in accordance with certain aspects of the present invention.

The system 10 may be set up as shown in FIGS. 6-8. A frame 40, which may be a hollow parallelepiped constructed from aluminum, for example, may be provided for mounting the various structural and disposable elements of the system 10. For example, the peristaltic pump 200 may be securely mounted toward one side of the frame 40. The stepper motor 250 may be integrated with the pump 200 or mounted to an interior portion of the frame 40. As shown in FIG. 6, the pump 200 may have a cover 202 that opens for access to an interior compartment and the rollers 220. As shown in FIGS. 7 and 8, the tube element 210 may be inserted into the pump 200 between the rollers 220 and an outer race so that both ends of the tube element 210 extend from the pump 200. As shown in FIG. 8, one end of the tube element 210 connects to the filter 270 which, in turn, connects to the manifold tube 310 of the dispensing manifold assembly 300. The other end of the tube element 210 may be connected to the bulk product vial 100 by any suitable means to ensure that the suction pressure of the pump 200 will draw product from the bulk product vial 100 into the tube element 210.

The rotary actuators that control the rotary motion of the valves 320 may be mounted through mounting holes provided in the frame 40. As shown in FIG. 8, the manifold tubes 310 may be mounted so that the rotary actuators selectively actuate each of the valves 320. The final product vials 400 may then be attached to each of the dispensing ports 312, as necessary, in preparation for a dispensing run As described below in greater detail, the final product vials 400 may be attached to the dispensing ports 312 in an aseptic environment prior to mounting on the chassis of the manifold assembly. Each vial 400 may be directly connected to a dispensing port 312 or connected via a connector tube 412, for example. As shown in FIG. 8, vial caps 420, such as vented fill vial caps, may be provided with each vial 400 for connection to a dispensing port 312. The fill caps 420 provide a sealed disconnect so that the vials 400 may be removed from the system 10 without external exposure to the radiopharmaceutical contained therein.

Figure 10:
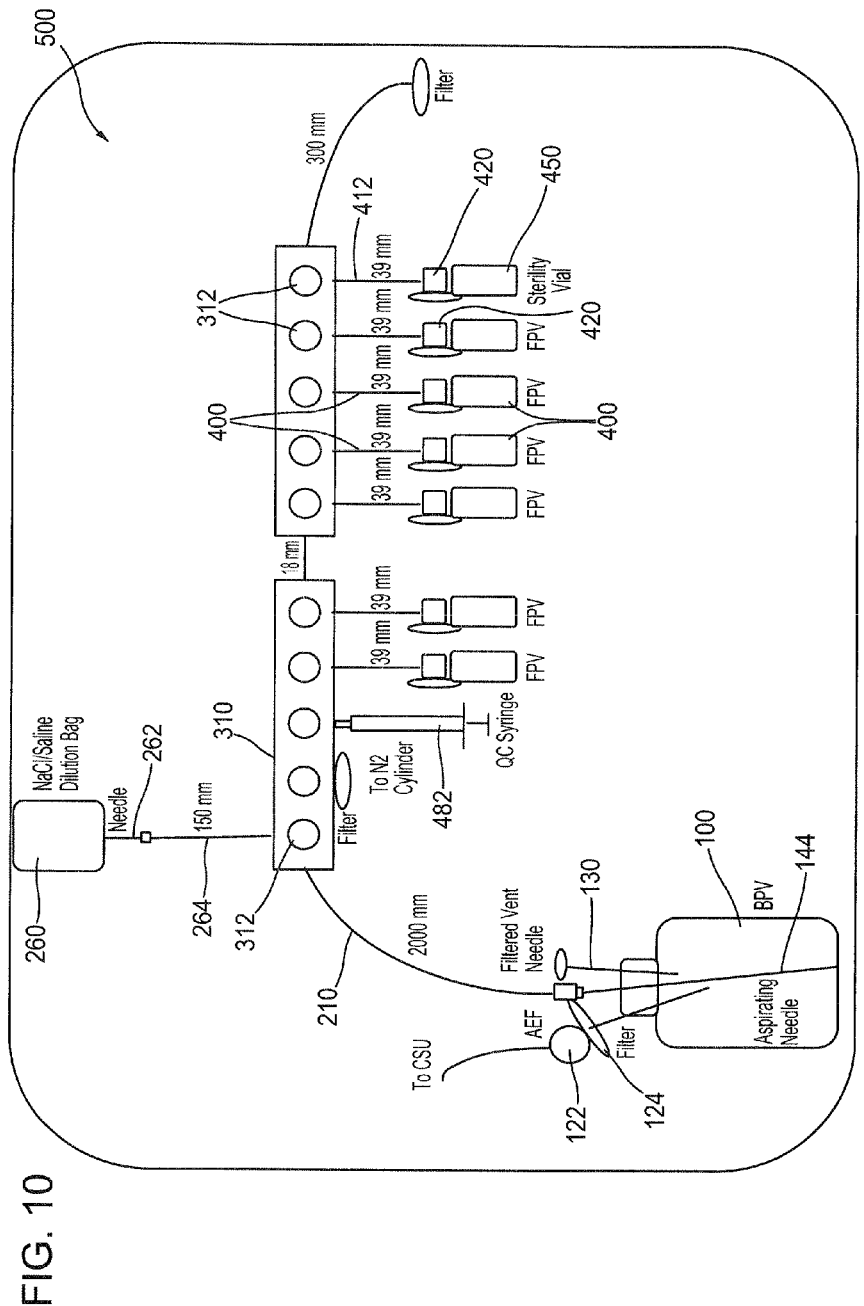
FIG. 10 is an illustration of a sterile kit assembly for use with a closed path vial fill system, in accordance with certain aspects of the present invention.

As shown in FIGS. 1-3, the system 10 may include a quality check station 480. Although depicted as a separate element attached to a distal end of a manifold tube 310, the quality check station may simply include a syringe or quality check vial 482 connected to one of the dispensing ports 312, as shown in FIG. 10, for receiving a quantity of the dispensed radiopharmaceutical product. Thus, a sample of the radiopharmaceutical product being dispensed into the vials 400 may be retrieved for appropriate testing of purity, clarity, and the safety of the product. For example, an FDG product may be checked to ensure it is free of particulates, is the right pH, and/or contains an appropriate concentration of active radionuclide.

In accordance with another aspect of the present invention, one or more of the final product vials 400, containing a representative quantity of dispensed radiopharmaceutical, may be identified as a sterility vial 450, wherein the sterility vial 450 may be removed from the system 10 and the contents subjected to sterilization testing using a culture medium, for example, to determine if the radiopharmaceutical had been compromised during the compounding and/or dispensing process.

Figure 9:
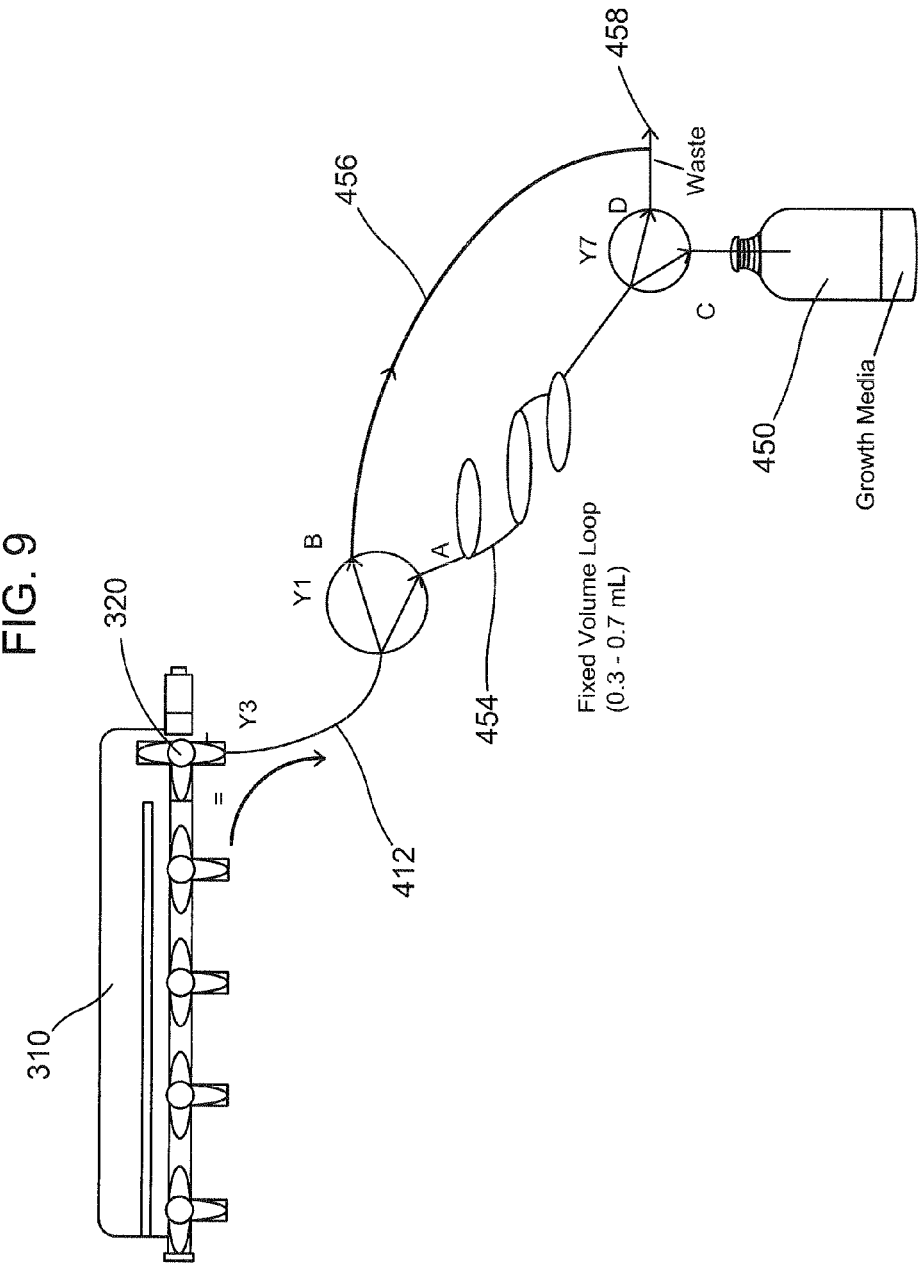
FIG. 9 is an illustration of aspects of a closed path vial fill system having an in situ sterility testing system, in accordance with certain aspects of the present invention.

In another aspect according to the present invention, an in situ sterility test may provide an additional built in quality check for the closed vial fill system 10. Typically, a small volume sample of the radiopharmaceutical may be drawn into a syringe from a final product vial 400, for example, and then dropped into a growth media. By using a sterility vial 450 already containing a culture medium, for example, aspects of the present invention permit performing an in situ quality check of the sterility of the radiopharmaceutical. However, the accuracy of the volume of the product used with the growth media can greatly impact the results of the test. Accordingly, as shown in FIG. 9, a high performance liquid chromatography (HPLC) load loop method may be used in conjunction with the sterility vial 450 to allow accurate, repeatable aliquots of liquid to be dispensed into the sterility vial 450.

The method involves attaching one end of the connector 412, for example, to a dispensing port 312 of the manifold tube 310. The distal end of the connector 412 may be connected to a valve V1 which, as shown in FIG. 9, for example, may be a two-way valve that actuates between an A position and a B position. In the A position, the valve V1 provides fluid communication between the connector 412 and a proximal end of a fixed volume loop 454. In the B position, the valve V1 provides fluid communication between the connector 412 and an exit line 458, which could also be a catch vial, for example, and which may be by way of a secondary tube 456. A distal end of the fixed volume loop 454 may be connected to a two-way valve V2 which actuates between a C position and a D position. In the C position, the valve V2 provides fluid communication between the fixed volume loop 454 and the sterility vial 450. In the D position, the valve V2 provides fluid communication between the fixed volume loop 454 and the exit line 458. The fixed volume loop 454 may be a looped tube, for example, as shown in FIG. 9, which when completely filled provides an accurate volume of fluid, typically less than 1 ml. To begin the sterility test, the valve 320 is opened and the peristaltic pump 200 operated to provide radiopharmaceutical product into the connector 412. The valve V1 is placed in the A position and the valve V2 is placed in the D position. Radiopharmaceutical product may be pumped through the loop 454 until reaching the waste line, at which point the valve V1 is switched to the B position and then the valve V2 is switched to the C position. Pressurized gas from the gas line 275 may be used to then blow gas through the valve 320 in order to remove residual product to waste. After a predetermined interval, the valve V1 may be switched back to the A position to drive the fixed volume of radiopharmaceutical product contained in the fixed volume loop 454 into the sterility vial 450. Because the sterility vial 450 contains a growth media, the technician may then directly determine the sterility of the sample of product.

As shown in FIGS. 1-3, the system 10 may also include a waste collection system 600, comprising an optional vacuum pump 610 and a waste receptacle 620. Another sterilization filter 630 may be provided to prevent any backflow contamination from entering the closed fill path during a dispensing operation.

Figure 11:
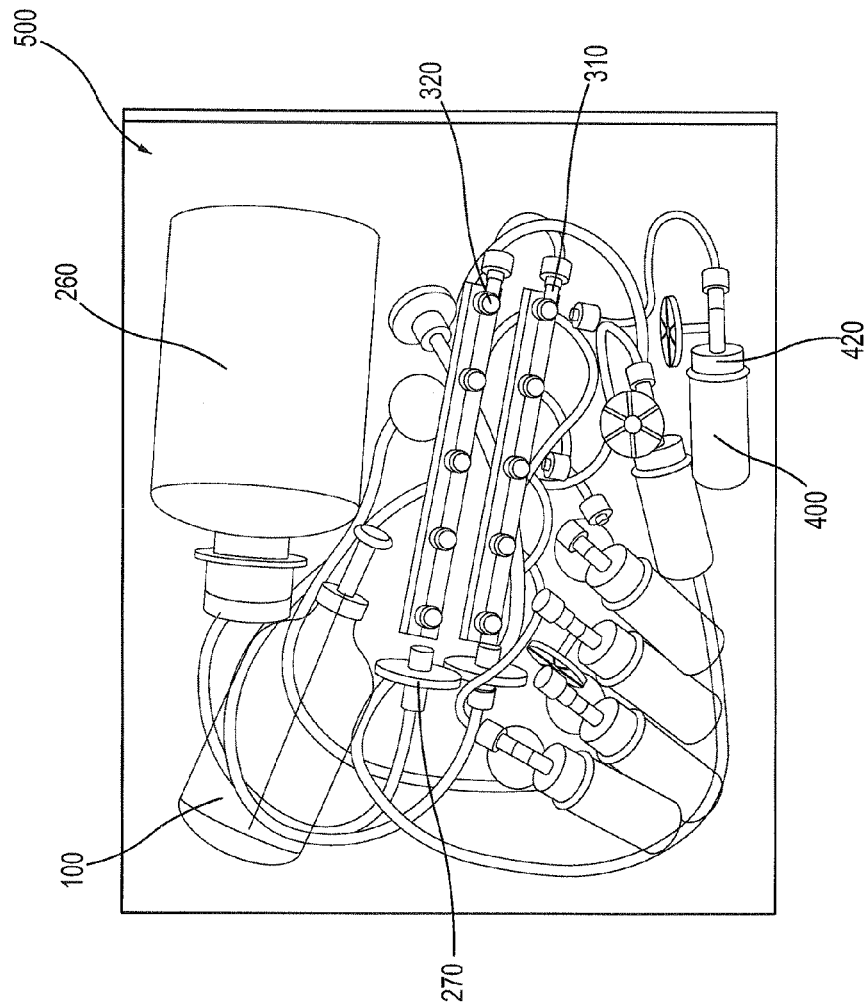
FIG. 11 is a top view of a packaged sterile kit assembly for use with a closed path vial fill system, in accordance with certain aspects of the present invention.

As described above, a closed path system 10 may be formed that includes the bulk product vial 100, the tube element 210 as mounted in the peristaltic pump 200, the dilution container 260, the sterilization filter 270, the dispensing manifold assembly 300, including the manifold tubes 310 and valves 320, and the final product vials 400, all of which may be disposable elements that can be removed after each production run and easily and efficiently replaced with new elements for the next production run. As shown in FIGS. 10 and 11, a sterile kit 500 may be provided for each new compounding run of a radiopharmaceutical that includes one or more of the bulk product vial 100, the dilution container 260, prefilled with the dilution solution, the filter 270, the manifold tubes 310 and valves 320, and the final product vials 400, including the vented fill caps 420. The kit 500 may come with certain or all of the components preassembled to allow for efficient set up of the system 10.

The kit 500 may be aseptically assembled inside a laminar flow hood inside a clean room prior to packaging for delivery and use. The kit components may be sterilized through a gamma radiation sterilization technique, or where the final product vials 400 may be susceptible to damage from the gamma radiation, for example, steam sterilization techniques may be used. Accordingly, the kit components may arrive sterilized with some of the components already connected. The dilution container 260, sterility vial 450, final product vials 400, and vented fill caps 420 for each sterility vial 450 and final product vial 400 may require cleaning. Although the inside and/or contents of each of the components may be sterile, the outside surfaces and, in particular, the septa, or resealable membranes of the vials, may be sterilized with alcohol wipes prior to use in the kit. For example, the vented fill cap 420 packages may be opened in the laminar flow hood, however, the packages should be soaked in hydrogen peroxide or alcohol prior to placement in the laminar flow hood. The vented fill caps 420 in the packages are sterile and therefore do not require additional sterilization upon being released from the packages when in the laminar flow hood.

Figure 22:
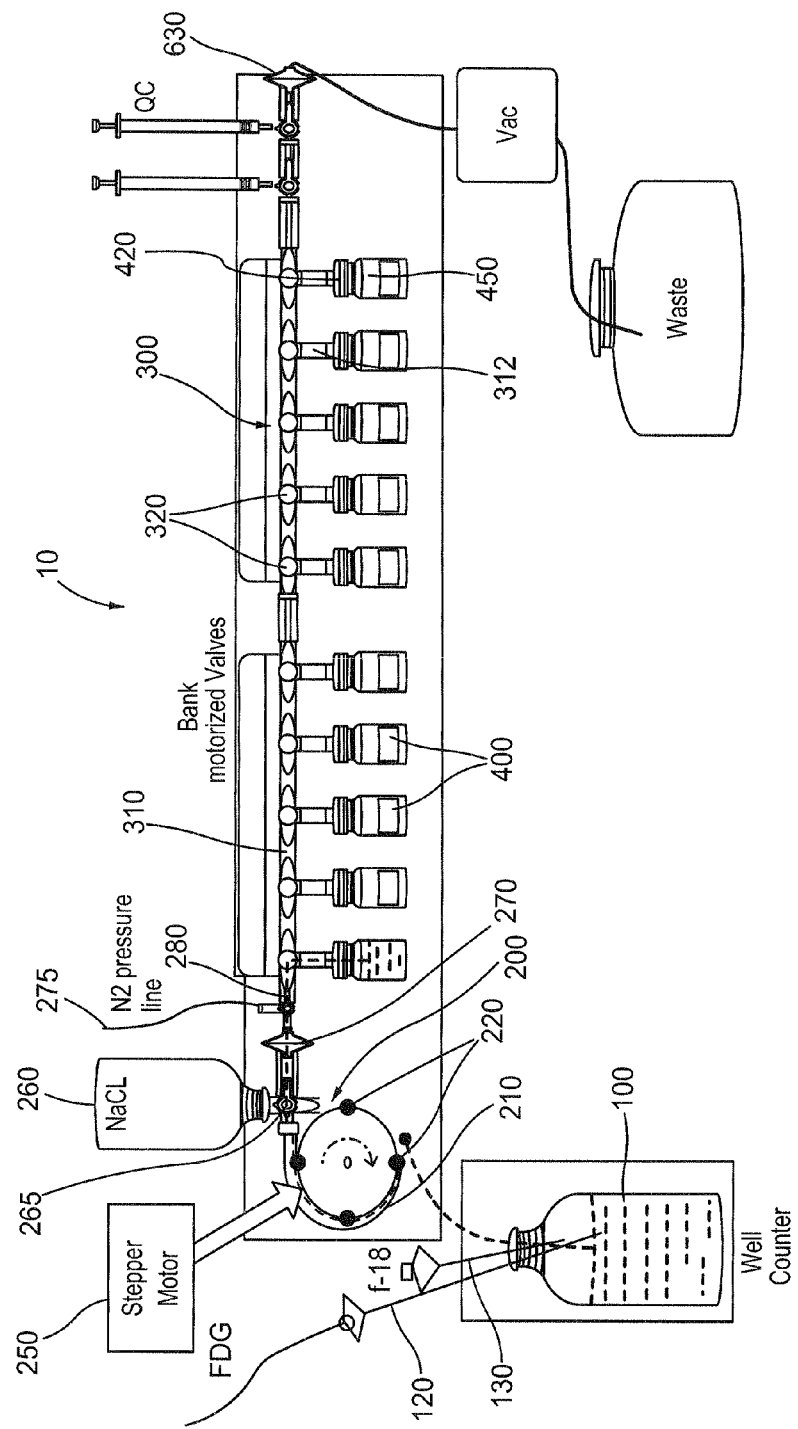
FIG. 22 is an illustration of a vial fill procedure in accordance with certain aspects of the closed path vial fill system of FIG. 1.

As shown in FIG. 10, once sterilized in the hood, the dilution container 260 and vials 400/450 may be connected to the other sterile kit components. The dilution container 260 may be connected by inserting a needle 262 through the dilution container's septum. A dilution tube 264 may be connected to a distal end of the needle 262 and connected to the manifold tube 310 through a valve, as shown in FIG. 22, for example, by valve 265. According to another aspect of the invention, the dilution tube 264 may be configured to connect directly to one of the dispensing ports 312, as shown with regard to the first port in FIG. 10. Vented fill caps 420 may be mounted to the dispensing ports 312 directly, or by way of the connector tubes 412, for example, according to the number of final product vials 400 desired and/or to accommodate the sterility vial 450. The final product vials 400 and the sterility vial 450 may then be connected to the corresponding vial caps 420, as appropriate. In this manner, it may be preferable to connect the sterility vial 450 to the dispensing port 312 sequentially farthest from the pump 200 as compared to the final product vials 400. In addition, if a mixture of vial sizes is being used in the system 10, larger final product vials 405 (see FIG. 23) may be arranged to connect to dispensing ports 312 along with the smaller final product vials 400 in any desired sequence with respect to the pump 200.

Figure 13:
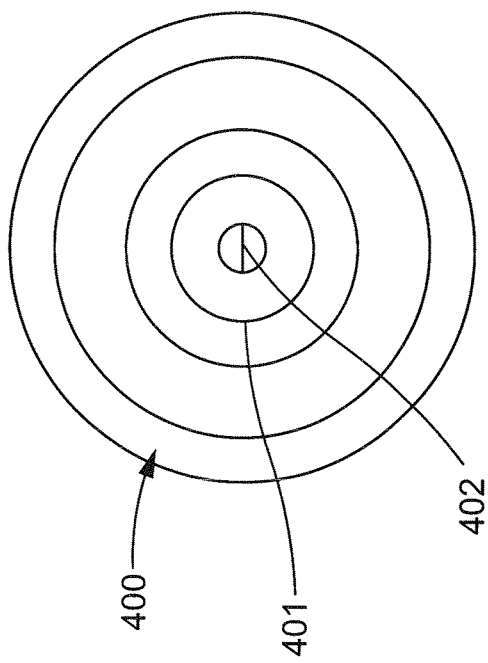
FIG. 13 is a top view of a vial with a pierced septum, in accordance with certain aspects of the present invention.
Figure 12:
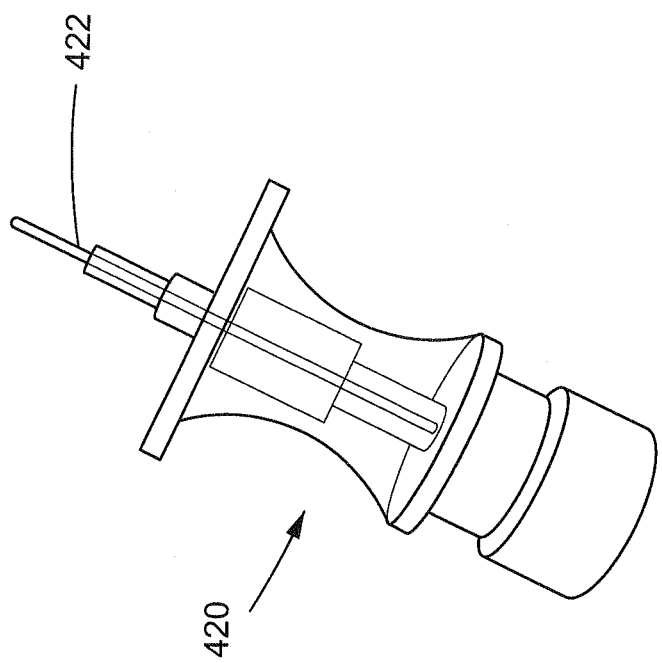
FIG. 12 is a perspective view of an exemplary vented fill cap, in accordance with certain aspects of the present invention.

FIG. 12 illustrates an exemplary vented fill cap 420. The vented fill cap 420 may include a spike 422 for inserting through an elastomeric septum 401 on the sealed final product vial 400 to provide fluid communication to an interior of the final product vial. FIG. 13 illustrates an exemplary opening 402 left in the septum 401 of a sealed final product vial 400 immediately following removal of the spike 422. The length of time that the spike 422 remains puncturing the septum of the final product vial 400 can have an impact on the length of time it takes the opening 402 in the elastomeric material to reset and reseal following removal of the vented fill cap 420 from the final product vial 400.

Figure 14:
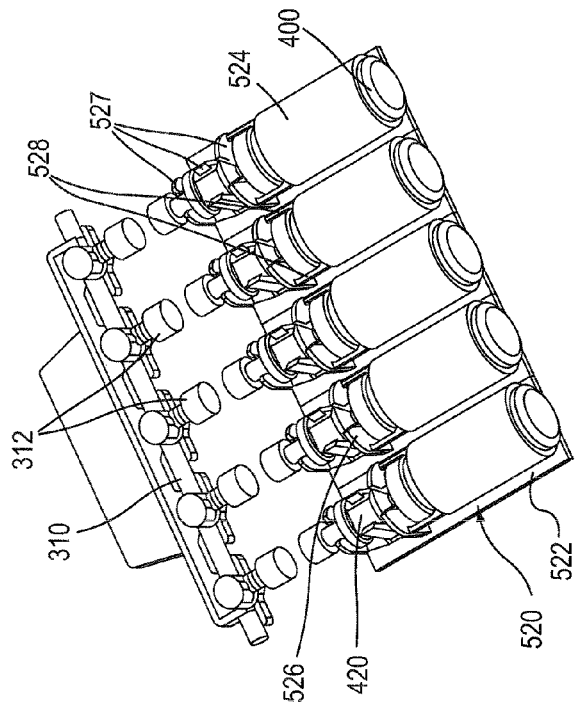
FIG. 14 is a perspective view of a packaging device for use with a vented fill cap and a vial, in accordance with certain aspects of the present invention.
Figure 15:
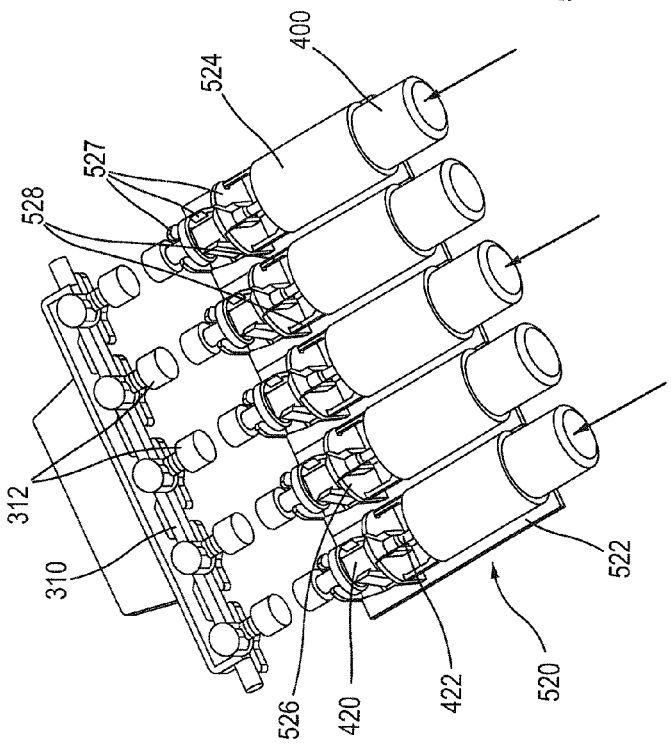
FIG. 15 is a perspective view of the packaging device of FIG. 14 shown in a position of use, in accordance with certain aspects of the present invention.

FIGS. 14 and 15 illustrate a packaging device 520 that may provide stability and protection for the vented fill caps 420 and the sealed final product vials 400 during shipping and handling of the kit 500. In addition, the packaging device 520 may provide an effective means for quickly and safely applying the vented fill caps 420 to the sealed final product vials 400 while still in the sterile packaging of the kit 500. Thus, the vented fill caps 420 may be applied just prior to use so that the amount of time that the spike 422 punctures the septum 401 of the vials 400 may be minimized. Although described herein with reference to the final product vial 400, the features described herein may also be used with the final product vial 405, the sterility vial 450, or any other vial suitable for connection to a fill cap.

As shown in FIG. 14, each packaging device 520 may include a base portion 522, which may be a generally flat substrate, for mounting a vial containment portion 524 and a fill cap retention portion 526. The illustrations in FIGS. 14 and 15 show five such packaging devices 520, which may be integrally connected on a single substrate material with perforations, for example, providing lines of demarcation for separation of one or more packaging devices 520, depending on the desired configuration of the system 10. The vial containment portion 524 may be formed to be an open cylinder for slidably receiving the final product vial 400 through an open end distal from the end nearest the fill cap retention portion 526. The vial containment portion 524 may have an inner diameter equal to or slightly smaller than the outer diameter of the final product vial 400 so that the vial 400 is substantially secured by a press fit arrangement with the vial containment portion 524. In accordance with other aspects of the present invention, any suitable retention device, such as internal tabs or an adhesive, may be used to secure the final product vial 400 in the vial containment portion 524. An internal detent (not shown) may be provided to prevent the final product vial 400 from sliding beyond a certain point into the vial containment portion 524 unless overcome by an application of force against the exposed lower end of the final product vial 400. Accordingly, the final product vial 400 may be secured in a predetermined position relative to the vented fill cap 420 and, in particular, the spike 422, during transport and handling of the kit 500. The fill cap retention portion 526 may include one or more cap retention devices 527, such as clips or clamps, for mounting and holding the vented fill cap 420 in a stable position against the base portion 522. As shown in FIG. 14, the vented fill cap 420 may be mounted in the fill cap retention portion 526 with the spike 422 shielded by an upper portion of the vial containment portion 524 to protect the kit 500 from puncture during transport and handling, as well as to protect a technician, for example, from injury during application of the vented fill cap 420 onto the sealed final product vial 400. The packaging device 520 thus maintains the spike 422 of the vented fill cap 420 protected and at a predetermined distance from the septum 401 of the final product vial 400 when in a storage configuration.

When ready for use, a technician may hold the packaging device 520, or apply pressure against the distal end of the vented fill cap 420, while applying an opposing pressure against the distal end of the final product vial 400. As shown by the arrows in FIG. 14, force is applied against the distal end of the final product vial 400 to overcome any retention forces as a result of detents and/or retention devices in order to slide the final product vial 400 toward the vented fill cap 420. Vial guides 528 may be provided to extend between the vial containment portion 524 and the fill cap retention portion 526. The vial containment portion 524 and vial guides 528 guide the final product vial 400 as it is pushed toward the vented fill cap 420 until the spike 422 pierces the septum 401. The packaging device 520 is designed to be easily accessible and actuated while remaining in the unopened sterile packaging of the kit 500. Thus, piercing of the vial septum 401 may be done just prior to opening the sterile packaging of the kit 500. As shown in FIG. 15, the final product vial 400 with the vented fill cap 420 attached may then be connected to one of the dispensing ports 312 of the manifold tube 310 for assembly into the system 10.

Figure 16:
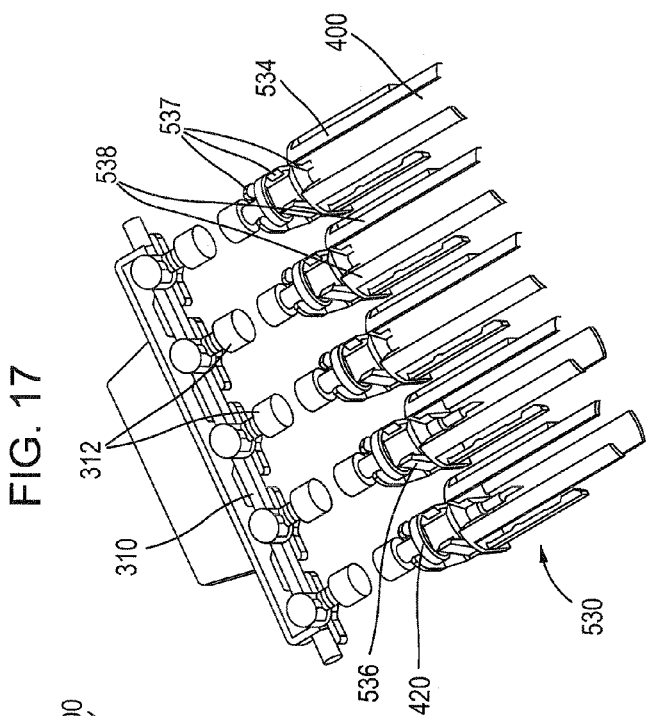
FIG. 16 is a perspective view of a packaging device for use with a vented fill cap and a vial, in accordance with certain aspects of the present invention.
Figure 17:
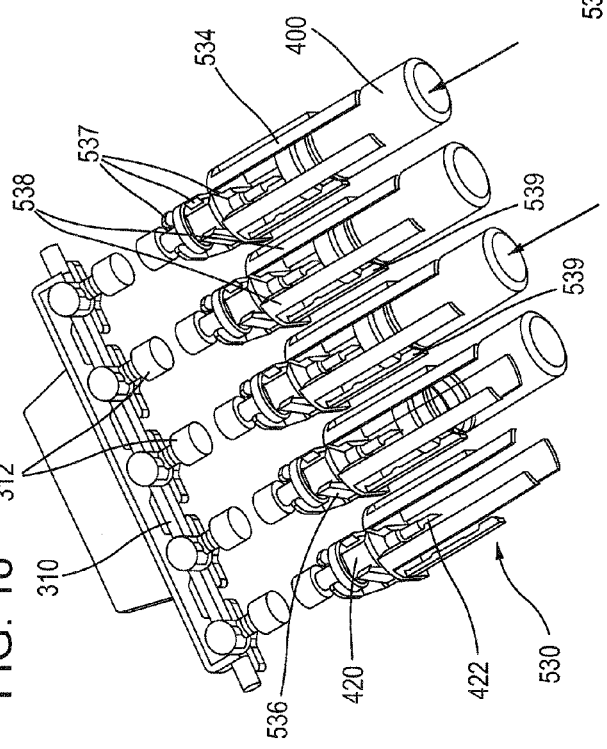
FIG. 17 is a perspective view of the packaging device of FIG. 16 shown in a position of use, in accordance with certain aspects of the present invention.

In accordance with yet other aspects of the present invention, FIGS. 16 and 17 illustrate a second packaging device 530 that may be used in the kit 500. As shown in FIG. 16, each packaging device 530 may include a vial containment portion 534 and a fill cap retention portion 536. The fill cap retention portion 536 may include one or more cap retention devices 537, such as clips or clamps, for mounting and holding the vented fill cap 420 in a stable position. The vial containment portion 534 may be a plurality of extension clips 538 integrally formed to extend from a lower portion of the fill cap retention portion 536. The extension clips 538 may be configured to extend circumferentially around the spike 422, wherein the distal ends of the extension clips 538 are configured to form a circle having an inner diameter equal to or slightly smaller than the outer diameter of the final product vial 400 so that the vial 400 is substantially secured by a press fit arrangement with the vial containment portion 534.

In accordance with other aspects of the present invention, any suitable retention device, including, as shown in FIG. 16, detent clips 539, may be provided to secure the final product vial 400 in the vial containment portion 534. The detent clips 539 may be formed to extend from the fill cap retention portion 536 and mate with a feature on the final product vial 400, such as a neck portion, for example. The detent clips 539 may also prevent the final product vial 400 from sliding beyond a certain point into the vial containment portion 534 unless overcome by an application of force against the exposed lower end of the final product vial 400. Thus, the final product vial 400 may be secured in a predetermined position relative to the vented fill cap 420 and, in particular, the spike 422, during transport and handling of the kit 500. In addition, the spike 422 may be shielded by the extension clips 538 and/or the detent clips 539 to protect the kit 500 from puncture during transport and handling as well as to protect a technician, for example, from injury during application of the vented fill cap 420 onto the sealed final product vial 400. The packaging device 530 maintains the spike 422 of the vented fill cap 420 protected and at a predetermined distance from the septum 401 of the final product vial 400 when in a storage configuration.

When ready for use, a technician may hold the packaging device 530, or apply pressure against the distal end of the vented fill cap 420, while applying an opposing pressure against the distal end of the final product vial 400. As shown by the arrows in the FIG. 16, force may be applied against the distal end of the final product vial 400 to overcome any retention forces as a result of detents and/or other retention devices in order to slide the final product vial 400 toward the vented fill cap 420. The extension clips 538 and/or detent clips 539 may serve to guide the final product vial 400 as it is pushed toward the vented fill cap 420 until the spike 422 pierces the septum 401. The packaging device 530 is designed to be easily accessible and actuated while remaining in the unopened sterile packaging of the kit 500. Thus, piercing of the vial septum 401 may be done just prior to opening the sterile packaging of the kit 500. As shown in FIG. 17, the final product vial 400 with the vented fill cap 420 attached is ready to be connected to one of the dispensing ports 312 of the manifold tube 310 for assembly into the system 10.

Figure 18:
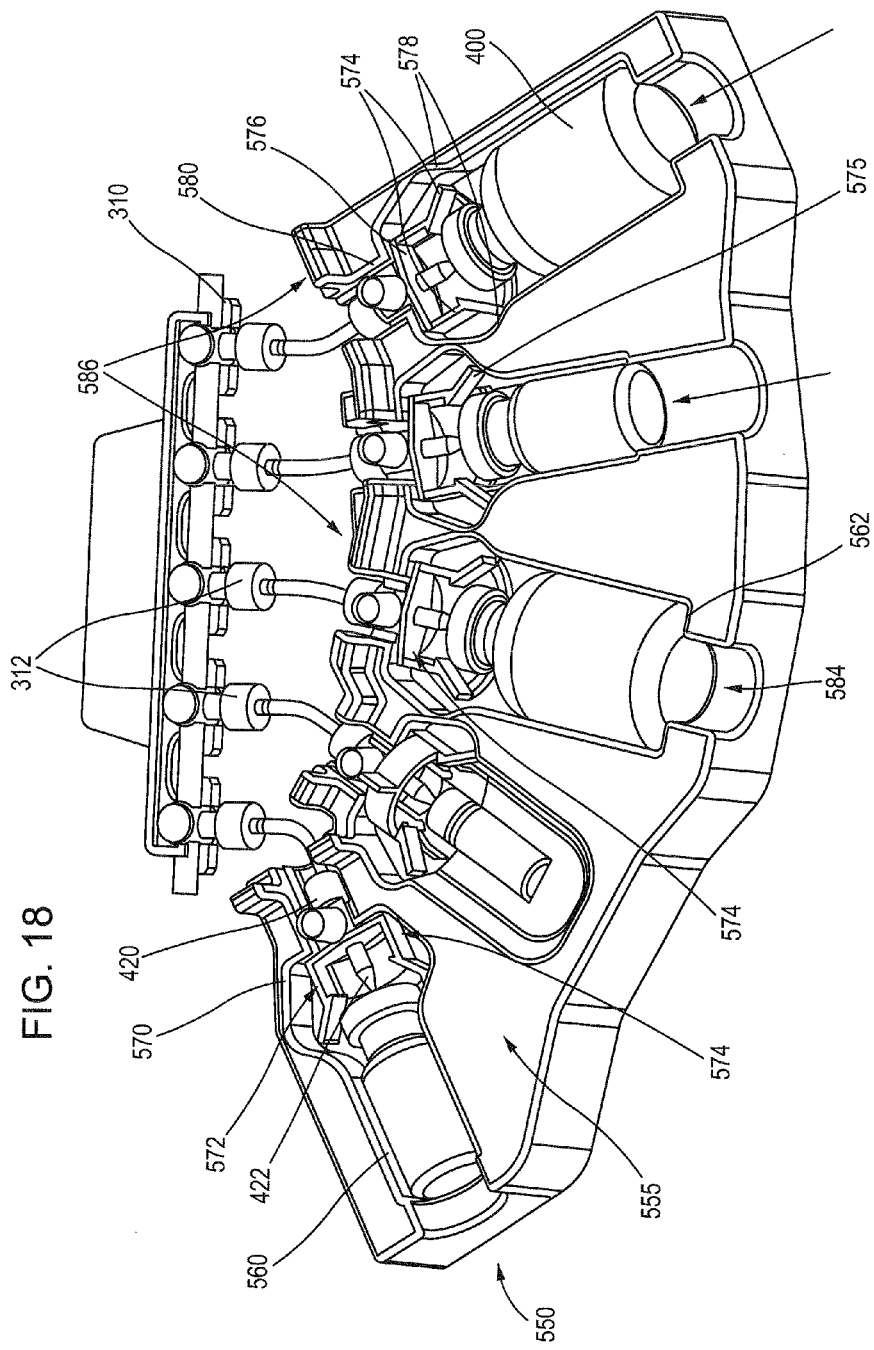
FIG. 18 is a perspective view of a packaging device for use with a vented fill cap and a vial, in accordance with certain aspects of the present invention.
Figure 19:
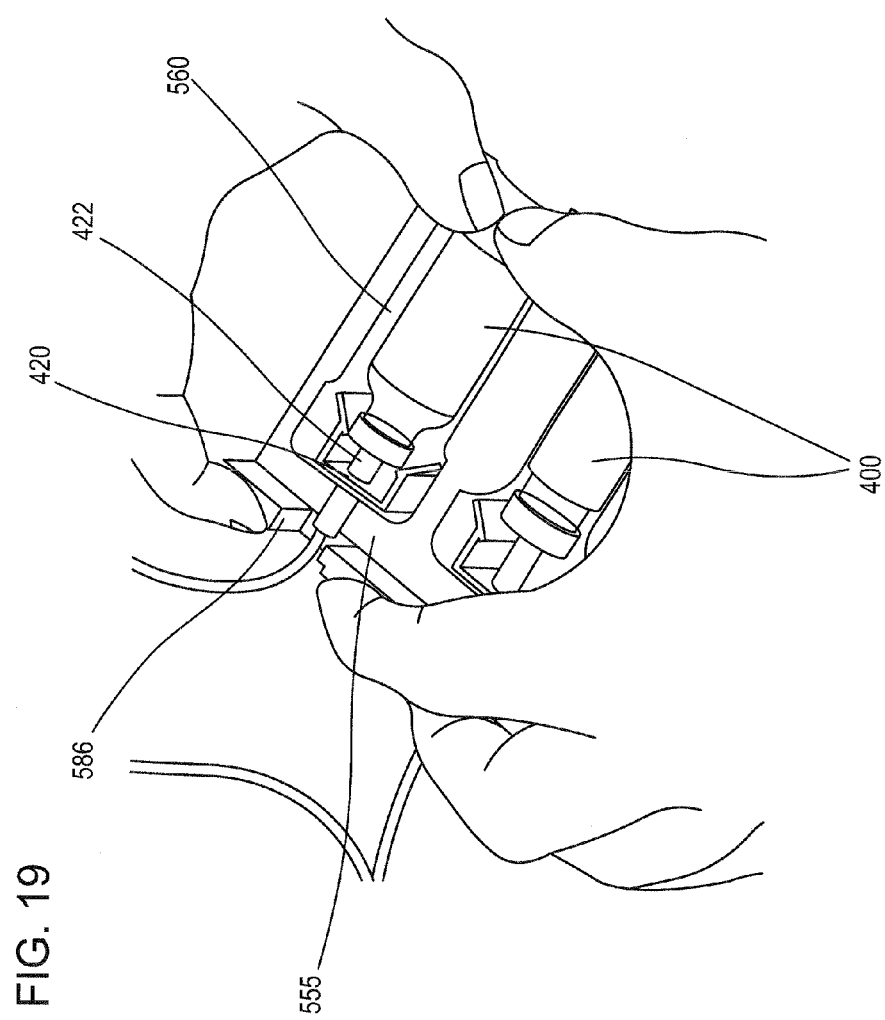
FIG. 19 is a perspective view of the packaging device of FIG. 18 in a state of use, in accordance with certain aspects of the present invention.
Figure 20:
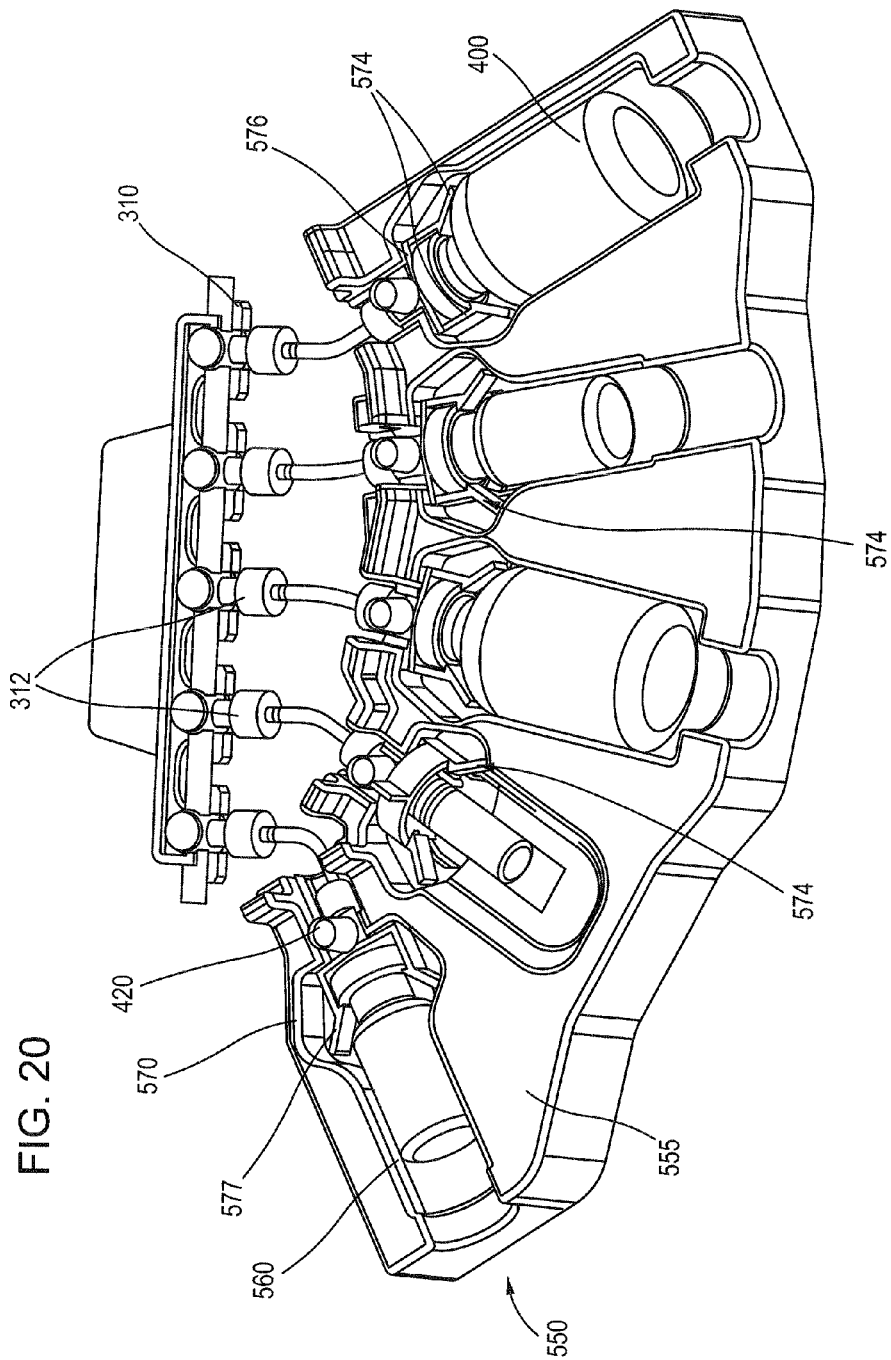
FIG. 20 is a perspective view of the packaging device of FIG. 18 shown in a position of use, in accordance with certain aspects of the present invention.

In accordance with yet other aspects of the present invention, FIGS. 18-20 illustrate another packaging device 550 that may be used in the kit 500. As shown in FIG. 18, the packaging device 550 may include a tray 555, which may be thermoformed from a plastic, or any other suitable material. The tray 555 may be formed to have one or more vial containment portions 560 and fill cap retention portions 570.

The fill cap retention portion 570 may be a cavity formed in the tray and shaped to house the vented fill cap 420 in a stable position. As shown in FIG. 18, the vented fill cap 420 may be provided with a cap retention means 572. The cap retention means 572 may be configured to slidably receive and retain the product vial 400 when the product vial 400 is physically forced towards the vented fill cap 420. The cap retention means 572 may include, for example, a plurality of cap retention arms 574 that extend from distal ends of a transverse cap retention member 576 toward the product vial 400 contained in the vial containment portion 560. The fill cap retention portion 570 of the tray 555 may be formed to have a wider transverse width than a transverse width of the vial containment portion 560. The cap retention arms 574 may be bent or flared toward a distal end so that the distal ends 575 of the cap retention arms 574 also have a wider transverse width than the transverse width of the vial containment portion 560. In this manner, the vented fill cap 420 may be securely housed in the fill cap retention portion 570 of the tray 555. The flared distal ends 575 of the cap retention arms 574 prevent any substantial movement of the fill cap 420 in a direction toward the product vial 400 by seating against a transitional surface 578 of the fill cap retention portion 570 where the fill cap retention portion 570 extends to be wider than the vial containment portion 560. Similarly, the transverse cap retention member 576 may be configured to have a width wider than an upper fill cap slot 580 formed in the tray 555. The transverse cap retention member 576 thus prevents from the vented fill cap 420 from substantial movement in a direction away from the product vial 400.

The vial containment portion 560 may be a partial-cylindrical cavity formed in the tray 555 to accept the product vial 400 in a press fit manner, for example, to secure the product vial 400 in the vial containment portion 560. A lower surface 562 of the vial containment portion may serve to seat the product vial 400 when in a storage position. In accordance with other aspects of the present invention, detents or other similar retention devices may be provided, for example, to extend from the inner cylindrical wall of the vial containment portion 560 to prevent the product vial 400 from any substantial movement in the direction of the vented fill cap 420 during transport and/or handling. The final product vial 400 may thus be prevented from sliding beyond a certain point into the vial containment portion 570 unless overcome by an application of force against the exposed lower end of the final product vial 400. The final product vial 400 is thus secured in a predetermined position relative to the vented fill cap 420 and, in particular, the spike 422, during transport and handling of the kit 500.

As shown in FIG. 18, the spike 422 may extend from a central portion of the retention member 576 to be positioned above the septum of the product vial 400. Because the product vial 400 and the vented fill cap 420 are secured as described above, the spike 422 may be shielded by the retention arms 574 and the configuration of the tray 555 to protect the kit 500 from puncture during transport and handling, as well as to protect a technician, for example, from injury during application of the vented fill cap 420 onto the sealed final product vial 400. The packaging device 550 maintains the spike 422 of the vented fill cap 420 protected and at a predetermined distance from the septum 401 of the final product vial 400 when in a storage configuration.

In accordance with another aspect of the present invention, the tray 555 may be configured to have a lower slot 584 extending away from the lower surface 562 of the vial containment portion 560. The slot 584 may be sized to allow a technician to insert a finger into the slot 584 for applying a force against the bottom surface of the product vial 400.

When ready for use, a technician may hold the tray 555 of the packaging device 550 while applying pressure against the distal end of the final product vial 400. As shown by the arrows in FIG. 18, force may be applied against the distal end of the final product vial 400, for example, by use of one or more thumbs or fingers in the slot 584, to overcome any retention forces as a result of the press fits, detents and/or other retention devices in order to slide the final product vial 400 toward the vented fill cap 420. Support ribs 586 may be provided to extend from the tray 555 to improve the ergonomic use and stabilization of the tray 555 during the application of force.

As shown in FIG. 19, with the tray 555 resting on a flat surface, a technician may use one or more thumbs, for example, to apply force against the distal end of the final product vial 400 while stabilizing the tray 555 with one or more fingers placed on the support ribs 586. The support ribs 586 may thus allow a more natural squeezing motion by the technician while the final product vial 400 is pushed through the vial retention containment portion 560 toward the vented fill cap 420 until the spike 422 pierces the septum and the vented fill cap 420 is secured to the product vial 400.

As shown in FIG. 20, in accordance with another aspect of the present invention, the cap retention arms 574 may be provided with a securing mechanism 577, such as a snap fit feature, to mate with a feature of the product vial 400, such as a cap, to further secure the product vial 400 to the vented fill cap 420 during removal of the product vials 400 from the tray 555. Features such as small ribs, for example, may also be incorporated into the tray 555 to retain the vials 400 and spikes 422 in the tray 555 should the packaging device 550 be inverted or otherwise subjected to severe movements.

The packaging device 550 is designed to be easily accessible and actuated while remaining in the unopened sterile packaging of the kit 500. Thus, piercing of the vial septum 401 may be done just prior to opening the sterile packaging of the kit 500. As shown in FIG. 20, the final product vials 400 with the vented fill caps 420 attached and connected to the dispensing ports 312 of the manifold tube 310 are ready for assembly into the system 10.

Figure 21:
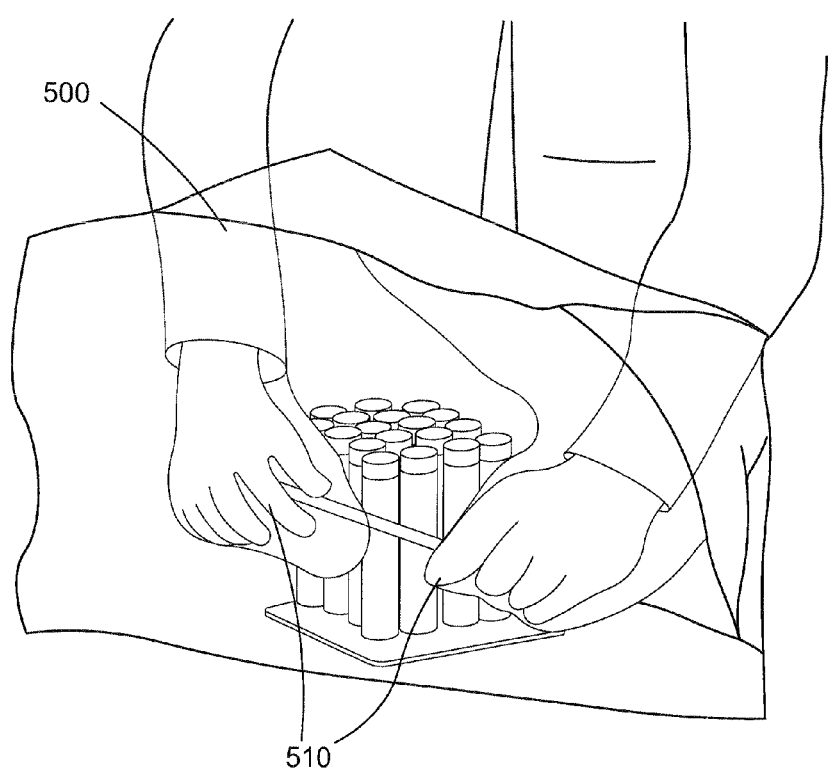
FIG. 21 is a perspective view of a sterile packaging of a sterile kit of disposable elements for use in a closed path vial fill system, in accordance with certain aspects of the present invention.

In accordance with another aspect of the present invention, as shown in FIG. 21, the sterile packaging of the kit 500 may be formed of a flexible, transparent material and with at least one integrated mitt 510 to allow access to the kit components without opening the packaging. The sterile packaging of the kit 500 may be configured to provide ample interior room when expanded to allow a technician to easily maneuver and manipulate the components inside the packaging without removing the components from the sterile kit environment.

FIG. 22 illustrates a vial fill process in accordance with aspects of the present invention. Once the radiopharmaceutical compound 110 has been mixed with the sterile dilution solution from the dilution container 260, by way of reverse (i.e., counterclockwise) operation of the peristaltic pump 200, as described previously, and with the valves 265 and 280 closed to the dilution container 260 and the pressurized gas line 275, the first valve 320 associated with the first final product vial 400 may be opened. In this manner, a closed path may be established to provide fluid communication from the interior of the bulk product vial 100 to the interior of the first final product vial 400. The stepper motor 250 may then be controlled to operate the pump 200 in a forward (i.e., clockwise) direction in order to draw radiopharmaceutical product from the bulk product vial 100 and push the product through the tube element 210, through the sterilization filter 270, through the dispensing port 312 associated with the first final product vial 400, and into the first final product vial 400. The amount of product to be dispensed in each vial 400 may be input through a software interface that is part of the control system 700, for example. In accordance with another aspect of the present invention, the technician may observe a fill amount in the vial 400 and manually control the pump and/or valves to provide the desired amount. Once the desired amount of the radiopharmaceutical compound is filled in the first vial 400, the associated valve 320 may be closed. If another dosage of the radiopharmaceutical is desired, the fill process may be repeated for each successive vial 400 attached to a dispensing port 312.

Figure 23:
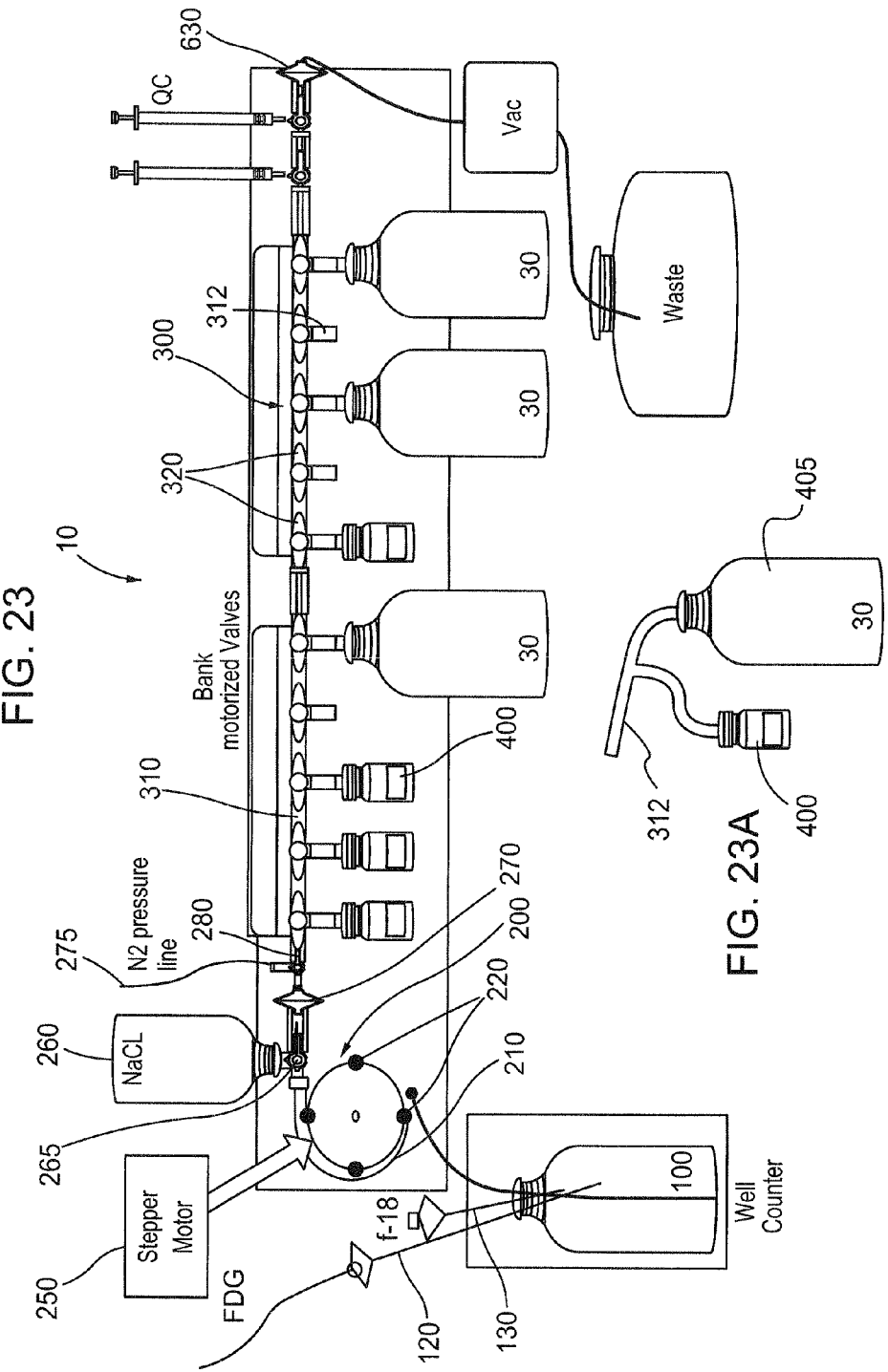
FIG. 23 is another illustration of the closed path vial fill system of FIG. 1, in which multiple vial sizes are used, in accordance with certain aspects of the present invention.

FIG. 23 illustrates the ease with which different size vials may be used with the system 10. For example, if the final product vial 400 is a standard 10 ml vial, a 30 ml final product vial 405 may be attached to an appropriate dispensing port 312 for depositing a larger amount of the radiopharmaceutical. In this manner, the system 10 may be used to fill one or more vials of the same size and/or one or more vials of differing sizes. According to another aspect of the invention, as shown in FIG. 23A, the connector tubes 412 may be pre-formed to provide a branched connection to more than one final product vial of differing sizes, 400 and 405, for example. A technician may then select which size final product vial is to be used with each corresponding dispensing port 312 and remove the unnecessary final product vial 400 or 405 associated with that dispensing port 312. When assembling the components in an aseptic environment, as described below, a technician may use thermal scissors, for example, to cut one of the branches and provide a closed fluid path to the correct size final product vial 400 or 405.

Figure 24:
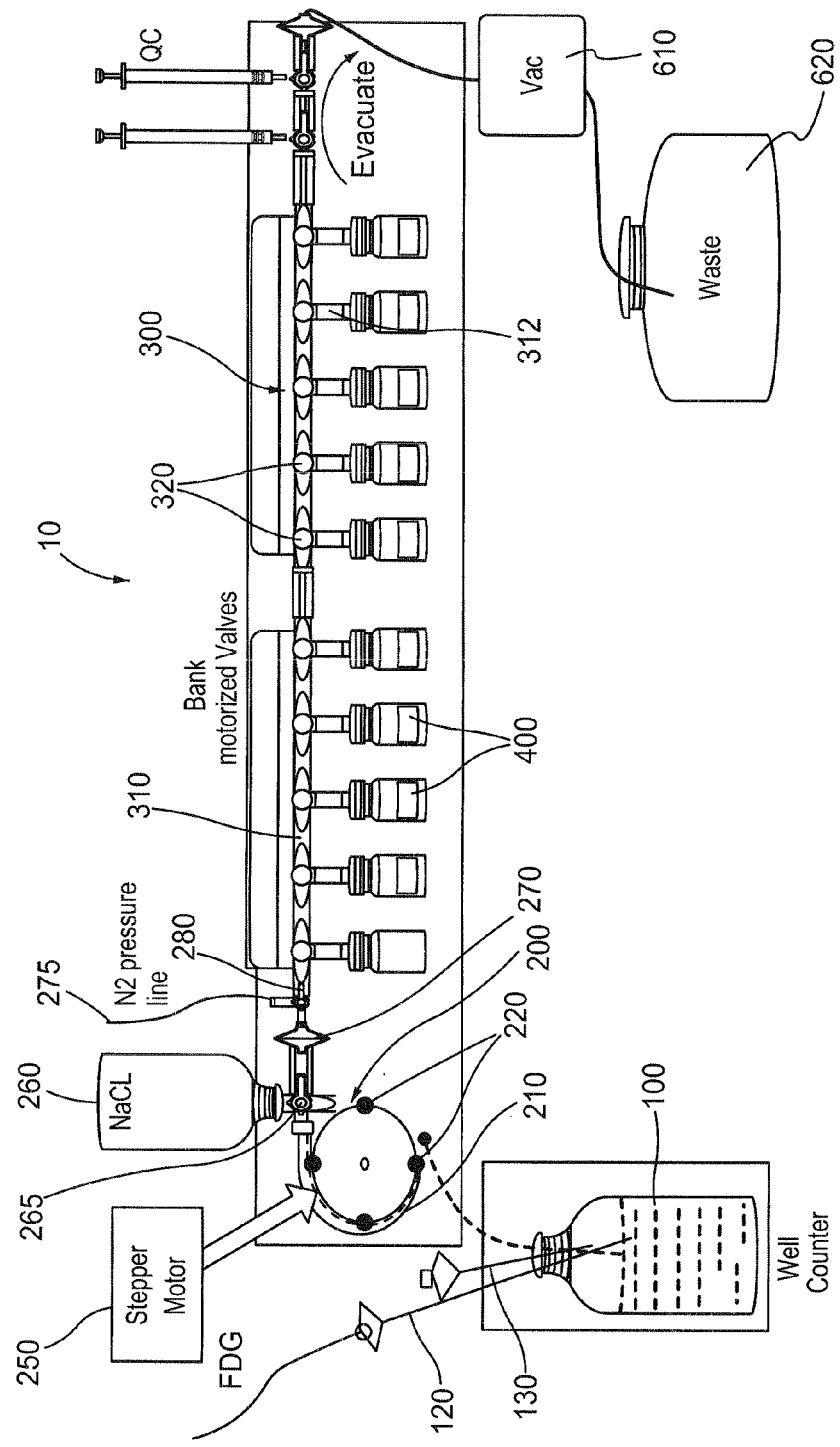
FIG. 24 is an illustration of a vial evacuation procedure in accordance with certain aspects of the closed path vial fill system of FIG. 1.

In accordance with another aspect of the invention, if vented fill caps 420 are not being used, for example, each vial 400 or 405 may be evacuated prior to being filled. The vacuum pump 610 may be used to apply a vacuum pressure to the interior of each of the vials 400. Because the system is a closed system, opening the valve 320 associated with a particular vial 400, as shown in FIG. 24 with respect to the tenth vial 400 (from closest to the pump 200 to farthest), and operating the vacuum pump 610 will evacuate the air from the interior of the vial 400. Closing the valve 320 and sequentially performing the same operation may evacuate the interior of each vial 400 as well as the interior of the closed path through to the pump 200, which may be locked to prevent rotation by way of the negative pressure. Thus, the fill process may be enhanced and the vials filled without the need to provide a separate venting means.

Figure 25:
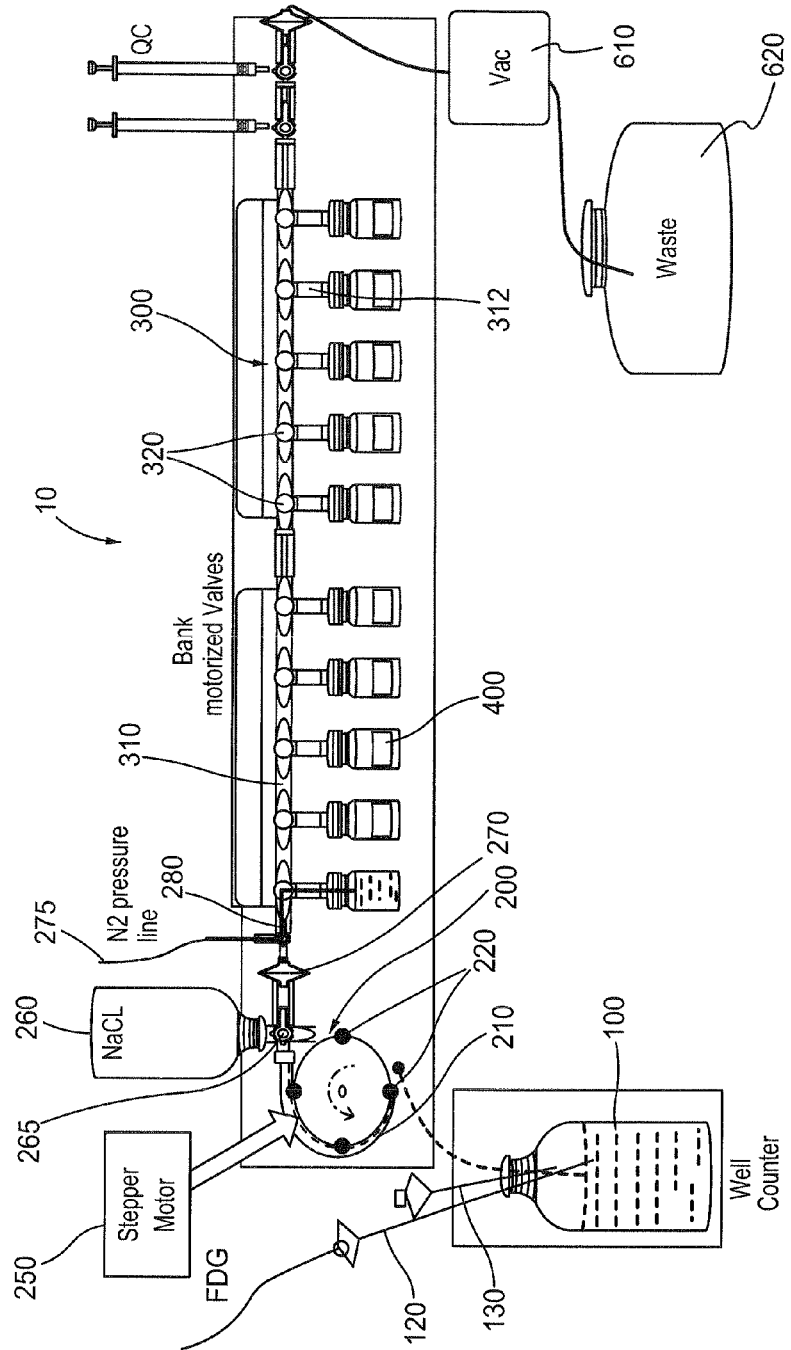
FIG. 25 is an illustration of a vial pressurization procedure in accordance with certain aspects of the closed path vial fill system of FIG. 1.

Furthermore, another aspect according to the present invention includes using the pressured gas line 275 to create a positive pressure in the interior of the vial 400 after the vial 400 is filled with a radiopharmaceutical compound. As shown in FIG. 25, for example, the valve 280 may be opened while the valve 320 to the filled vial 400 remains open. Thus, the pressured gas may flow into the vial 400. A positive pressure may be created in the vial 400 so that when the vial 400 is removed from the system 10, which may be by pulling the vial 400 off of the dispensing port 312, the positive internal pressure will prevent any foreign contaminants from entering the interior of the vial 400.

Figure 26:
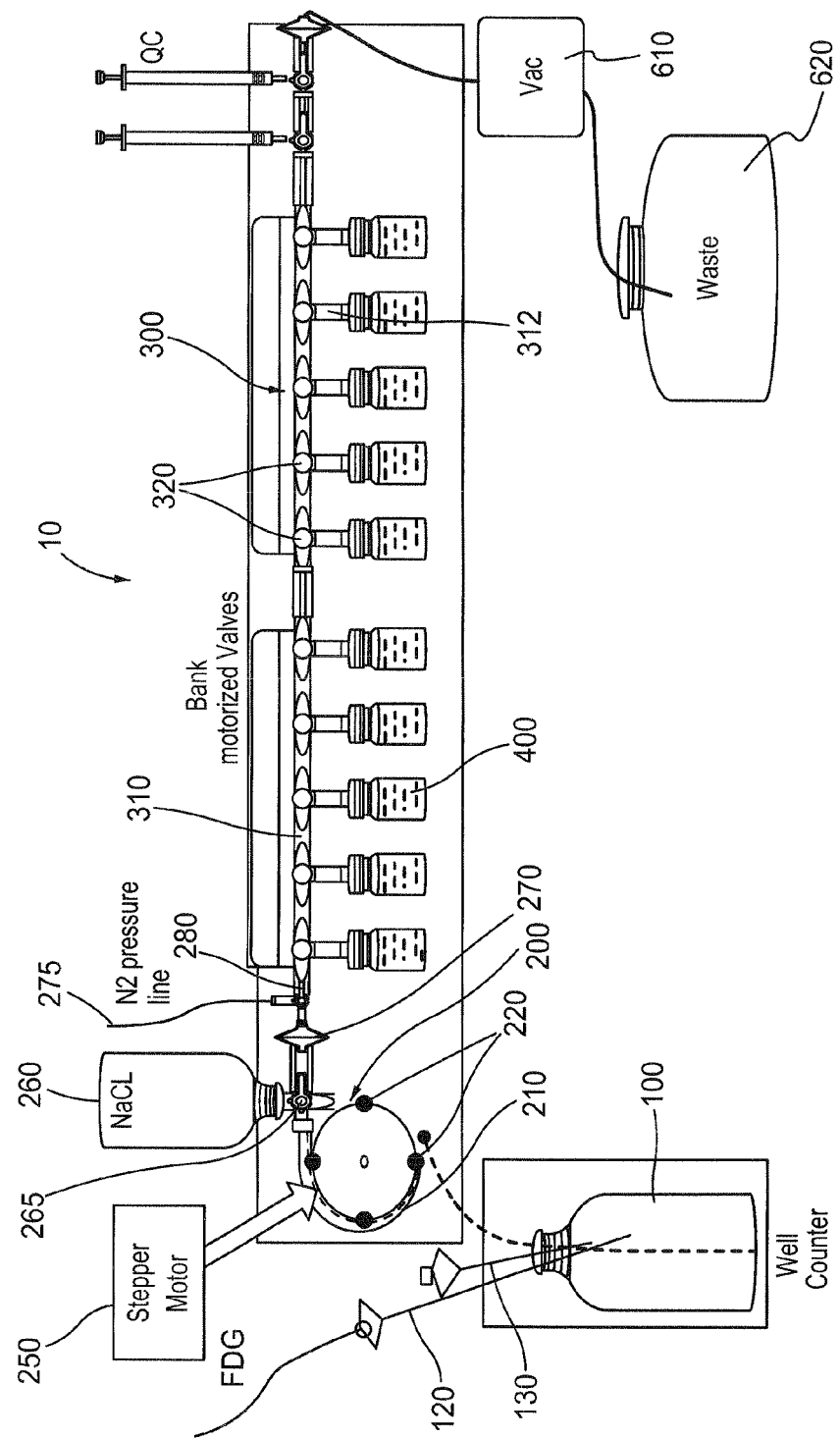
FIG. 26 is another illustration of the closed path vial fill system of FIG. 1, wherein the vials are each filled, in accordance with certain aspects of the present invention.
Figure 27:
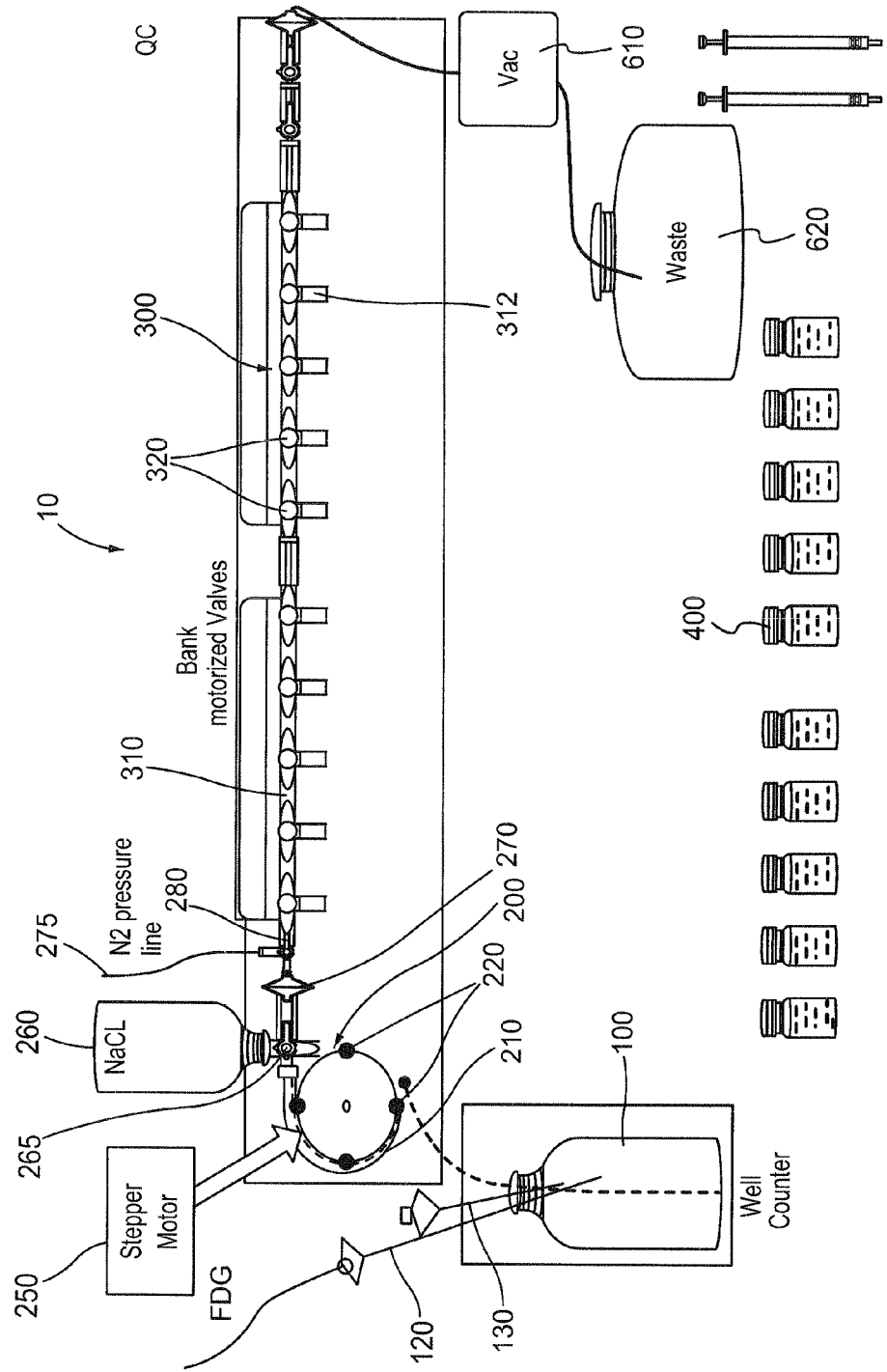
FIG. 27 is another illustration of the closed path vial fill system of FIG. 1, wherein the vials are released from the dispensing manifolds, in accordance with certain aspects of the present invention.

The process disclosed above may be continued until all of the vials 400, for example, are filled, as shown in FIG. 26. The filled vials 400 may then be removed from the system, as shown in FIG. 27, by manual or automated means, for subsequent delivery in shielded vial containers to a practitioner for use in an imaging procedure, for example.

Figure 28:
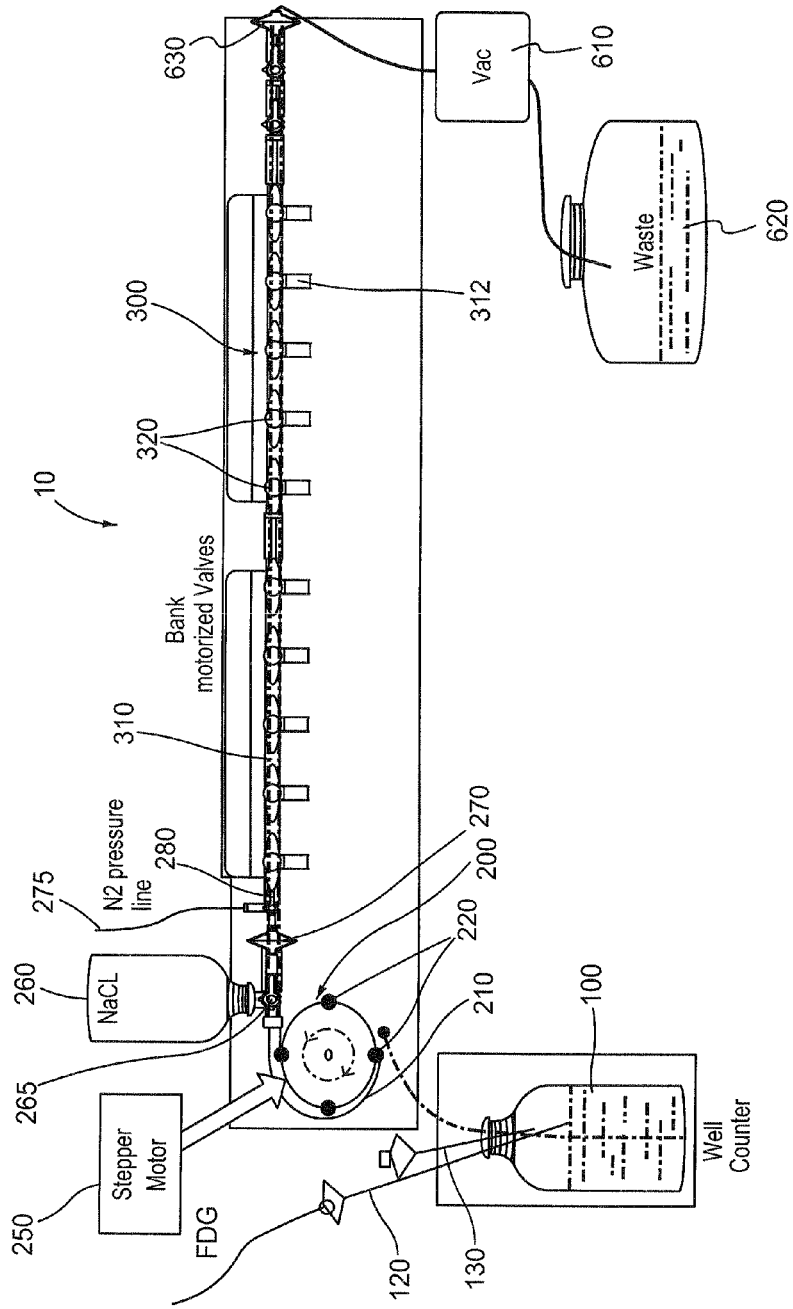
FIG. 28 is an illustration of a system flushing process in accordance with certain aspects of the closed path vial fill system of FIG. 1.

FIG. 28 illustrates a process in which the disposable portions of the system 10 may be flushed once the vials 400 have been released for use. For example, valve 265 may be opened and the stepper motor 250 operated to run the pump 200 in reverse so that any remaining dilution solution may flush through the tube element 210 and into the bulk product vial 100. The valve 265 may then be closed, the stepper motor 250 operated to run in forward, and/or the vacuum pump 610 turned on to create a suction force in order to complete the flushing by pulling the flush solution from the bulk product vial 100, and pushing/pulling the flush solution through the tube element 210, the filter 270, the manifold tubes 310, the second filter 630, and into a waste receptacle 620. Thus, much of the residual radioactivity may be effectively removed from the disposable elements, further protecting the technicians from exposure during the removal and/or replacement of the disposable elements. The waste receptacle 620 may be provided in a separately shielded enclosure for removal and disposition.

Figure 29:
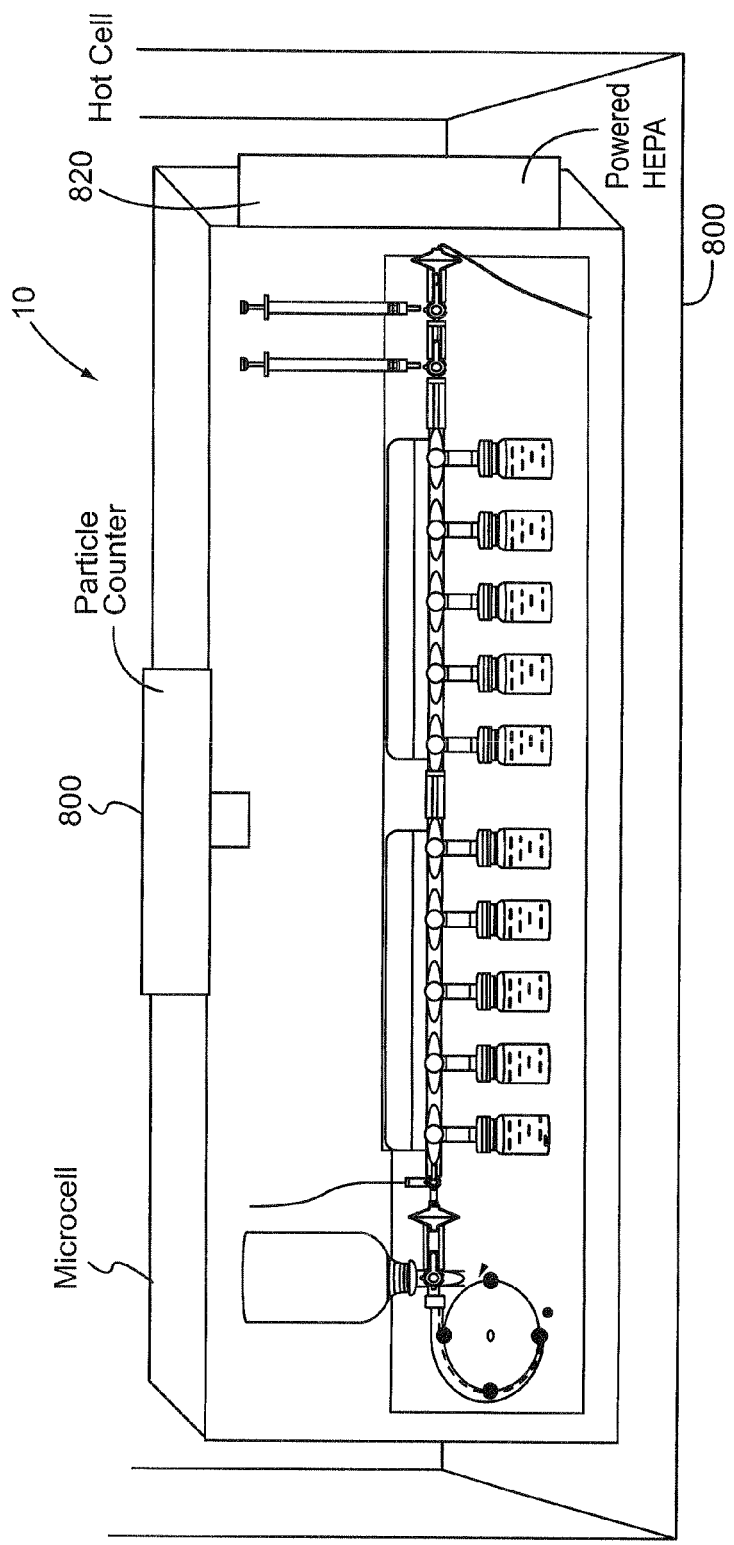
FIG. 29 is an illustration of a closed path vial fill system in a shielded enclosure, in accordance with certain aspects of the present invention.

FIG. 29 illustrates the closed fill vial system 10 as it may be provided in a shielded, or "hot cell" environment. To protect the technicians compounding and preparing the radiopharmaceuticals for distribution, the closed fill vial system 10 may be provided as a microcell structure in the interior of a hot cell 800, which may be a lead lined enclosure, for example. Although the closed fill vial system 10 will protect the radiopharmaceutical from contamination during dispensing, a particle counter 810 and/or an air filter 820 may also be provided to further monitor and provide a clean air environment within the hot cell 800.

As disclosed above, aspects of the dispensing operation may be controlled by manually turning on and off the pump 200, and manually controlling the valves 320, for example. Each vial 400 may be provided with an amount of the dispensed product via visual observation. However, as discussed above, an exemplary closed fill vial system 10 may include a control system 700 to provide automation to the closed fill vial system 10, further reducing the need of a technician, for example, to be physically engaged with the system 10 at times when the radionuclide may be most active.

Figure 30:
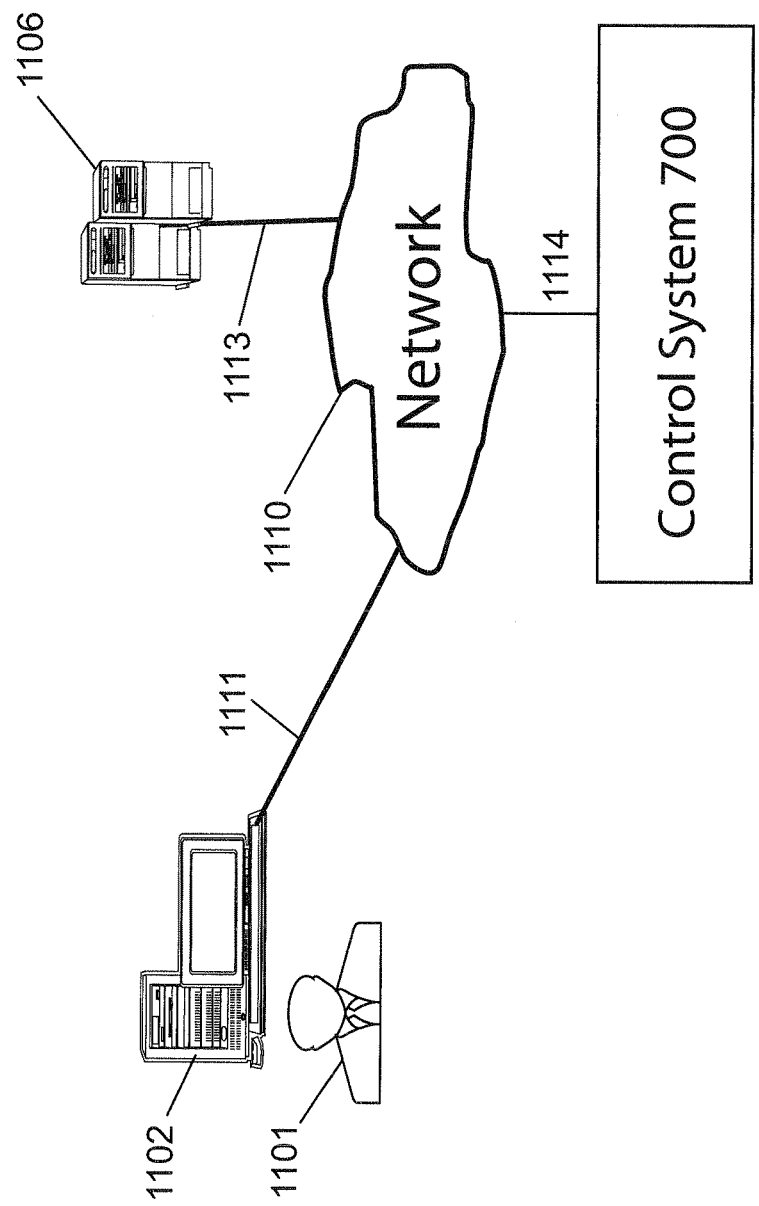
FIG. 30 shows various features of an example computer system for use in conjunction with aspects of a closed path vial fill system, in accordance with aspects of the present invention.

FIG. 30 shows various features of an example computer system for use in conjunction with aspects of the control system 700 of the present invention. Although computer monitoring and/or control of the vial filling process, or the in-situ filter integrity testing, for example, may be automated, the computer system may also be accessed by a user 1101 to control and/or access the equipment comprising the closed fill vial system 10, input or access data to control and/or monitor various parameter, monitor status of the equipment and/or process, and/or to perform other steps or acts in accordance with aspects of the present invention, such as by using software and other computer features located on a server or other network device 1106. Access occurs, for example, via a terminal 1102, network (e.g., the Internet) 1110, and couplings 1111, 1113. Access to the control equipment of the system 10, for example, may occur via coupling 1114. The terminal 1102 may comprise, for example, a personal computer (PC), minicomputer, mainframe computer, microcomputer, telephone device, personal digital assistant (PDA), or other device having a processor and input capability. The server 1106 may comprise, for example, a PC, minicomputer, mainframe computer, microcomputer, or other device having a processor and a repository for data or that is capable of accessing a repository of data. Couplings 1111, 1113 and 1114 may include wired, wireless, or fiberoptic links.

Figure 31:
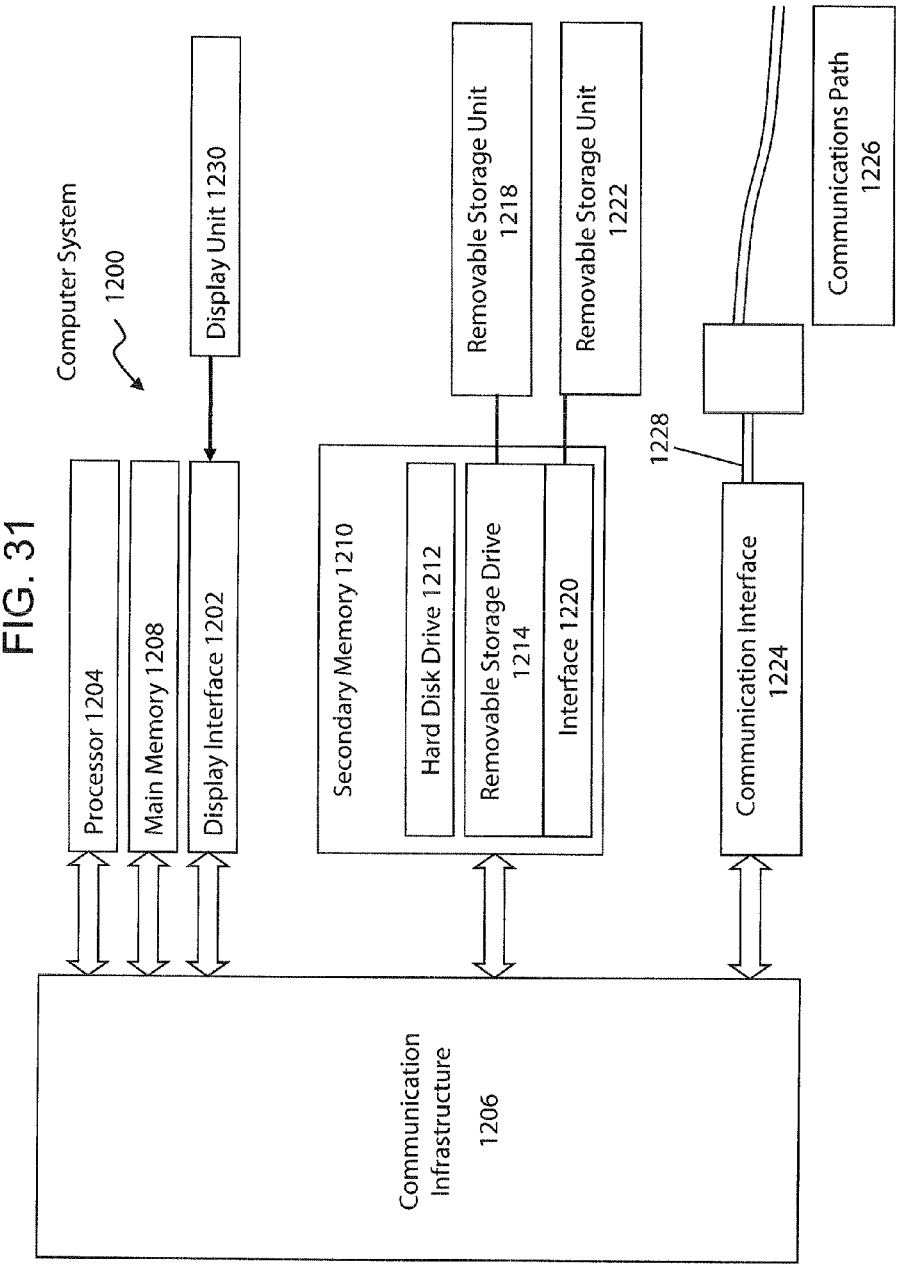
FIG. 31 shows an exemplary flow diagram of various functions performed in a system and method for controlling aspects of a closed path vial fill system, in accordance with aspects of the present invention.

Aspects of the present invention may be implemented using hardware, software or a combination thereof and may be implemented in one or more computer systems or other processing systems. In one variation, the invention is directed toward one or more computer systems capable of carrying out the functionality described herein. An example of such a computer system 1200 is shown in FIG. 31.

Computer system 1200 includes one or more processors, such as processor 1204. The processor 1204 is connected to a communication infrastructure 1206 (e.g., a communications bus, cross-over bar, or network). Various software variations are described in terms of this exemplary computer system. After reading this description, it will become apparent to a person skilled in the relevant art(s) how to implement aspects of the invention using other computer systems and/or architectures.

Computer system 1200 can include a display interface 1202 that forwards graphics, text, and other data from the communication infrastructure 1206 (or from a frame buffer not shown) for display on the display unit 1230. Computer system 1200 also includes a main memory 1208, preferably random access memory (RAM), and may also include a secondary memory 1210. The secondary memory 1210 may include, for example, a hard disk drive 1212 and/or a removable storage drive 1214, representing a floppy disk drive, a magnetic tape drive, an optical disk drive, etc. The removable storage drive 1214 reads from and/or writes to a removable storage unit 1218 in a well-known manner. Removable storage unit 1218, represents a floppy disk, magnetic tape, optical disk, etc., which is read by and written to removable storage drive 1214. As will be appreciated, the removable storage unit 1218 includes a computer usable storage medium having stored therein computer software and/or data.

In alternative variations, secondary memory 1210 may include other similar devices for allowing computer programs or other instructions to be loaded into computer system 1200. Such devices may include, for example, a removable storage unit 1222 and an interface 1220. Examples of such may include a program cartridge and cartridge interface (such as that found in video game devices), a removable memory chip (such as an erasable programmable read only memory (EPROM), or programmable read only memory (PROM)) and associated socket, and other removable storage units 1222 and interfaces 1220, which allow software and data to be transferred from the removable storage unit 1222 to computer system 1200.

Computer system 1200 may also include a communications interface 1224. Communications interface 1224 allows software and data to be transferred between computer system 1200 and external devices. Examples of communications interface 1224 may include a modem, a network interface (such as an Ethernet card), a communications port, a Personal Computer Memory Card International Association (PCMCIA) slot and card, etc. Software and data transferred via communications interface 1224 are in the form of signals 1228, which may be electronic, electromagnetic, optical or other signals capable of being received by communications interface 1224. These signals 1228 are provided to communications interface 1224 via a communications path (e.g., channel) 1226. This path 1226 carries signals 1228 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1214, a hard disk installed in hard disk drive 1212, and signals 1228. These computer program products provide software to the computer system 1200. Aspects of the invention are directed to such computer program products.

Computer programs (also referred to as computer control logic) are stored in main memory 1208 and/or secondary memory 1210. Computer programs may also be received via communications interface 1224. Such computer programs, when executed, enable the computer system 1200 to perform the features of the present invention, as discussed herein. In particular, the computer programs, when executed, enable the processor 1204 to perform aspects of the present invention via the control system 700. Accordingly, such computer programs represent controllers of the computer system 1200.

In a variation where aspects of the invention are implemented using software, the software may be stored in a computer program product and loaded into computer system 1200 using removable storage drive 1214, hard drive 1212, or communications interface 1224. The control logic (software), when executed by the processor 1204, causes the processor 1204 to perform various aspects of the invention as described herein. In another variation, aspects of the invention are implemented primarily in hardware using, for example, hardware components, such as application specific integrated circuits (ASICs). Implementation of the hardware state machine so as to perform the functions described herein will be apparent to persons skilled in the relevant art(s).

Figure 32:
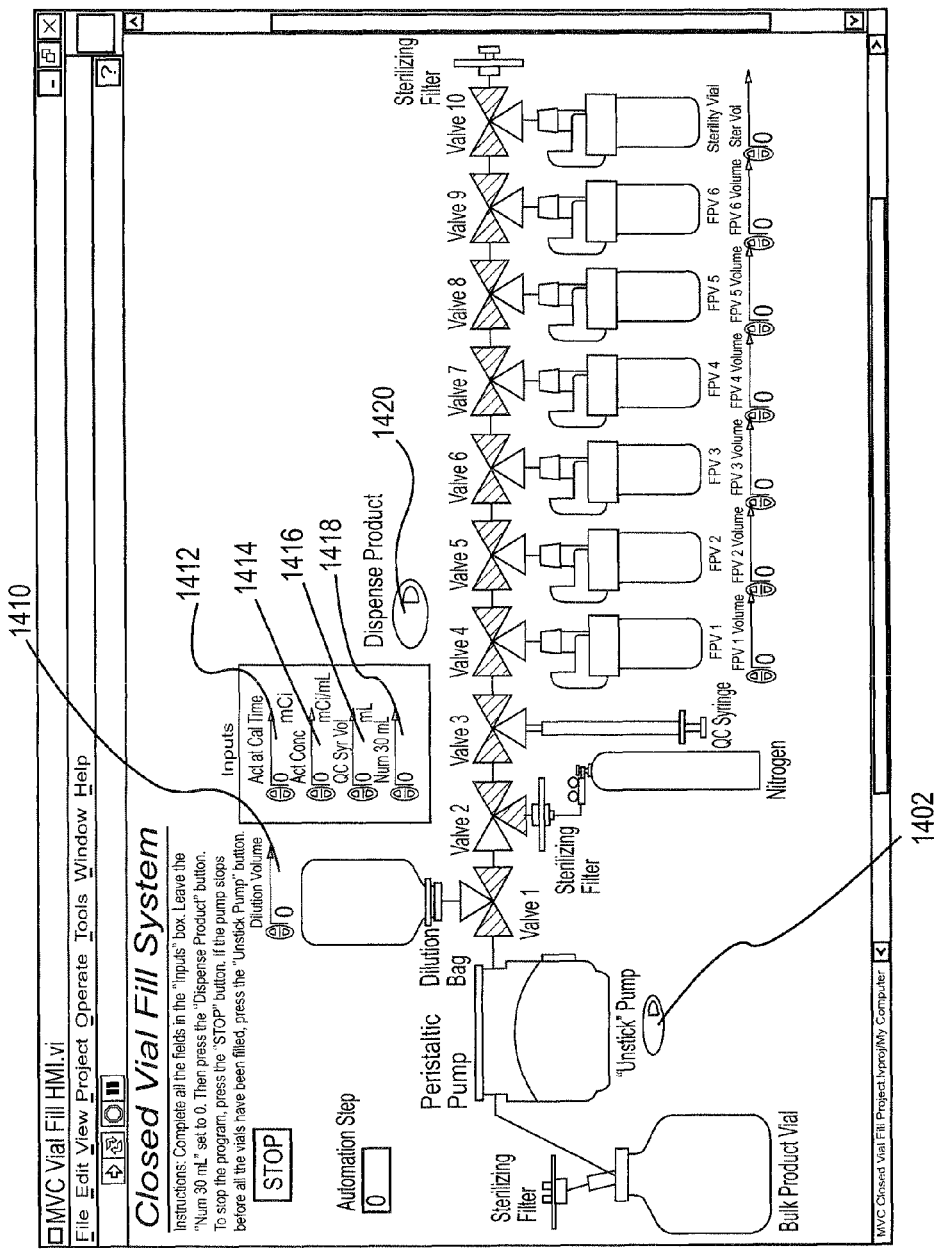
FIG. 32 is an exemplary screenshot of a software interface for automated control of various functions of a closed path vial fill system, in accordance with aspects of the present invention.

FIG. 32 is an exemplary wireframe diagram of a display page for a software interface that may be used, for example, with the computer system 1200 described above, in accordance with aspects of the present invention. The software may be developed as part of the control system 700 for the closed fill vial system 10, and once validated, may be access controlled and monitored to ensure the integrity of the manufacturing process when implemented via the software interface. As shown in FIG. 32, the software interface may provide a graphical depiction of various aspects of the system and a real-time view of various settings, parameters, and functional attributes. Various user interface feedback mechanisms for operation and control of the closed fill vial system 10 may be provided. For example, an "unstick" pump pushbutton control 1402 may be provided. If the user selects the control 1402, by clicking on the graphical display of the button with the mouse cursor, for example, the control system 700 may send a signal to the pump 200 to temporarily alternate between operating in a forward direction and operating in a reverse direction to unlock what may appear to be a locked pump 200. Various inputs may be provided to ensure the proper dosage of a radionuclide in the final product vial 400 to be delivered for use in a procedure. For example, the user may input the dilution volume 1410 of the dilution container 260, which may be a certain number of mL of sterile water, for example. Another input may include, Activity at Calibration Time 1412, which is the amount of radionuclide activity, measured in millicuries (mCi), that must be available in the bulk product vial 100 at some future time, perhaps five (5) hours later, to ensure a proper radionuclide level will be available for dilution and distribution, recognizing that the half-life of the radionuclide may be 110 minutes. Thus, by knowing the Activity at Calibration Time 1412 may provide the system a mechanism for determining an initial amount of radionuclide product to be deposited in the bulk product vial 100. Another input may include Activity Concentration 1414, which is the desired amount of radionuclide activity for a particular volume of product to be delivered in a particular dose (mCi/mL). Thus, if the goal is 20 mCi/mL, for example, for a particular dosage, and the radiopharmaceutical product 110 initially delivered to the bulk product vial 100 measures 5000 mCi/17 mL, the product may be diluted to achieve the desired result, taking into account the Activity at Calibration Time discussed above. Other inputs may include a QC Syringe Volume 1416, which may provided the amount of product to be delivered to a quality check syringe or vial, and a Number of 30 mL vials 1418, for example, to calibrate the amount of final radiopharmaceutical product that must be produced and distributed. Once all of the inputs are entered, the user may activate the control system 700 to automatically run the entire fill sequence from beginning to end, for example, by using the cursor to click on a Dispense Product control 1420. Although described herein as being used to automate the entire system 10, the software interface and control system 700 may be configured to provide single use control of various functions of the system 10, such as activation of a fill sequence for a single final product vial 400 or a sterility vial 450, for example.

Figure 33:
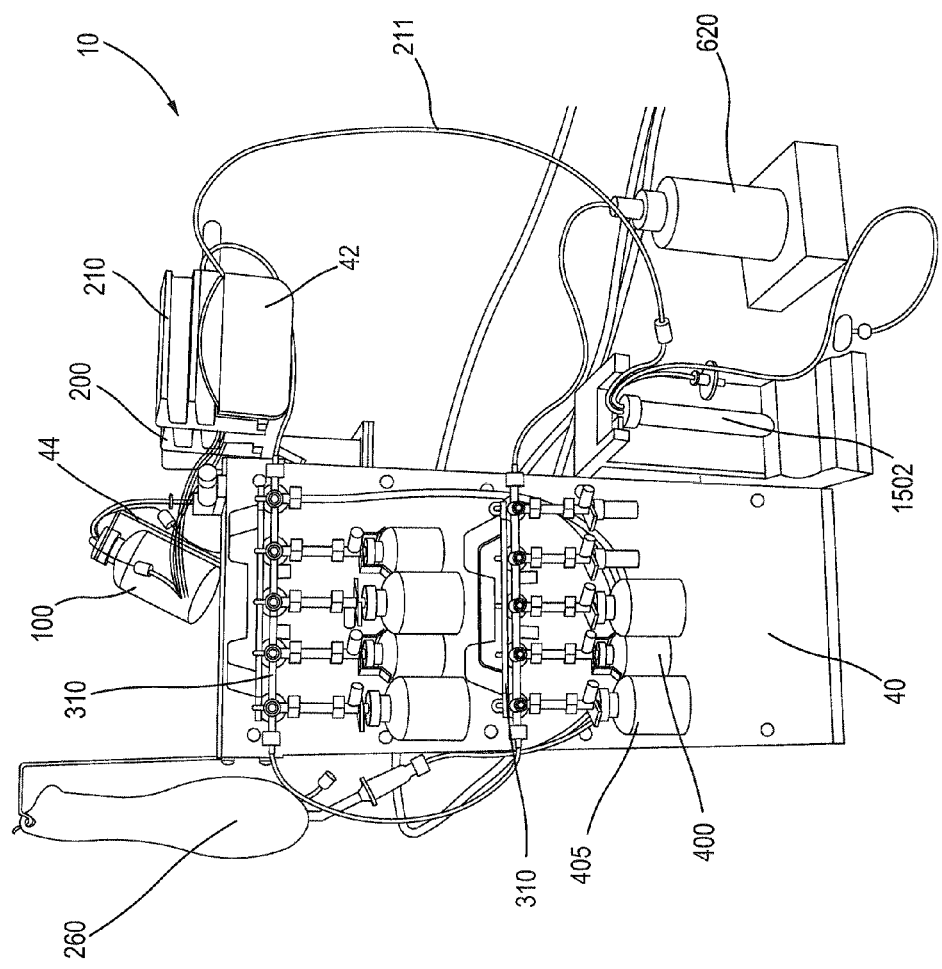
FIG. 33 shows an exemplary closed path vial fill system incorporating a CAV sensor, in accordance with certain aspects of the present invention.
Figure 34:
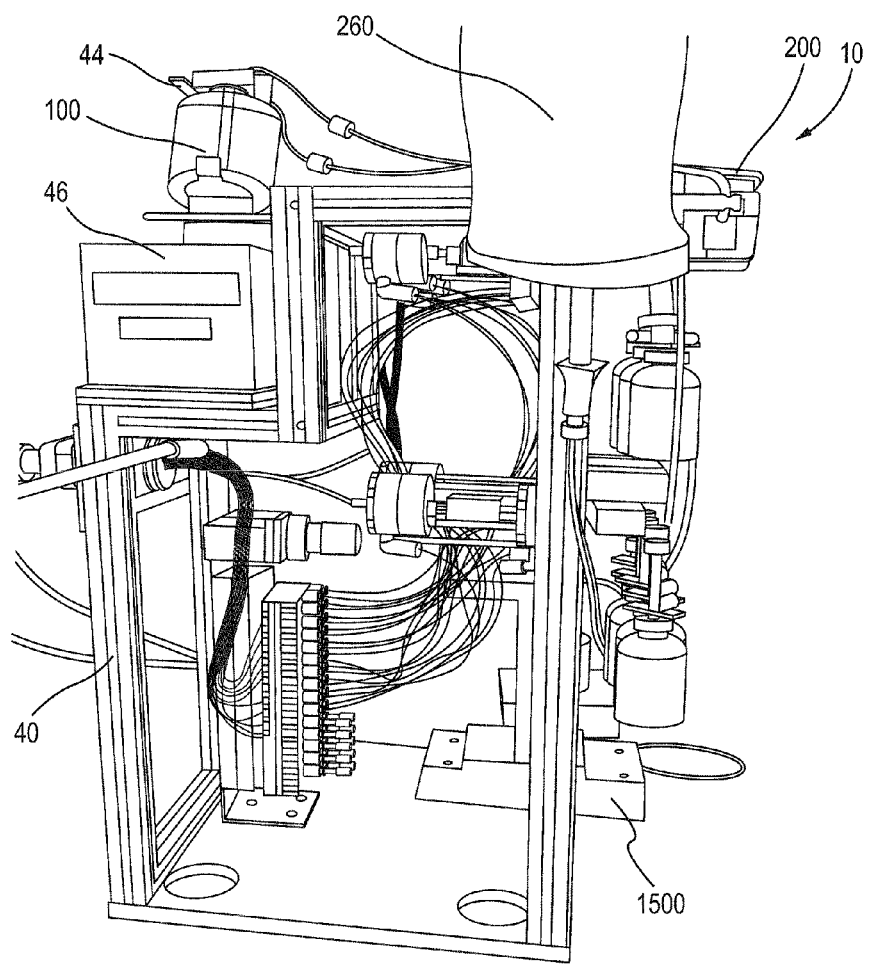
FIG. 34 is a side view of the exemplary closed path vial fill system of FIG. 33, in accordance with certain aspects of the present invention.

In accordance with yet other aspects of the present invention, as shown in FIGS. 33 and 34, the frame 40 of the system 10 may be configured to incorporate the manifold tubes 310 in a vertical arrangement and may include a pump mounting bracket 42 for mounting one or more peristaltic pumps 200. A vial bracket 44 may be attached to the frame 40 for mounting the bulk product vial 100 to the system 10.

Figure 35:
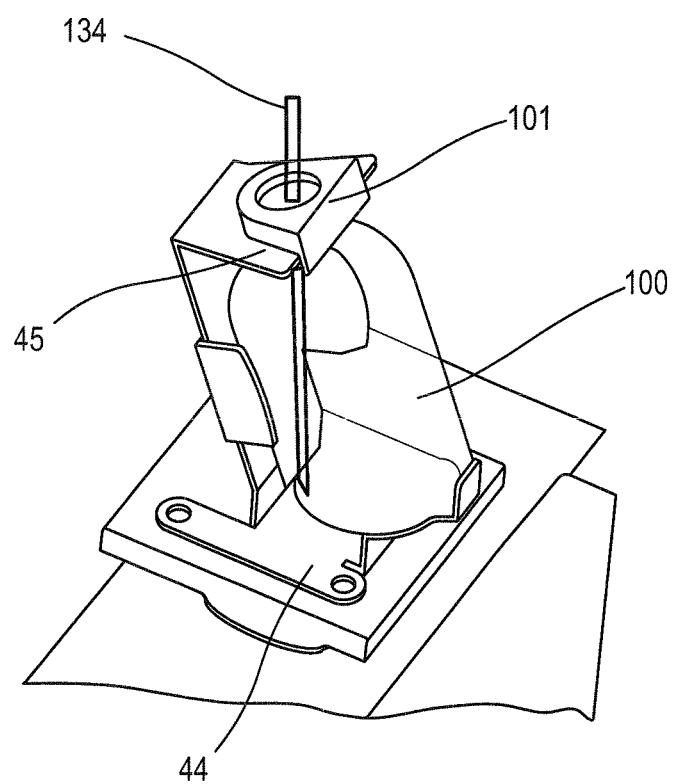
FIG. 35 is an illustration of a bracket for mounting a bulk product vial, in accordance with certain aspects of the present invention.

FIG. 35 illustrates another view of an exemplary vial bracket 44. The vial bracket 44 may be configured to seat the bulk product vial 100 at an angle and have an orienting feature 45 for mating with an orienting feature 101 of the bulk product vial 100, such as a specifically configured top or a fitting for the top, for example, to quickly and efficiently allow a technician to align and seat the bulk product vial 100 in the vial bracket 44 according to a specific orientation. The bulk product vial 100 may be provided with an aspirating needle 144 or a dip tube, for example, configured to have an opening positioned at or near the lowest internal point of the tilted bulk product vial 100. The angle of the bulk product vial 100 and the specific orientation of the aspirating needle or dip tube, may thus work with gravity to ensure withdrawal of substantially the entire product contained in the bulk product vial 100.

Figure 36:
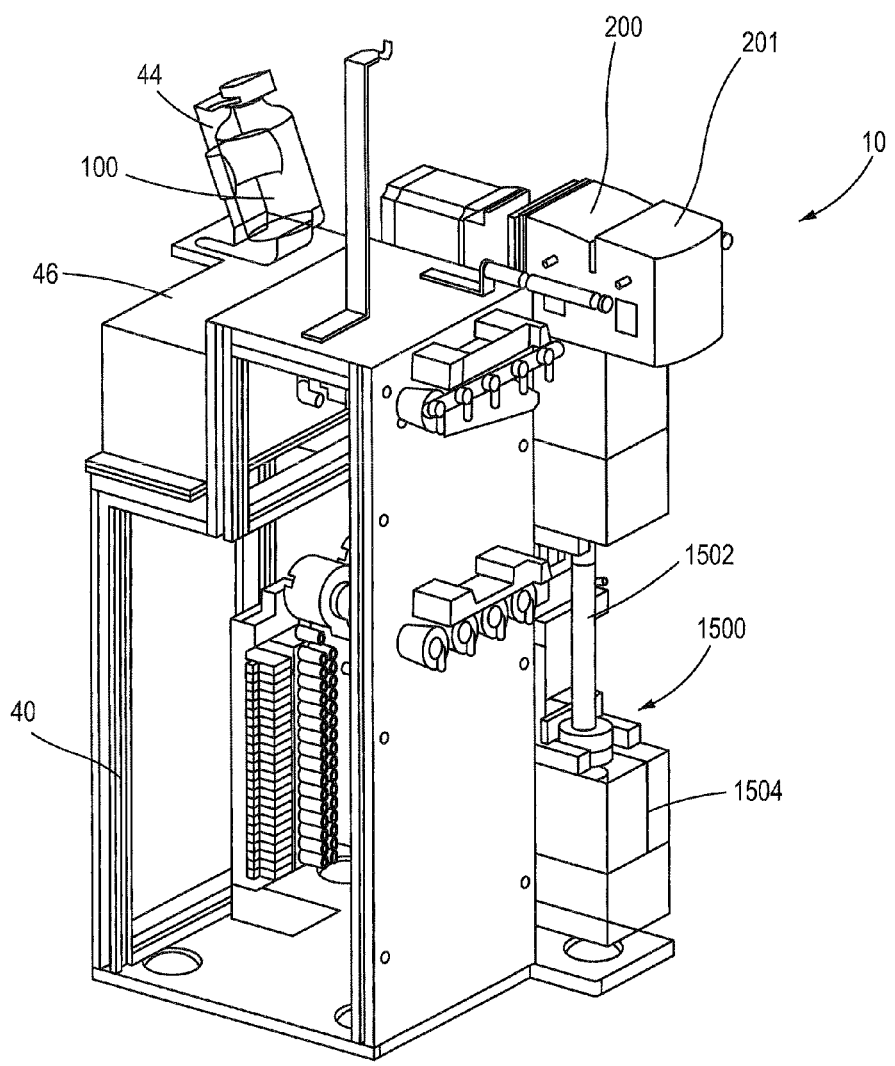
FIG. 36 is another illustration of an exemplary closed path vial fill system incorporating a CAV sensor, in accordance with certain aspects of the present invention.

In accordance with yet another aspect of the present invention, as shown in FIG. 36, the vial bracket 44 may be incorporated onto a precision scale 46 for mounting the bulk product vial 100 while providing the ability to measure a precise volume of product received into the bulk product vial 100. For example, in order to calibrate the peristaltic pump 200, the pump 200 may be operated to draw a certain amount of a dilution solution from the dilution container 260 and pump the dilution solution into the bulk product vial 100. By knowing the specific gravity of the dilution solution, and by measuring the mass of the solution delivered into the bulk product vial 100 using the precision scale 46, the volume of delivered solution can be derived and compared to the expected volume delivered for a certain number of revolutions of the stepper motor 250 for a tube of known internal dimensions. The precision scale 46 may thus be used to calibrate the pump 200 to compensate for varying flow characteristics that may occur during different runs of the system 10.

For example, slight differences in the internal diameters of the peristaltic tubing used in the disposable assemblies of the system 10 may result in a different volume of product being processed through the peristaltic pump 200 for the same number of revolutions of the stepper motor 250. Calibration of the pump 200, as described above, may thus provide a means for correcting or adjusting the baseline data in order to permit a more precise metering of the product into, for example, the final product vials 400 and 405.

As shown in FIG. 36, the system 10 may incorporate a concentration, activity, and volume (CAV) sensor 1500, similar to the CAV sensor described in U.S. Provisional Patent Application No. 61/508,402 entitled "Radiopharmaceutical CZT Sensor and Apparatus", filed Jul. 15, 2011, the entirety of which is incorporated herein by reference. The CAV sensor 1500 is an apparatus for detecting radionuclide content and activity in a volume of material. The CAV sensor 1500 may include a CAV container 1502 for receiving the radiopharmaceutical product 110 directly from the chemistry synthesis unit (CSU), for example, and at least one gamma ray detector 1504. As shown in FIG. 33, the CAV container 1502 (shown apart from the full CAV sensor 1500) may be connected to the bulk product vial 100 by way of a tube element 211. The tube element 211 provides fluid communication between the interior of the CAV container 1502 and the interior of the bulk product vial 100 and may be routed through a second peristaltic pump 201 for controlling a fluid flow in the tube element 211.

The CAV sensor 1500 may determine the volume, activity and concentration of the radiopharmaceutical product 110 received into the CAV container 1502. The information from the CAV sensor 1500 may be automatically provided to the control system 700, or the information may be read from the CAV sensor 1500 by a technician, for example, and manually input into the control system 700 prior to initiation of the automated vial fill process.

Figure 37:
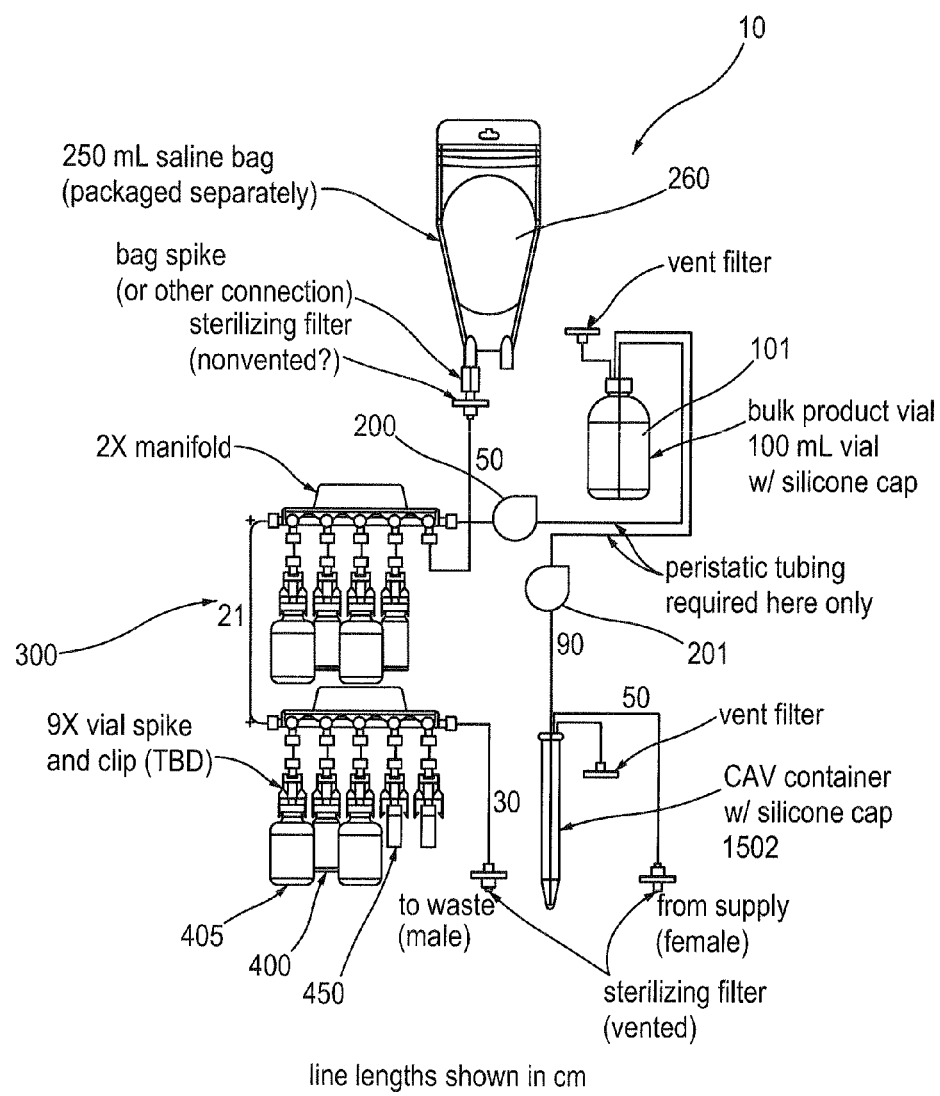
FIG. 37 is a schematic of an exemplary closed path vial system incorporating a CAV sensor, in accordance with certain aspects of the present invention.

FIG. 37 is a schematic to further illustrate a closed vial fill system 10 incorporating a CAV sensor 1500. The radiopharmaceutical product 110 may be delivered from the synthesizing unit directly to the CAV container 1502. The CAV sensor 1500 records the concentration, activity, and/or volume components of the radiopharmaceutical product 110. Once the desired parameters have been measured by the CAV sensor 1500, the peristaltic pump 201 may be used to draw the entire volume of the radiopharmaceutical product 110 from the CAV container 1502 for deposit into the bulk product vial 100. As described above in detail, the peristaltic pump 200 may then be used to draw a dilution solution from the dilution container 260 to dilute the radiopharmaceutical product 110 to desired levels of concentration and activity in accordance with the measurements recorded by the CAV sensor 1500. The diluted product may then be used to fill the final product vials 400, 405, the sterility vial 450, and/or the quality check syringes, for example, as pre-programmed in the control system 700.

FIGS. 38-65 are a series of schematic diagrams to illustrate exemplary aspects of a closed vial fill system 10 incorporating a CAV sensor 1500, a single peristaltic pump 200, and a method of using the closed vial fill system 10 in conjunction with a computer system 1200 for user control of the control system 700. The illustration discussed hereinafter begins once the disposable components of the system 10 have been installed as described previously.

To begin, a user may be required to logon to the computer system 1200 in order to gain access to the control system 700. Once the user successfully enters the user's login information, the user may be requested to select a particular closed vial fill system 10, if multiple systems may be used in conjunction for different runs of a radiopharmaceutical product. For example, the user may be requested to select either Unit 1 or Unit 2. The user selects which unit to use and may be prompted to indicate that the disposable components have been successfully installed for that particular unit. If the user confirms the installation of the disposable components onto the system 10, the user may begin the process of automated fill by choosing to first calibrate the pump.

Figure 38:
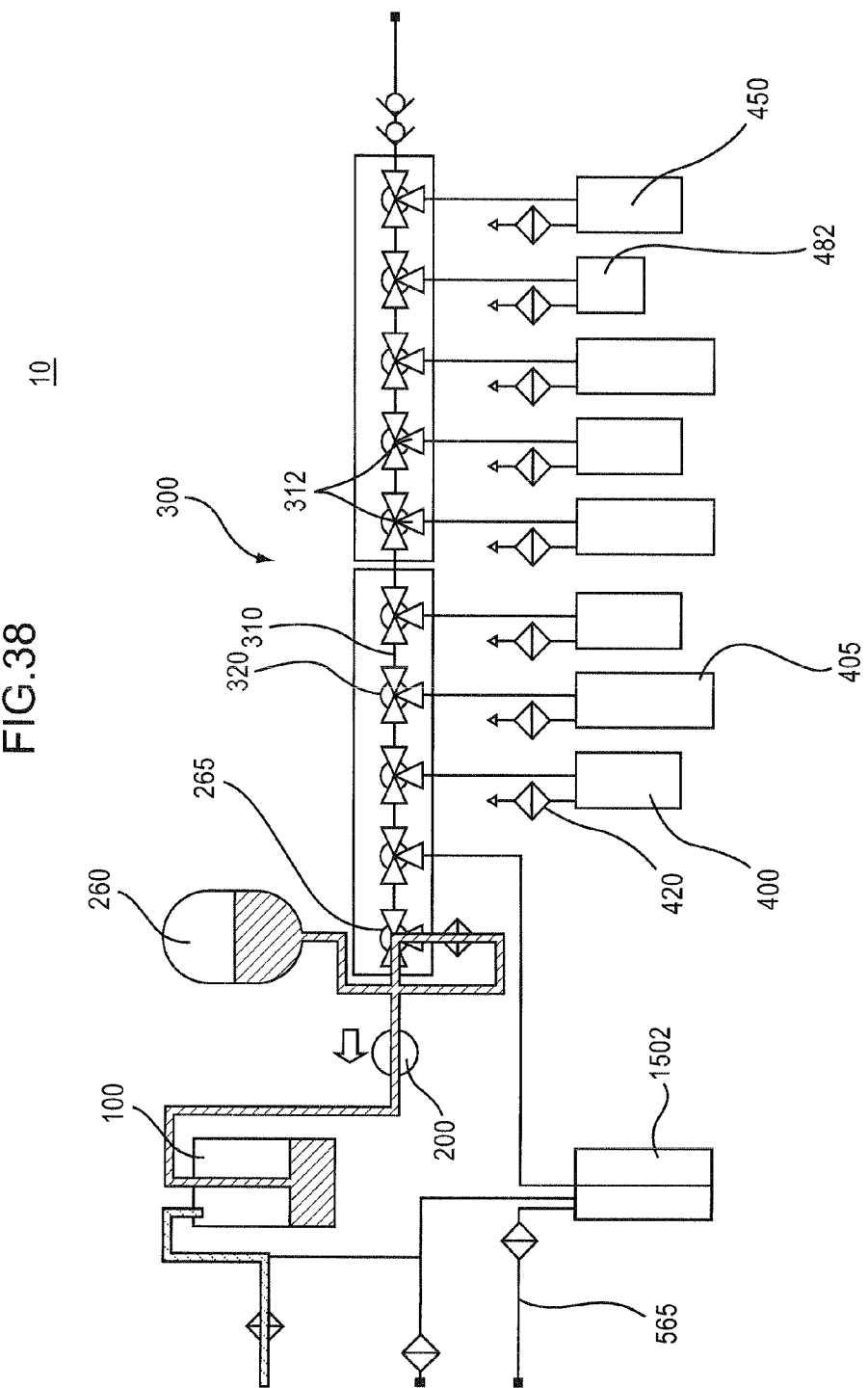
FIG. 38 is a schematic diagram to illustrate exemplary aspects of a closed vial fill system incorporating a CAV sensor and a method of using the closed vial fill system, in accordance with certain aspects of the present invention.

As shown in FIG. 38, when the user selects to calibrate the pump, the peristaltic pump 200 may be controlled to operate in a counterclockwise direction, for example, to pull a predetermined amount of dilution solution from the dilution container 260. The dilution container 260 may be integrated into the system 10, preferably between the peristaltic pump 200 and the dispensing manifold assembly 300, by way of the valve 265. The valve 265 may be a three-port solenoid valve, a diverter valve, or a stopcock valve, for example, and provide closed fluid communication between the peristaltic pump 200 and the dispensing manifold assembly 300 when selectively actuated to a first position, and closed fluid communication between the dilution container 260 and the peristaltic pump 200 when selectively actuated to a second position. Thus, the valve 265 is actuated to be in the second position and a fluid flow meter may be used to calibrate the amount of dilution solution that flows from the dilution container 260 into the bulk product container 100 in association with the step motor revolutions of the peristaltic pump 200.

Figure 39:
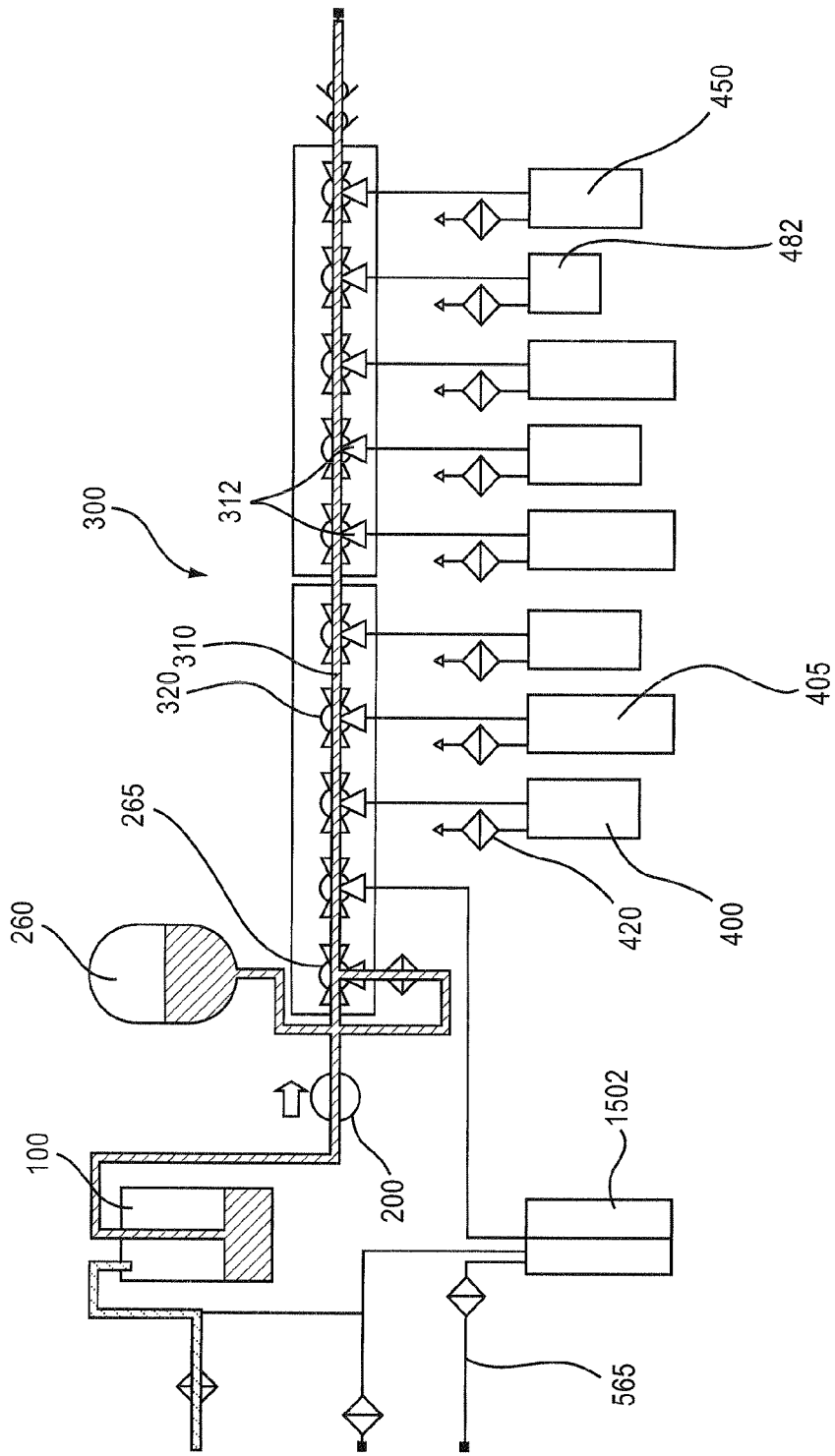
FIG. 39 is a schematic diagram to illustrate exemplary aspects of a closed vial fill system incorporating a CAV sensor and a method of using the closed vial fill system, in accordance with certain aspects of the present invention.

According to another aspect of the present invention, the bulk product vial 100 may be situated on a precision scale 46, in which the volume of solution being supplied to the bulk product container can be determined based on the measured mass of the solution. The volume may then be compared with the expected volume based on a set of predetermined flow characteristics of the peristaltic pump 200 and the associated peristaltic tubing, and the peristaltic pump 200 may be calibrated accordingly. As shown in FIG. 39, with the peristaltic pump 200 thus calibrated, the pump 200 may be controlled to operate in the opposite direction, e.g. clockwise, and the valve 265 controlled to be in the first position in order to pump the dilution solution from the bulk product vial 100 through the dispensing manifold assembly 300 and into the waste receptacle 620, for example.

Figure 40:
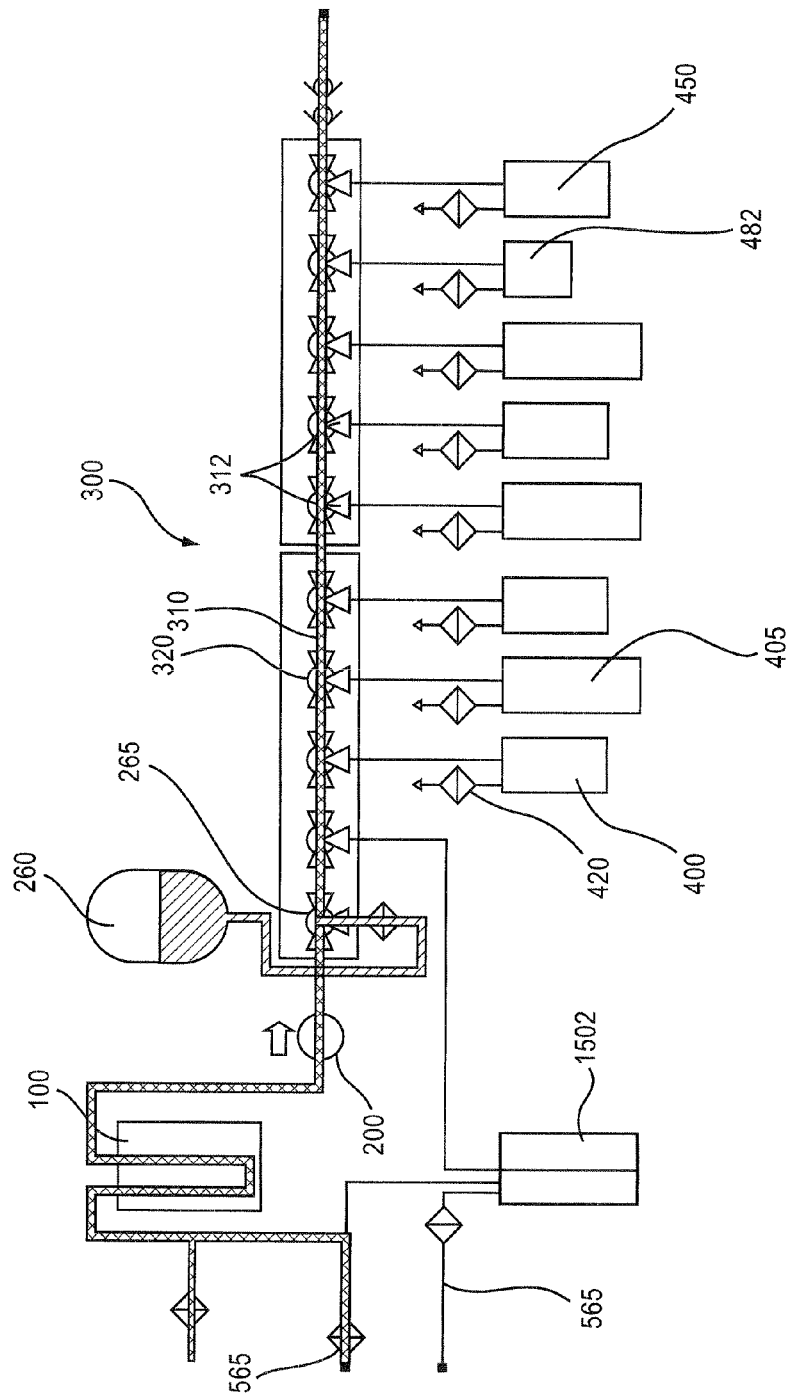
FIG. 40 is a schematic diagram to illustrate exemplary aspects of a closed vial fill system incorporating a CAV sensor and a method of using the closed vial fill system, in accordance with certain aspects of the present invention.
Figure 41:
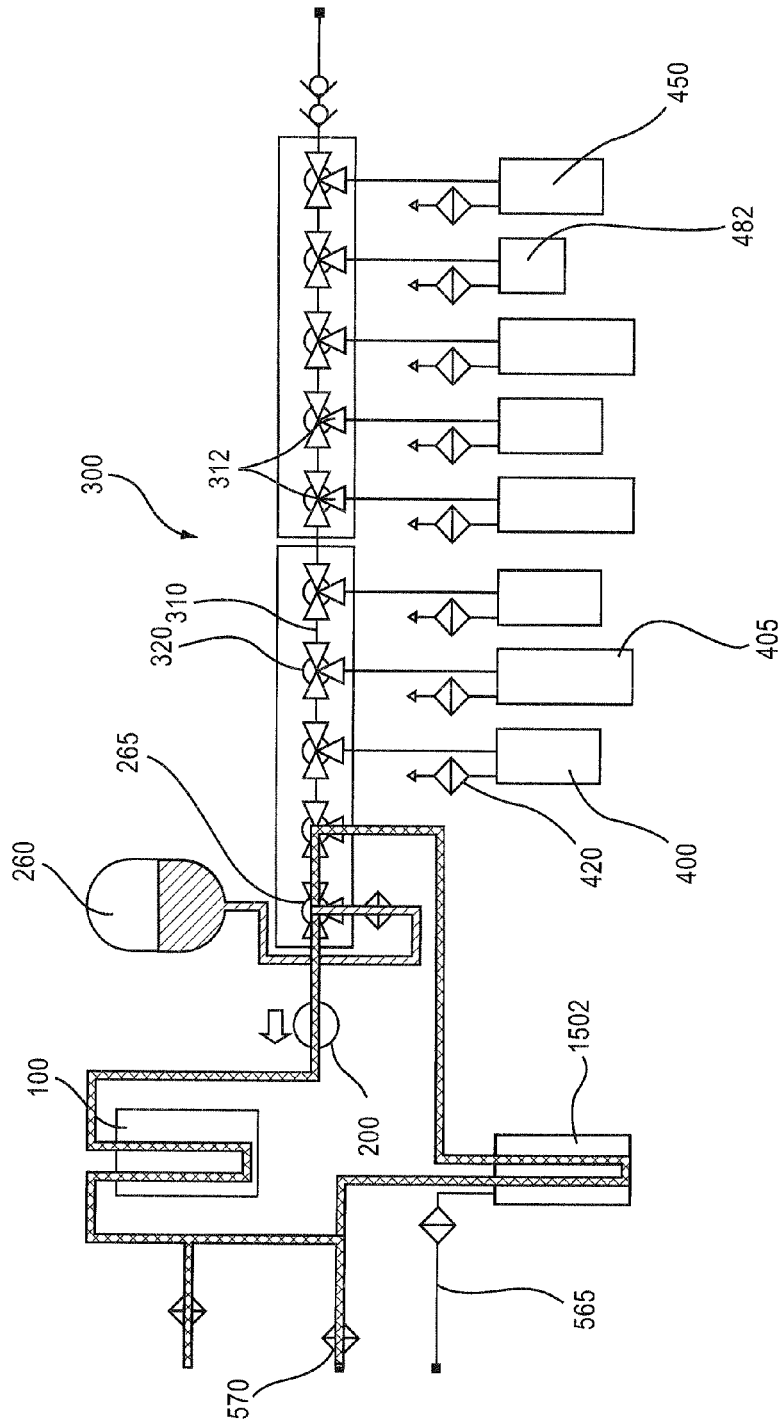
FIG. 41 is a schematic diagram to illustrate exemplary aspects of a closed vial fill system incorporating a CAV sensor and a method of using the closed vial fill system, in accordance with certain aspects of the present invention.
Figure 42:
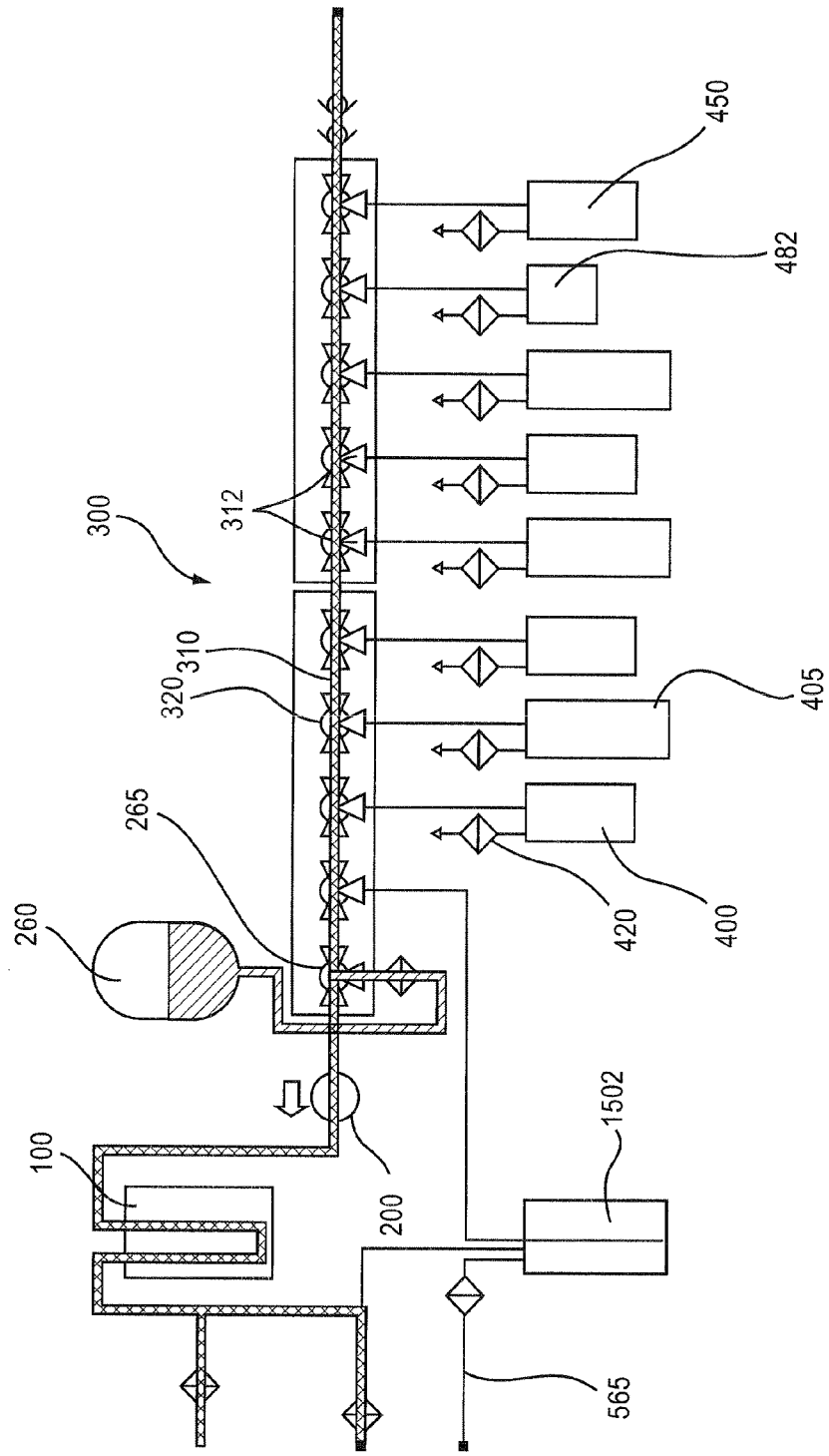
FIG. 42 is a schematic diagram to illustrate exemplary aspects of a closed vial fill system incorporating a CAV sensor and a method of using the closed vial fill system, in accordance with certain aspects of the present invention.

FIGS. 40-42 illustrate a purge process that may be initiated following the pump calibration. As shown in FIG. 40, the purge gas, preferably pressurized nitrogen, may be directed through a line 570 into the bulk product vial 100. With the peristaltic pump 200 operating in a clockwise direction, for example, the valve 265 may be actuated to direct the purge gas through the dispensing manifold assembly 300. As shown in FIG. 41, the peristaltic pump 200 may then be operated in the reverse direction and the purge gas directed in a reverse direction, first through the CAV container 1502 and then to the bulk product vial 100, where it may be vented to the atmosphere. As shown in FIG. 42, the peristaltic pump 200 may be reversed yet again to purge each of the vials, preferably in order, with the purge gas being vented to the atmosphere through each of the vented vial fill caps 420. Finally, if needed, the input line 565 from the synthesis unit may be purged using purge gas supplied from the synthesis unit.

Figure 43:
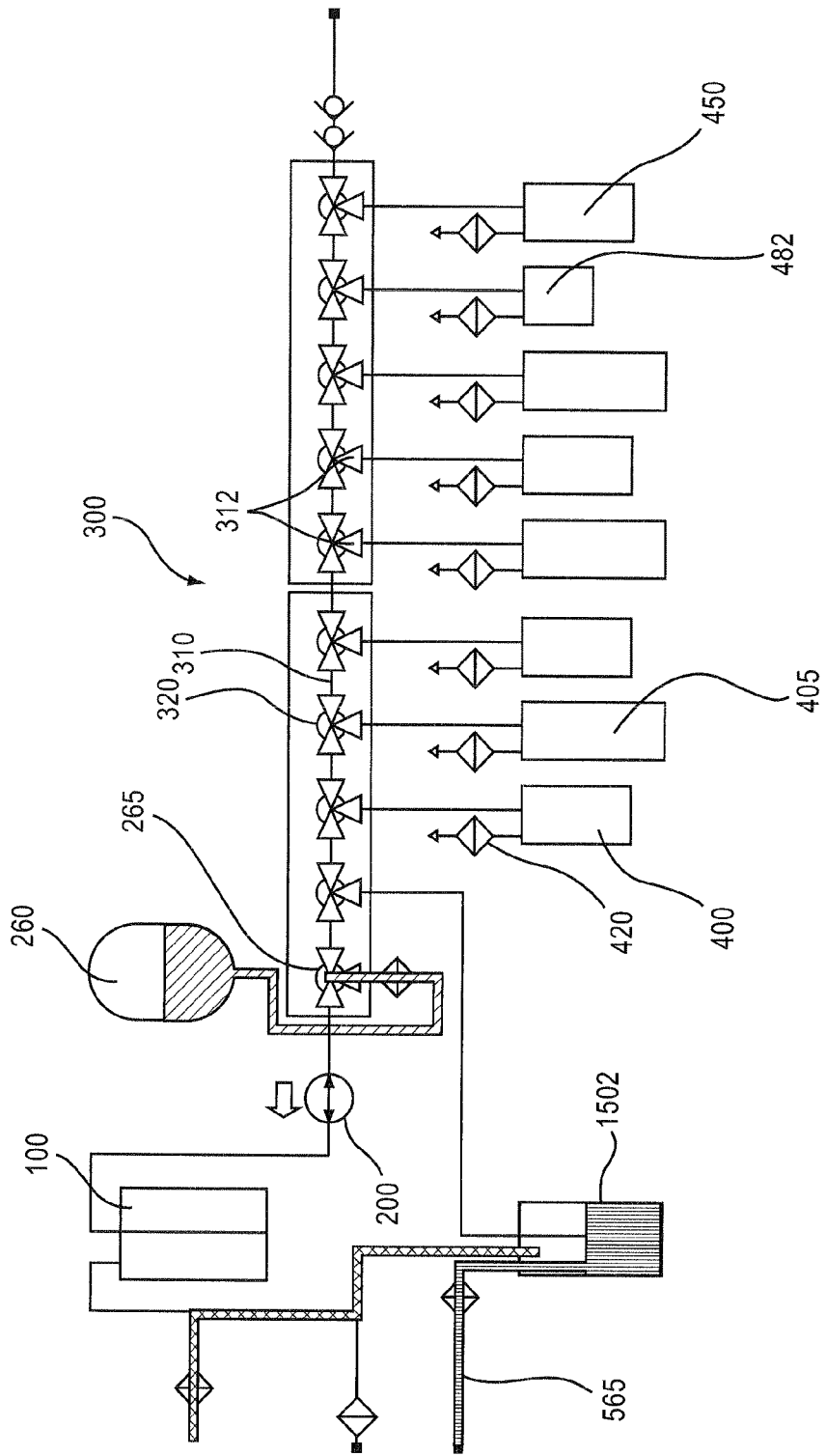
FIG. 43 is a schematic diagram to illustrate exemplary aspects of a closed vial fill system incorporating a CAV sensor and a method of using the closed vial fill system, in accordance with certain aspects of the present invention.
Figure 44:
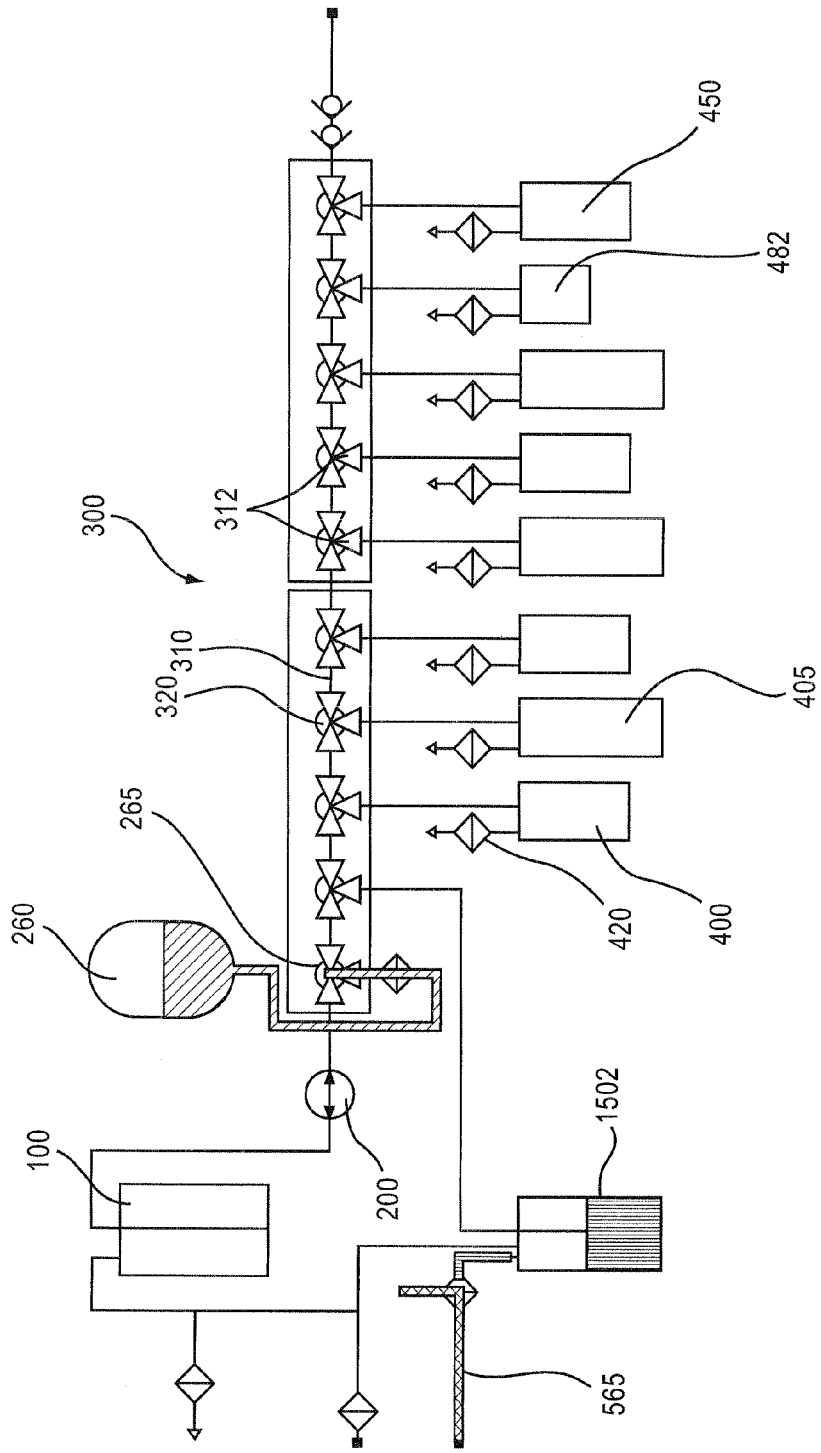
FIG. 44 is a schematic diagram to illustrate exemplary aspects of a closed vial fill system incorporating a CAV sensor and a method of using the closed vial fill system, in accordance with certain aspects of the present invention.

As shown in FIG. 43, following the purging of the disposable components with nitrogen, the concentrated radiopharmaceutical product 110 may be received into the CAV container 1502 from the synthesis unit through the input line 565. As shown in FIG. 44, once the concentrated product 110 has been completely received, the input line 565 may be purged with nitrogen to clear the line. With the concentrated radiopharmaceutical product 110 in the CAV container 1502, the user may select to measure the activity in the CAV container 1502. The control system 700 may then activate the CAV sensor 1500 to obtain desired parameters, such as activity and concentration of the concentrated radiopharmaceutical product 110.

Figure 45:
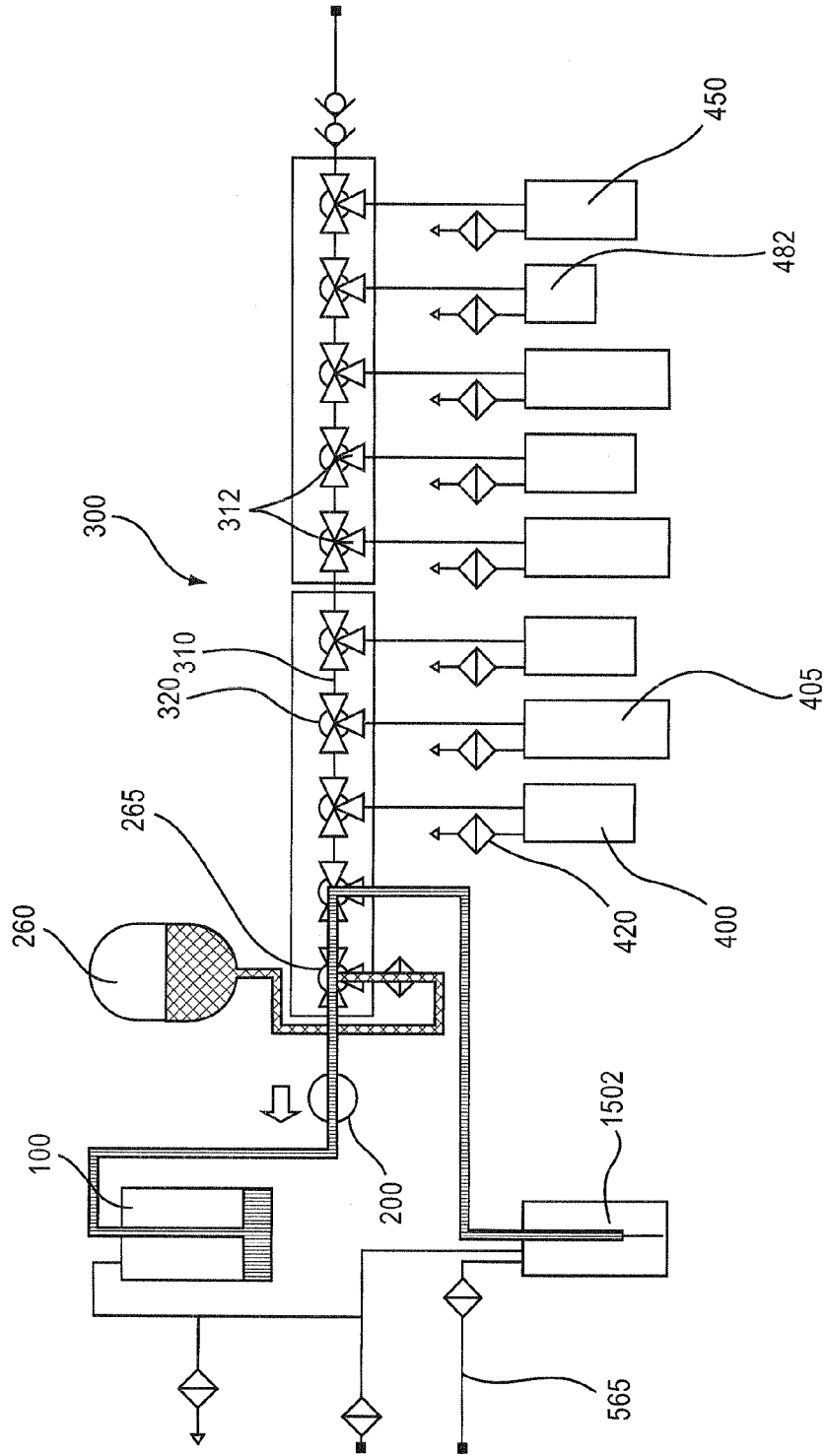
FIG. 45 is a schematic diagram to illustrate exemplary aspects of a closed vial fill system incorporating a CAV sensor and a method of using the closed vial fill system, in accordance with certain aspects of the present invention.
Figure 46:
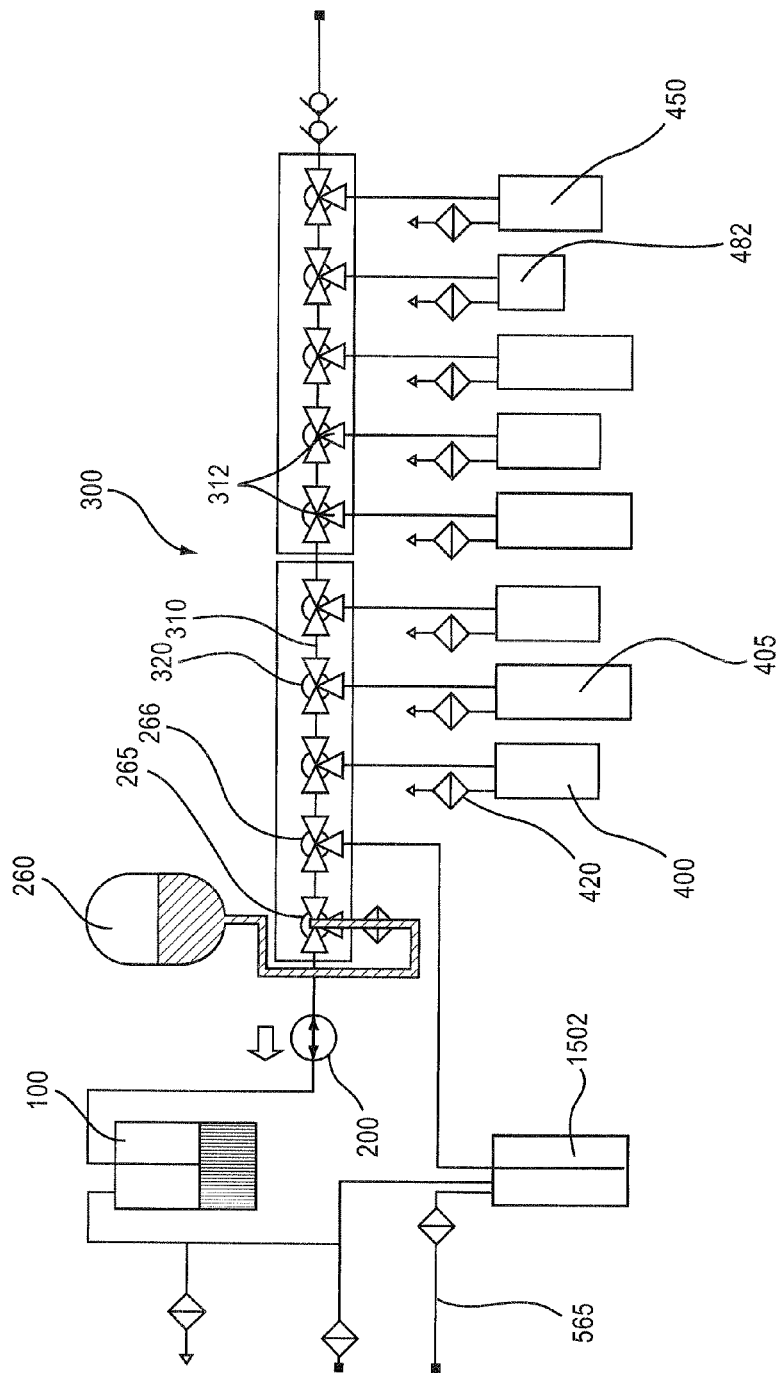
FIG. 46 is a schematic diagram to illustrate exemplary aspects of a closed vial fill system incorporating a CAV sensor and a method of using the closed vial fill system, in accordance with certain aspects of the present invention.

As shown in FIG. 45, the CAV container 1502 may be connected to a three-way valve 266, which may be one of the valves of the dispensing manifold assembly 300. The valve 266 may be actuated to a first position in which a fluid flow path is opened between the CAV container 1502 and the bulk product vial 100. When actuated to a second position, the valve may shut off fluid flow to the CAV container 502 and allow unimpeded, substantially laminar fluid flow through the manifold tube 310. After the CAV sensor 1500 has obtained the desired parameters, as shown in FIG. 45, and with the valve 266 actuated to the first position, the peristaltic pump 200 may be actuated to operate in reverse to transfer the concentrated radiopharmaceutical product 110 from the CAV container 1502 to the bulk product vial 100. As shown in FIG. 46, with the entirety of the concentrated product 110 transferred to the bulk product vial 100, the mass, and hence volume, of the concentrated product 110 may be determined, such as by using the precision scale 46 discussed above, for example. In the case where the volume of the concentrated product 110 is determined by the CAV sensor 1500, the precision scale 46 may serve as a quality check to verify the accuracy of the CAV sensor volume measurement.

Figure 47:
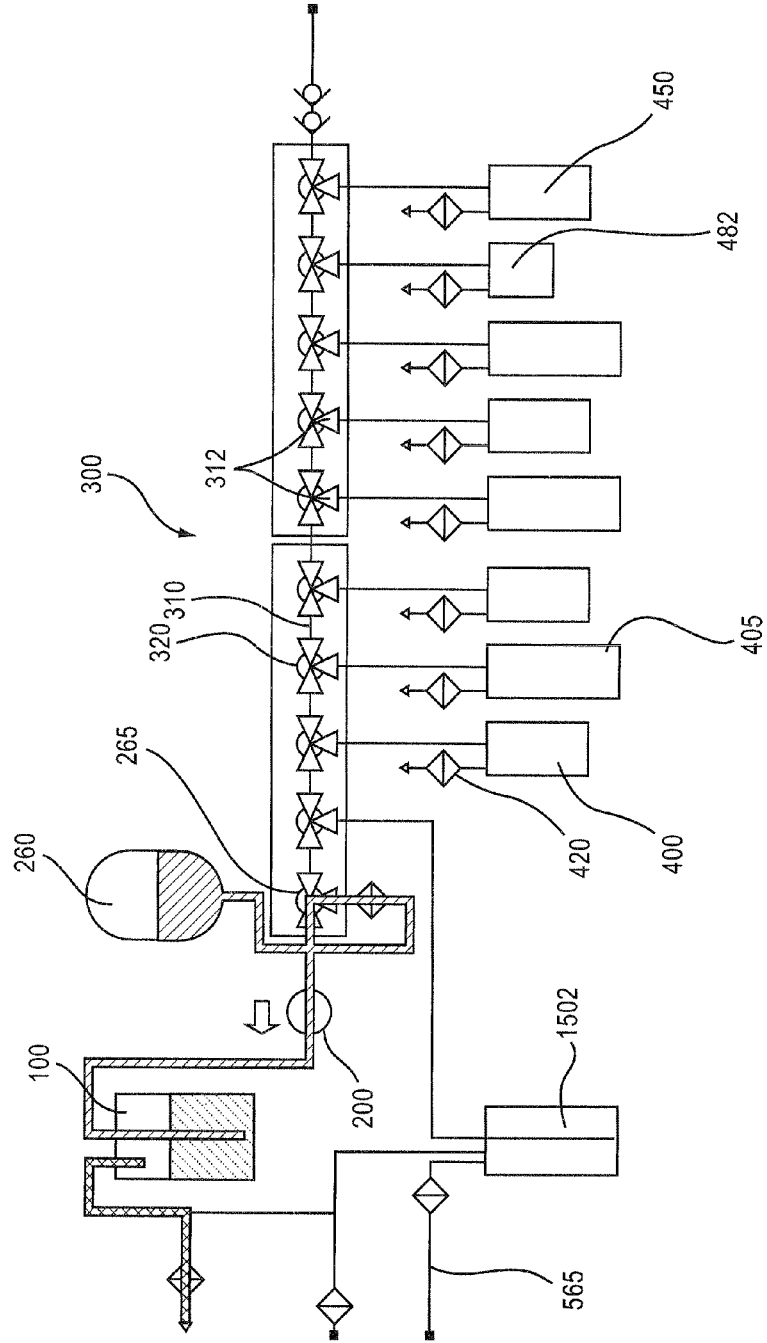
FIG. 47 is a schematic diagram to illustrate exemplary aspects of a closed vial fill system incorporating a CAV sensor and a method of using the closed vial fill system, in accordance with certain aspects of the present invention.

To begin the automated vial fill process, the user may be requested to perform a "Set-Up" task, wherein the user inputs a dilution solution volume and the vial fill volumes for each of the vials attached to the dispensing manifold assembly 300. Once complete, the user may select a "Start Fill" command, for example, to begin the automated fill process. As shown in FIG. 47, the control system 700 may actuate the peristaltic pump 200 to operate in reverse while opening the valve 265 to allow a predetermined volume of the dilution solution, as set by the user, to flow from the dilution container 260 into the bulk product vial 100.

Figure 48:
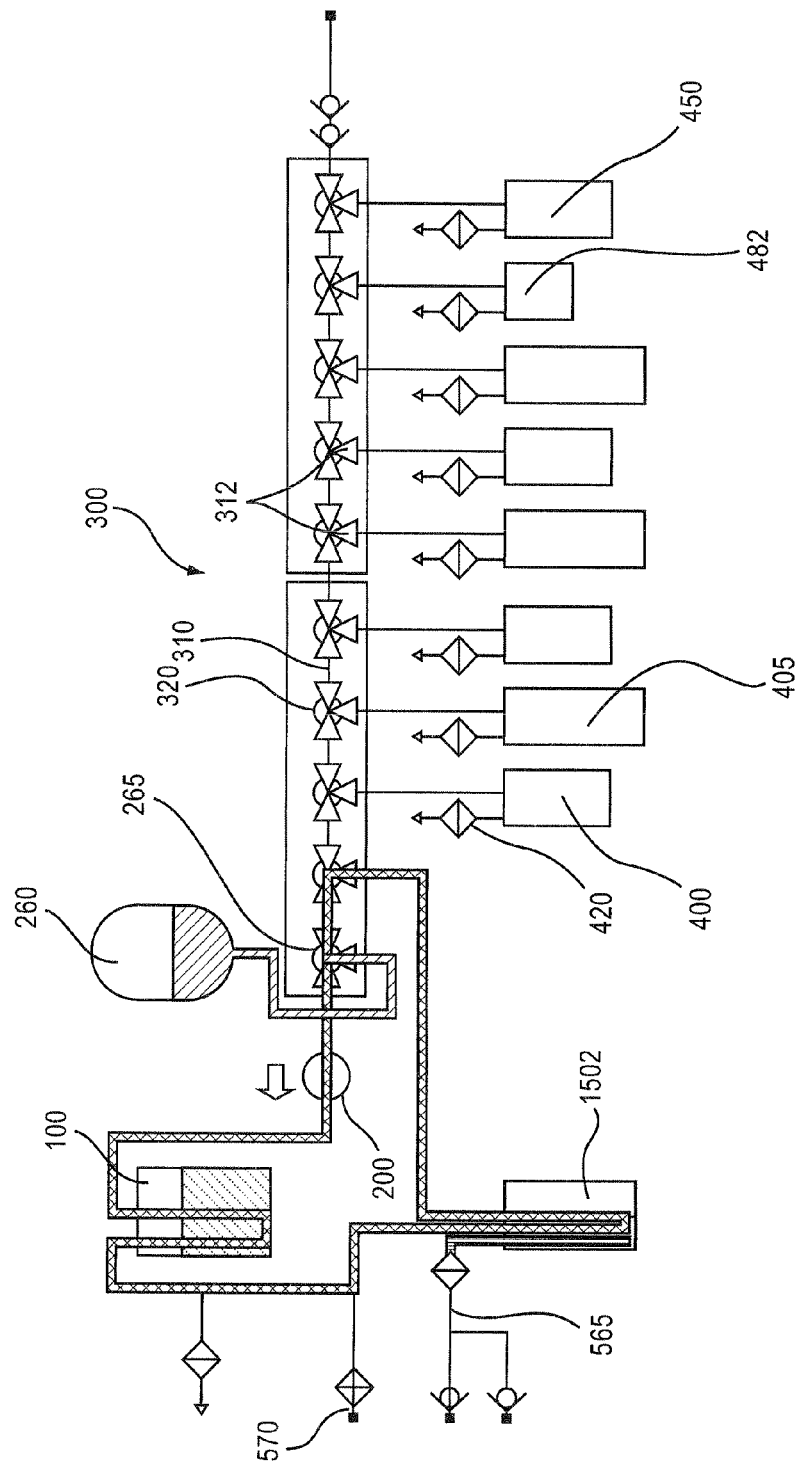
FIG. 48 is a schematic diagram to illustrate exemplary aspects of a closed vial fill system incorporating a CAV sensor and a method of using the closed vial fill system, in accordance with certain aspects of the present invention.

As shown in FIG. 48, the valve 265 may be closed to the dilution container 260 and nitrogen forced through the system to purge any remaining dilution solution from the peristaltic tubing leading to the bulk product vial 100. In doing so, nitrogen may be bubbled through the diluted radiopharmaceutical product in the bulk product vial 100 before exiting through the vent filter, for example, further helping to mix the diluted product.

In accordance with another aspect of the present invention, rather than using nitrogen to clear the lines, for example, the peristaltic pump 200 may be operated to return a small amount of the diluted product back to the CAV container 1502. The pump 200 may then be reversed again to return the small amount of diluted product from the CAV container 1502 back to the bulk product vial 100. Thus, any small amount of liquid that may be left remaining in the CAV container 1502 or the lines from the CAV container 1502 to the dispensing manifold assembly 300 will be diluted, rather than concentrated.

Figure 49:
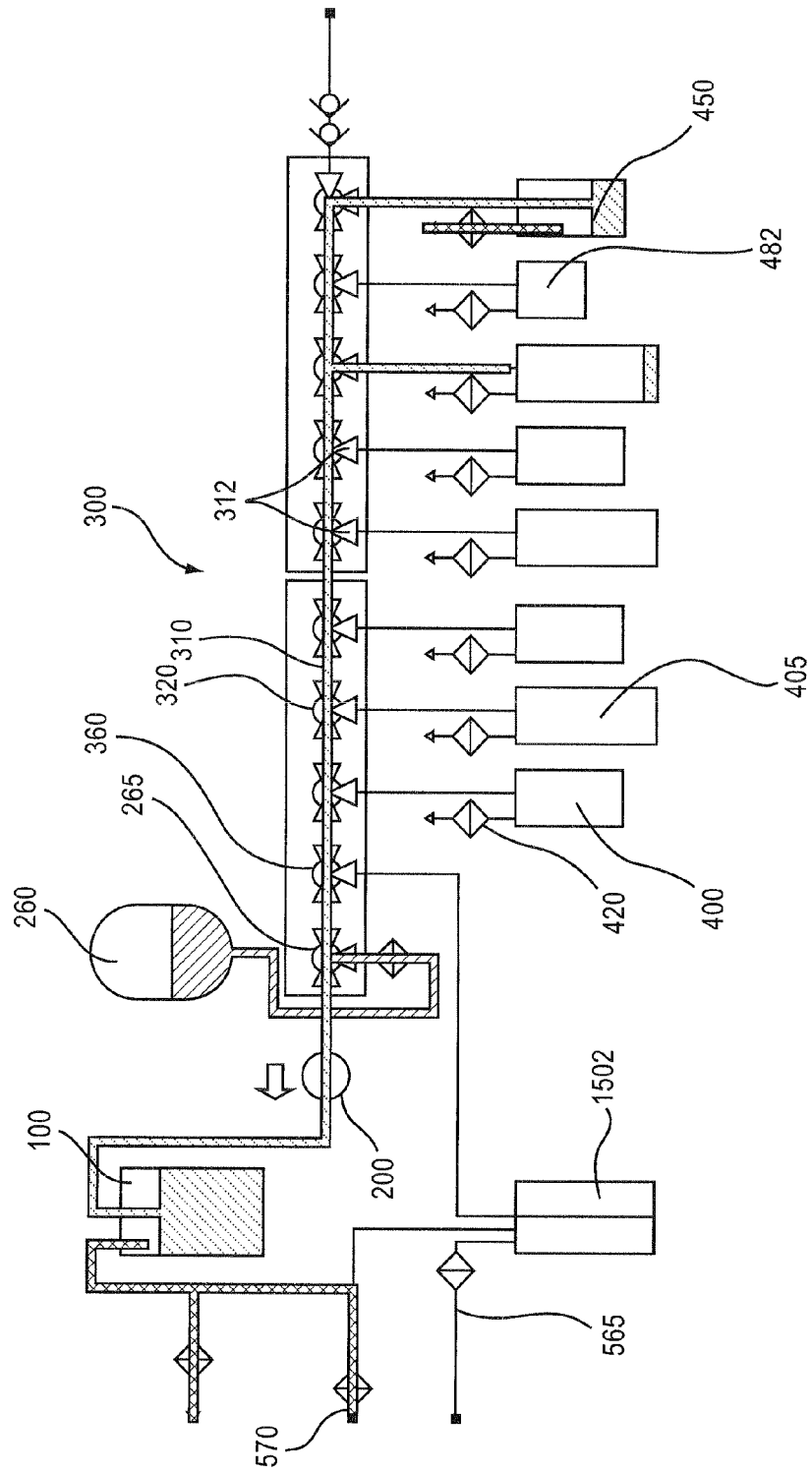
FIG. 49 is a schematic diagram to illustrate exemplary aspects of a closed vial fill system incorporating a CAV sensor and a method of using the closed vial fill system, in accordance with certain aspects of the present invention.
Figure 50:
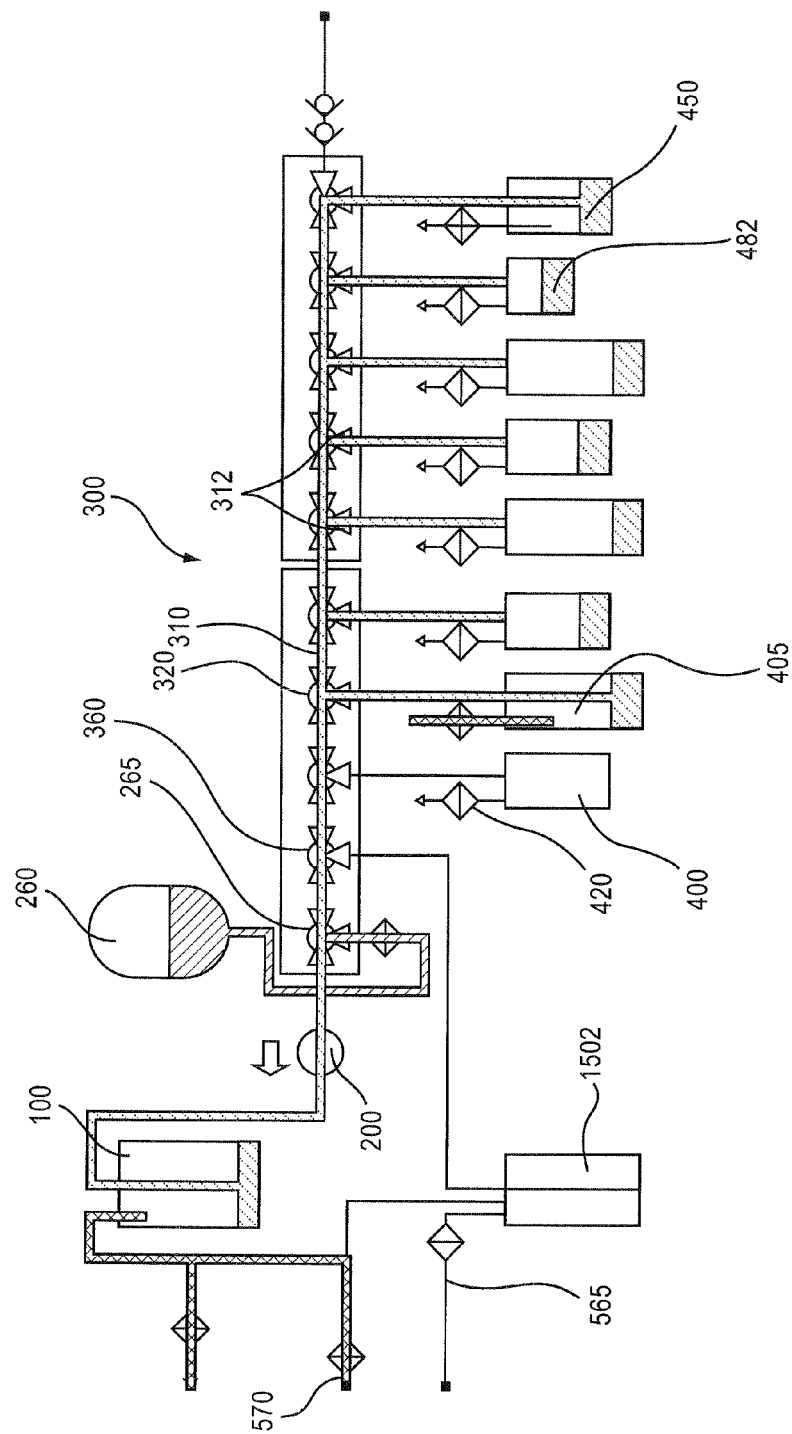
FIG. 50 is a schematic diagram to illustrate exemplary aspects of a closed vial fill system incorporating a CAV sensor and a method of using the closed vial fill system, in accordance with certain aspects of the present invention.

As shown in FIGS. 49 and 50, the control system 700 may operate the pump 200 to fill the manifold tubes 310 with the diluted product up to the furthest final product vial 400 or 405. The control system 700 may then begin filling the vials from right to left, for example, starting with the sterility vial 450, followed by the quality check vial 482, and then each of the final product vials 400 and 405. Although described in a particular order herein, the control system 700 may be configured through user input via the computer system 1200 to fill the vials in any order.

Figure 51:
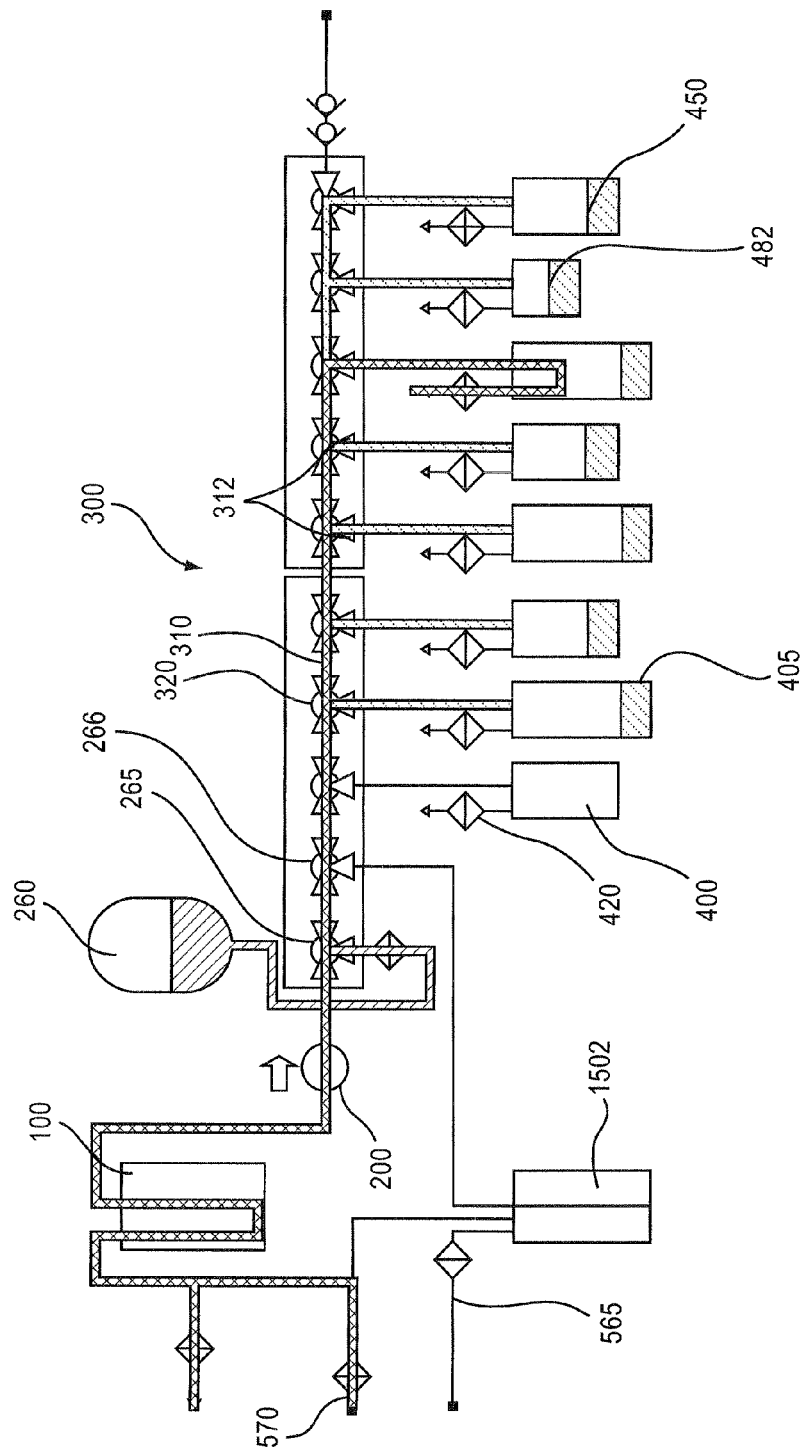
FIG. 51 is a schematic diagram to illustrate exemplary aspects of a closed vial fill system incorporating a CAV sensor and a method of using the closed vial fill system, in accordance with certain aspects of the present invention.
Figure 52:
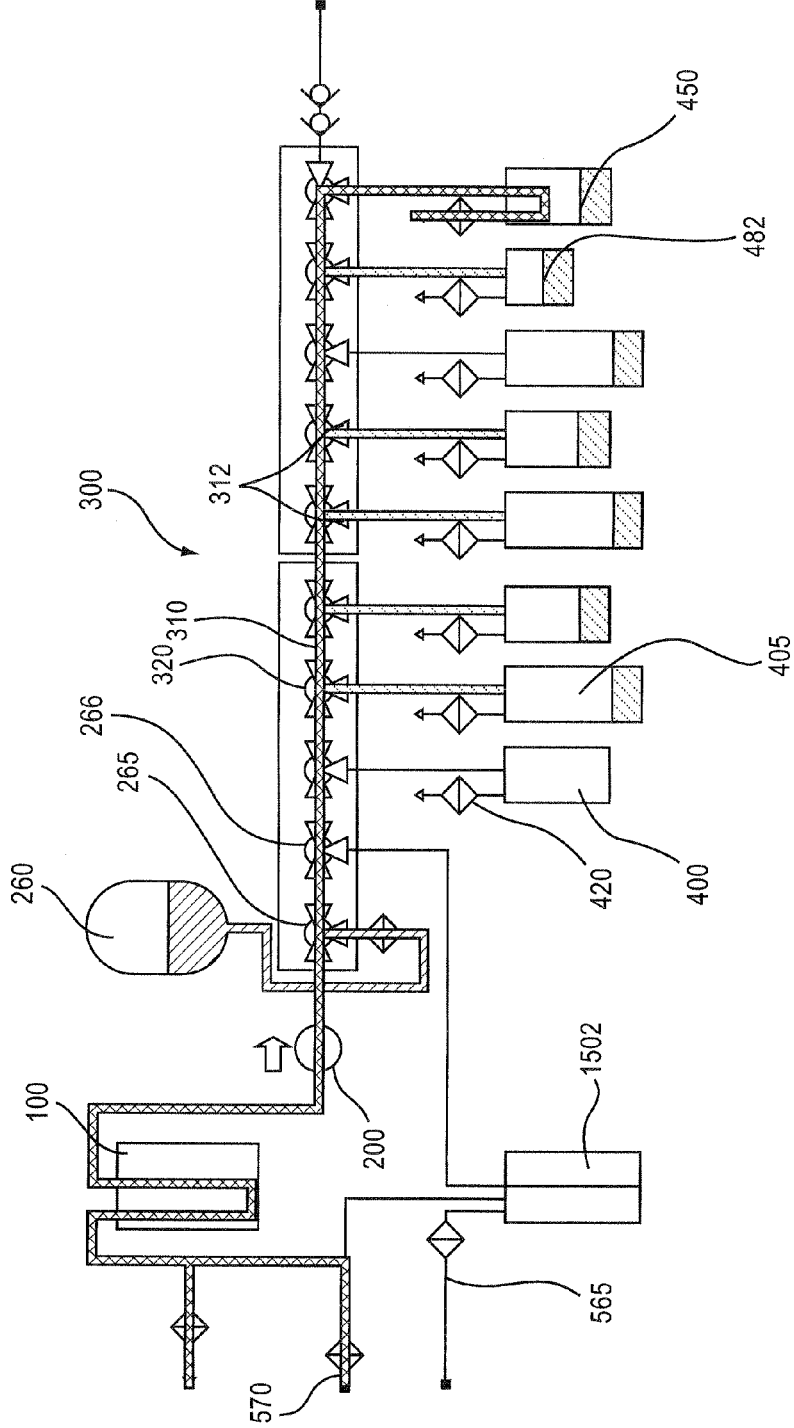
FIG. 52 is a schematic diagram to illustrate exemplary aspects of a closed vial fill system incorporating a CAV sensor and a method of using the closed vial fill system, in accordance with certain aspects of the present invention.
Figure 53:
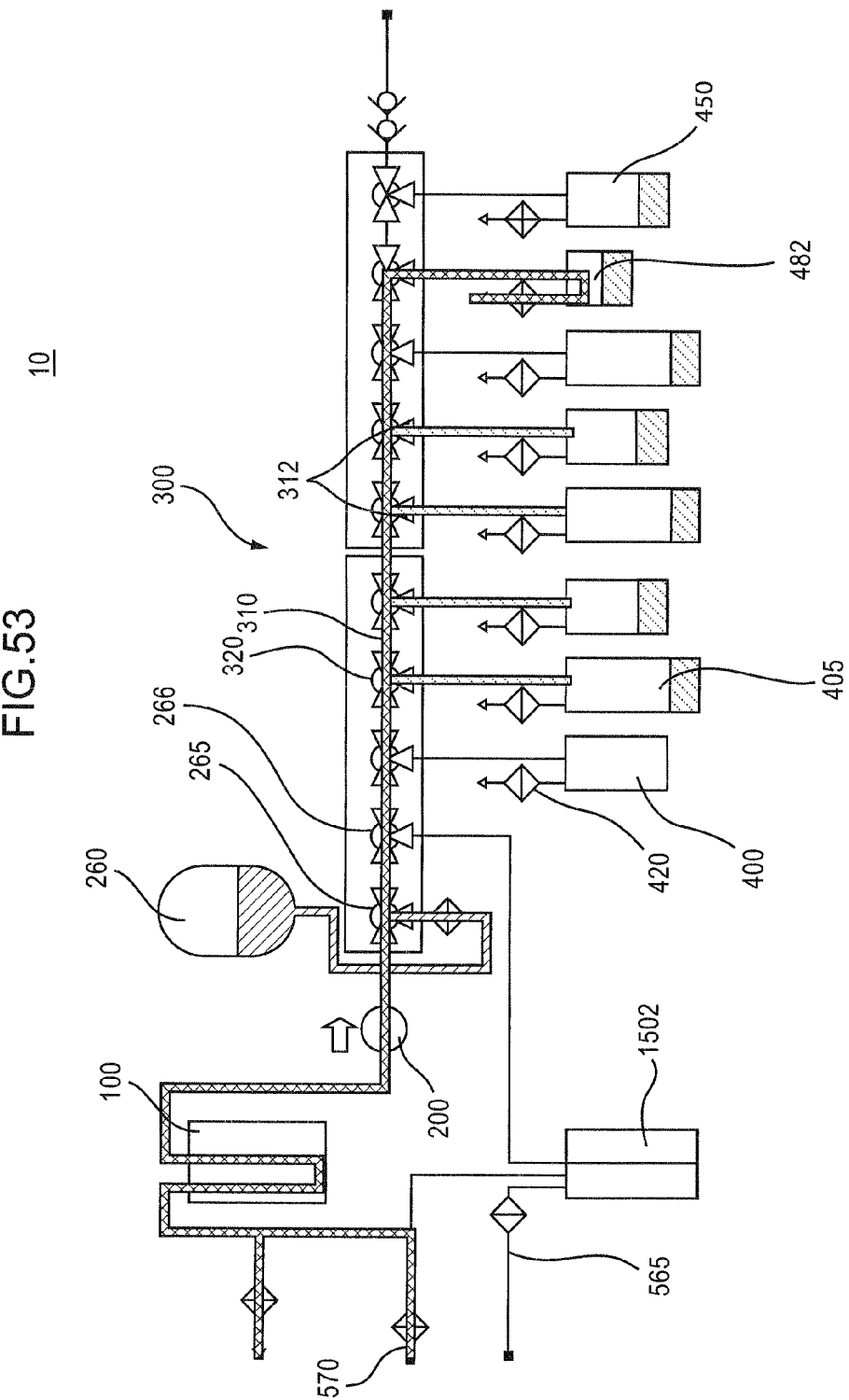
FIG. 53 is a schematic diagram to illustrate exemplary aspects of a closed vial fill system incorporating a CAV sensor and a method of using the closed vial fill system, in accordance with certain aspects of the present invention.
Figure 54:
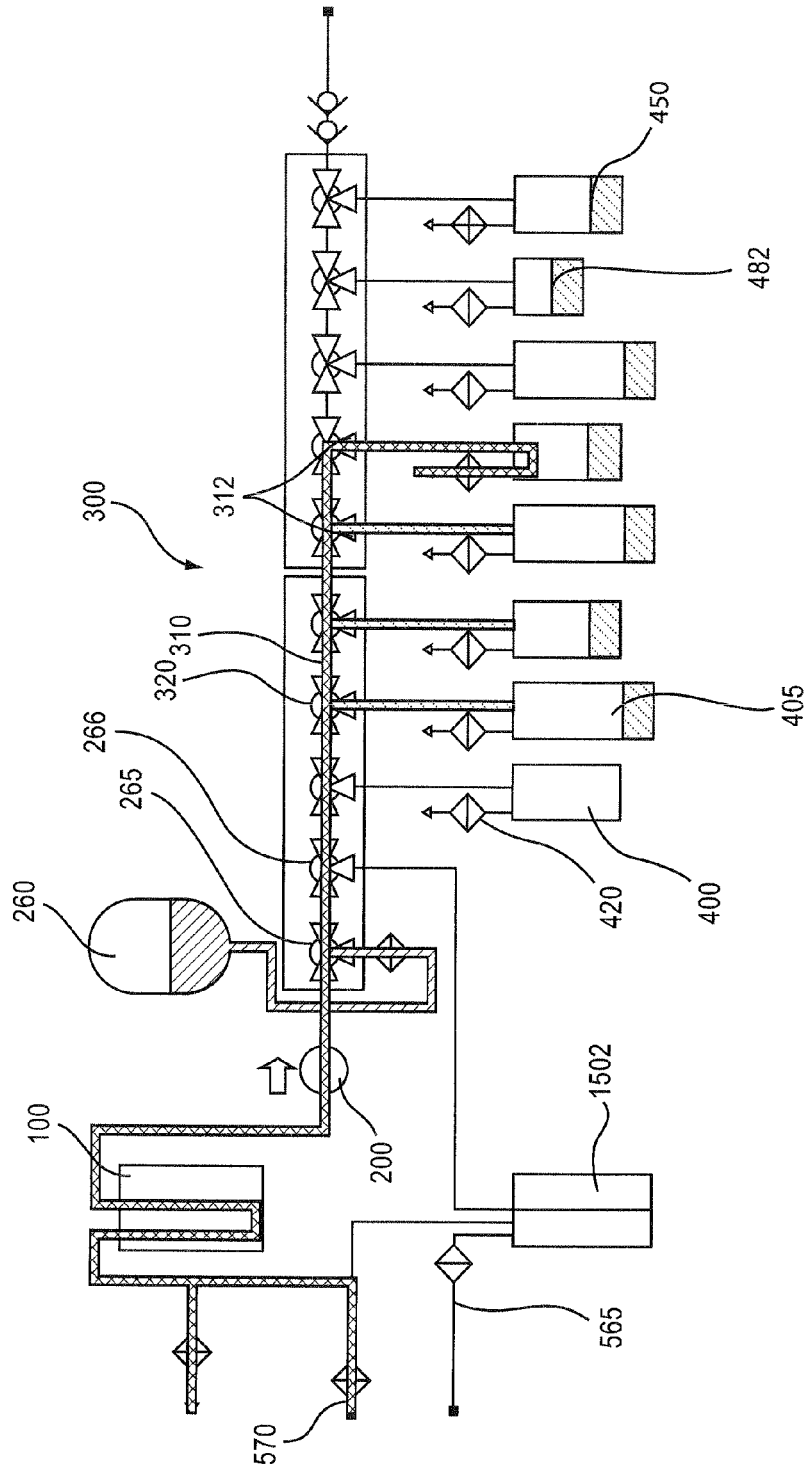
FIG. 54 is a schematic diagram to illustrate exemplary aspects of a closed vial fill system incorporating a CAV sensor and a method of using the closed vial fill system, in accordance with certain aspects of the present invention.
Figure 55:
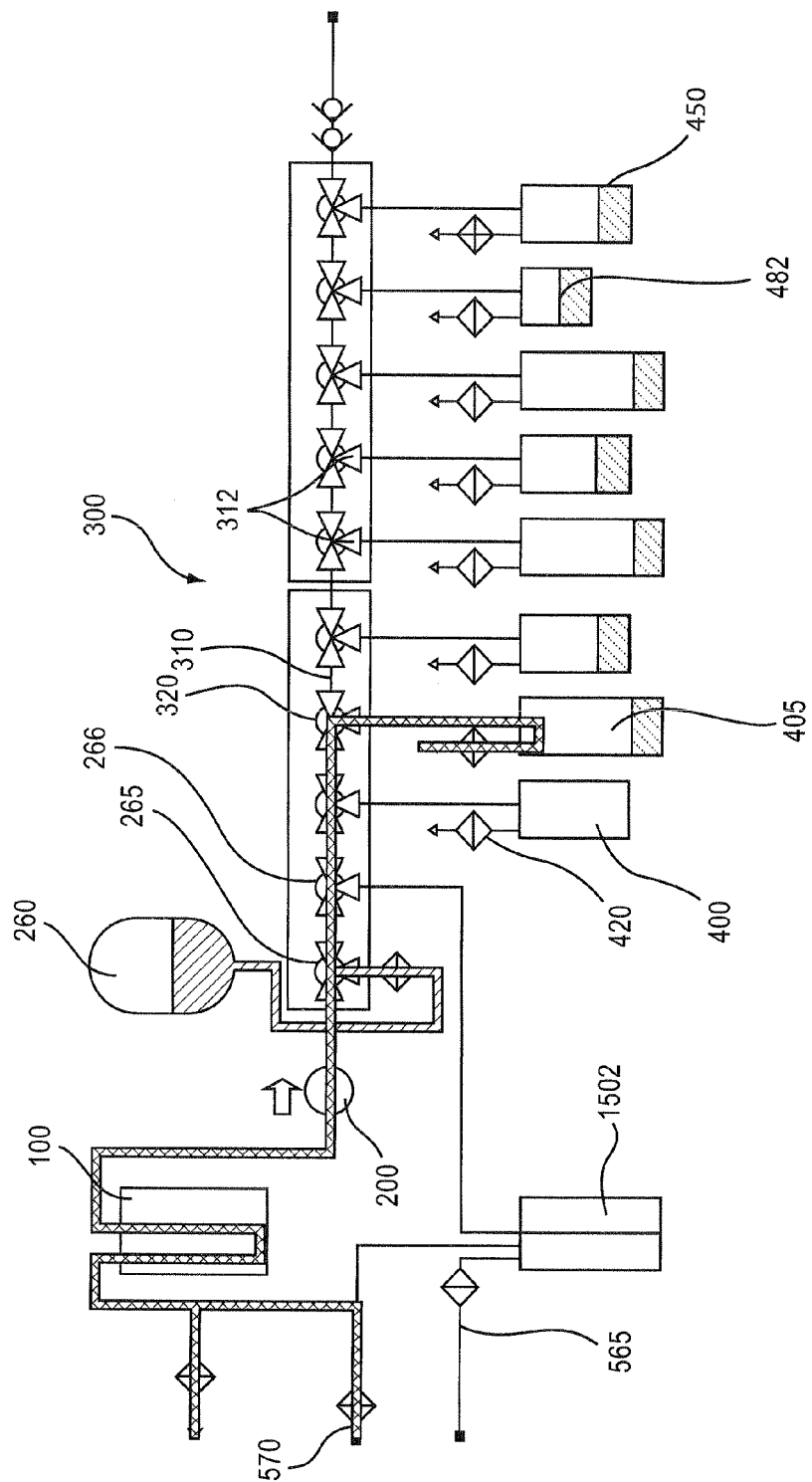
FIG. 55 is a schematic diagram to illustrate exemplary aspects of a closed vial fill system incorporating a CAV sensor and a method of using the closed vial fill system, in accordance with certain aspects of the present invention.

As shown in FIG. 51, excess diluted product in the bulk product vial 100, along with excess diluted product in the peristaltic tubing and the manifold tubes 310, for example, may be purged using nitrogen and collected in a final product vial 405 connected to the manifold tube 310 furthest from the pump 200. As shown in FIGS. 52-55, the fill process may be completed by purging any diluted product remaining in the lines to the vials, for example, preferably beginning with the vial farthest away from the pump and continuing with each closer vial until all of the vials have been purged.

Figure 56:
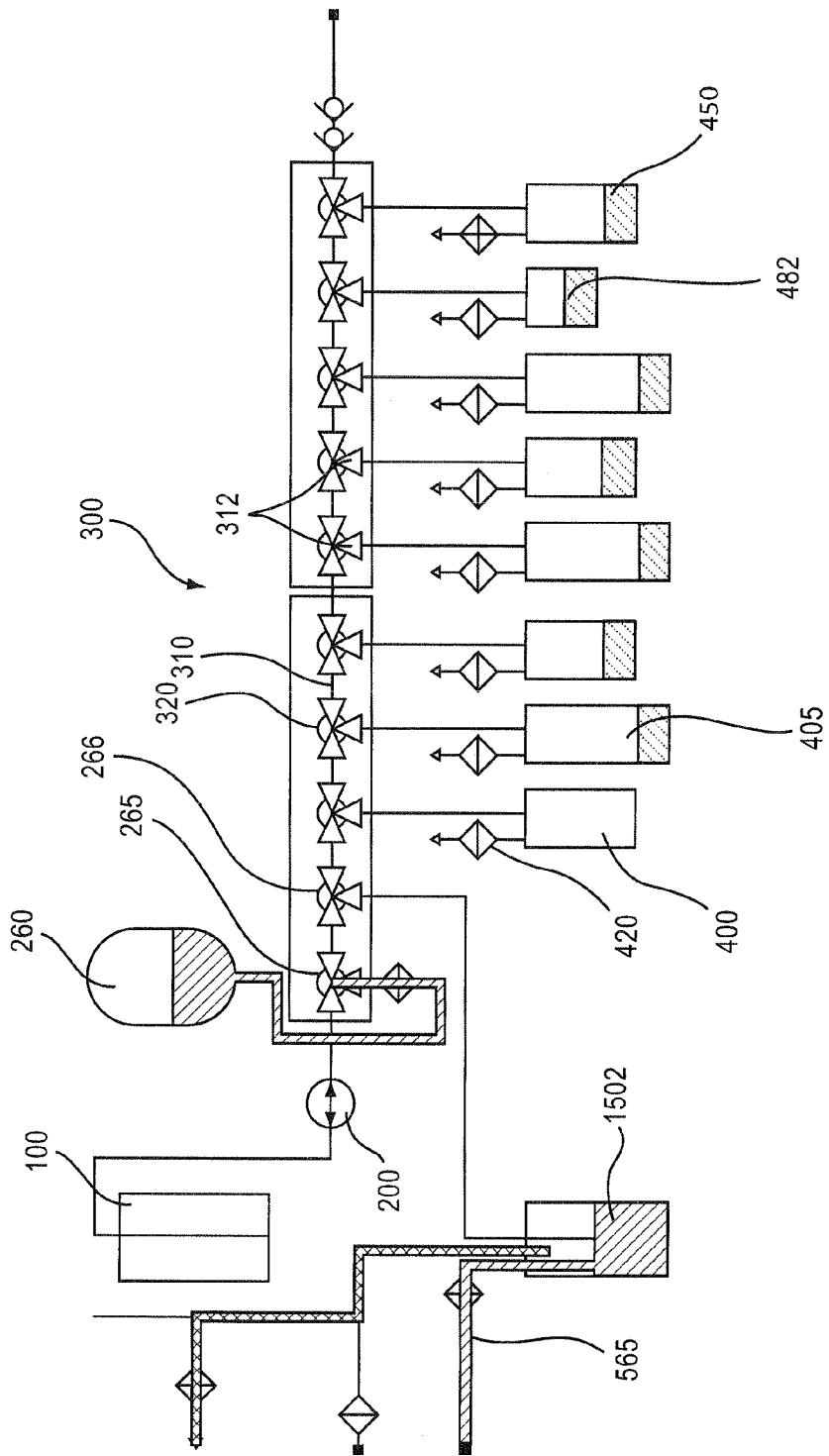
FIG. 56 is a schematic diagram to illustrate exemplary aspects of a closed vial fill system incorporating a CAV sensor and a method of using the closed vial fill system, in accordance with certain aspects of the present invention.
Figure 57:
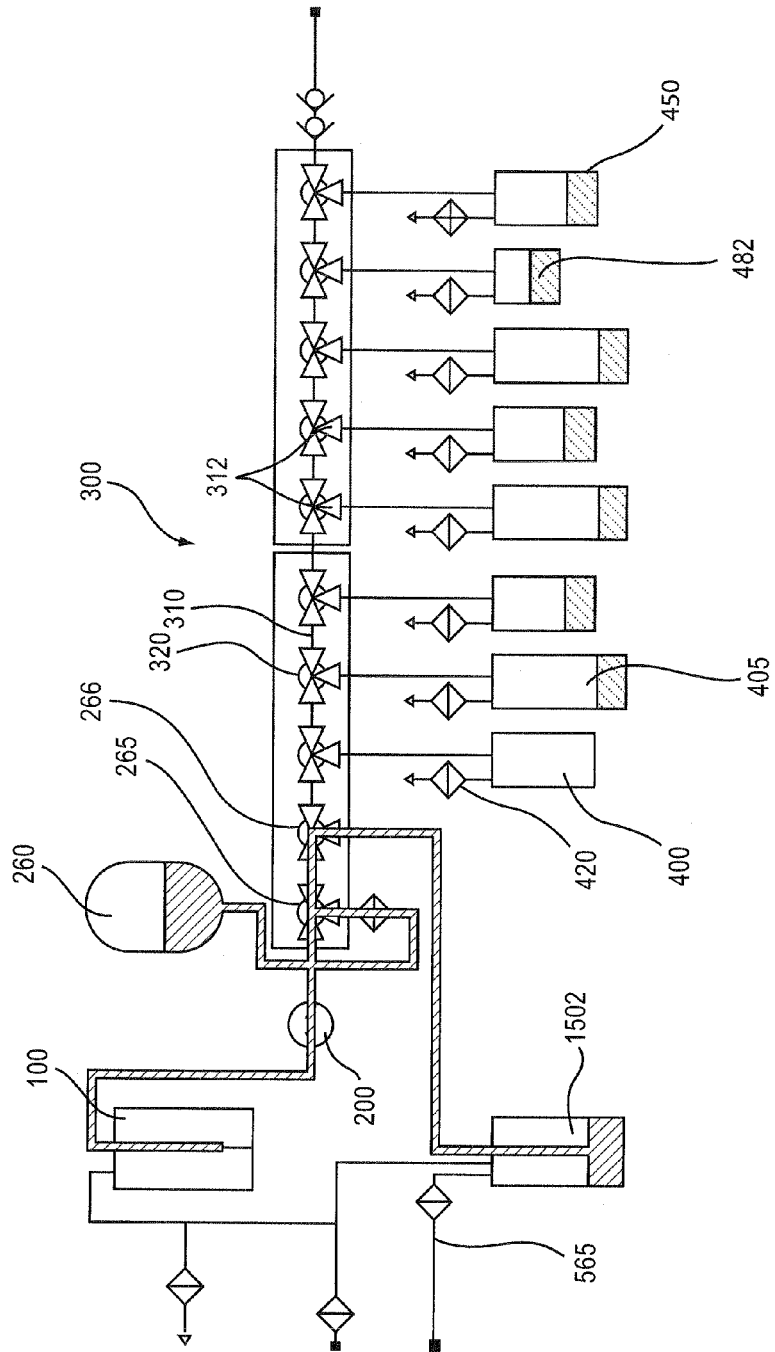
FIG. 57 is a schematic diagram to illustrate exemplary aspects of a closed vial fill system incorporating a CAV sensor and a method of using the closed vial fill system, in accordance with certain aspects of the present invention.
Figure 58:
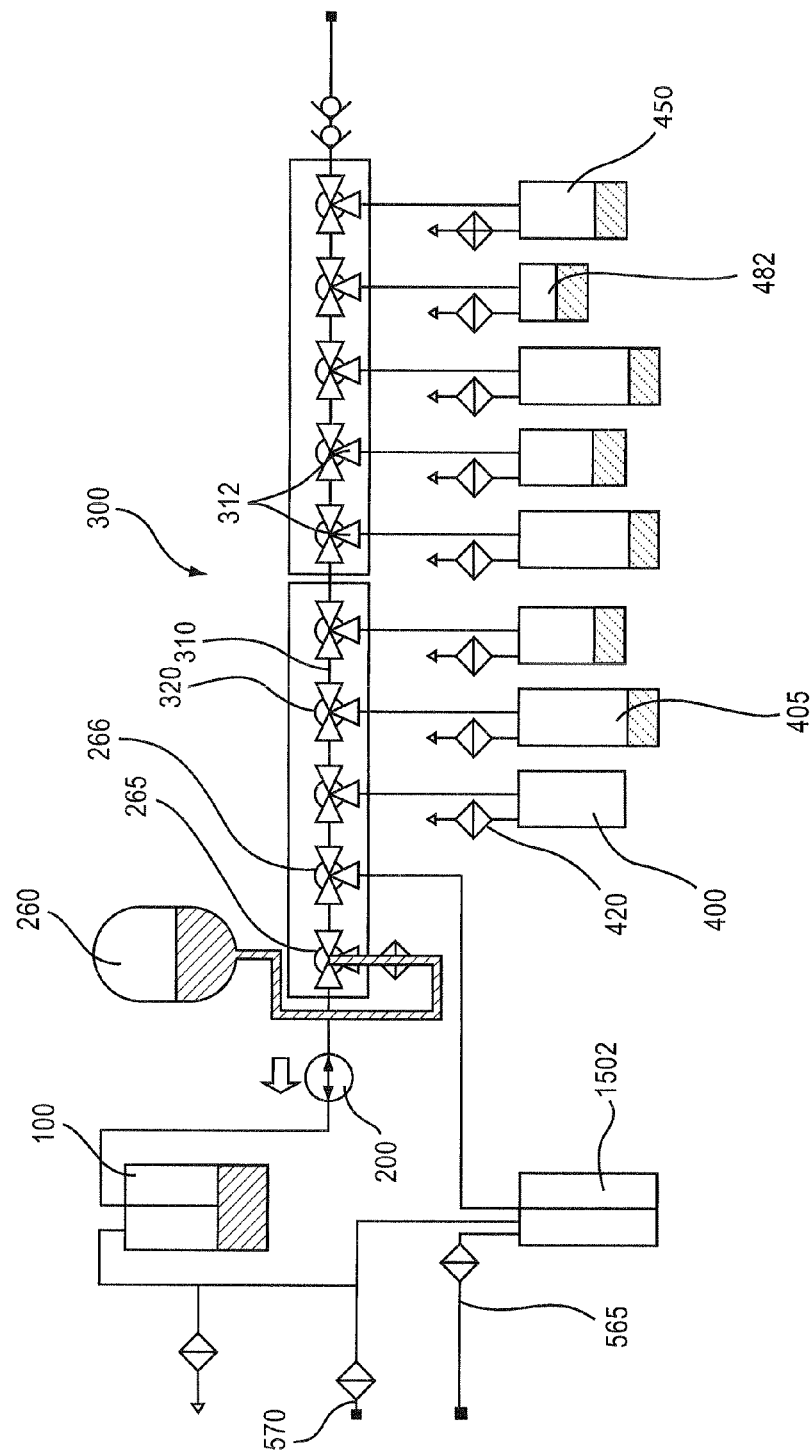
FIG. 58 is a schematic diagram to illustrate exemplary aspects of a closed vial fill system incorporating a CAV sensor and a method of using the closed vial fill system, in accordance with certain aspects of the present invention.
Figure 59:
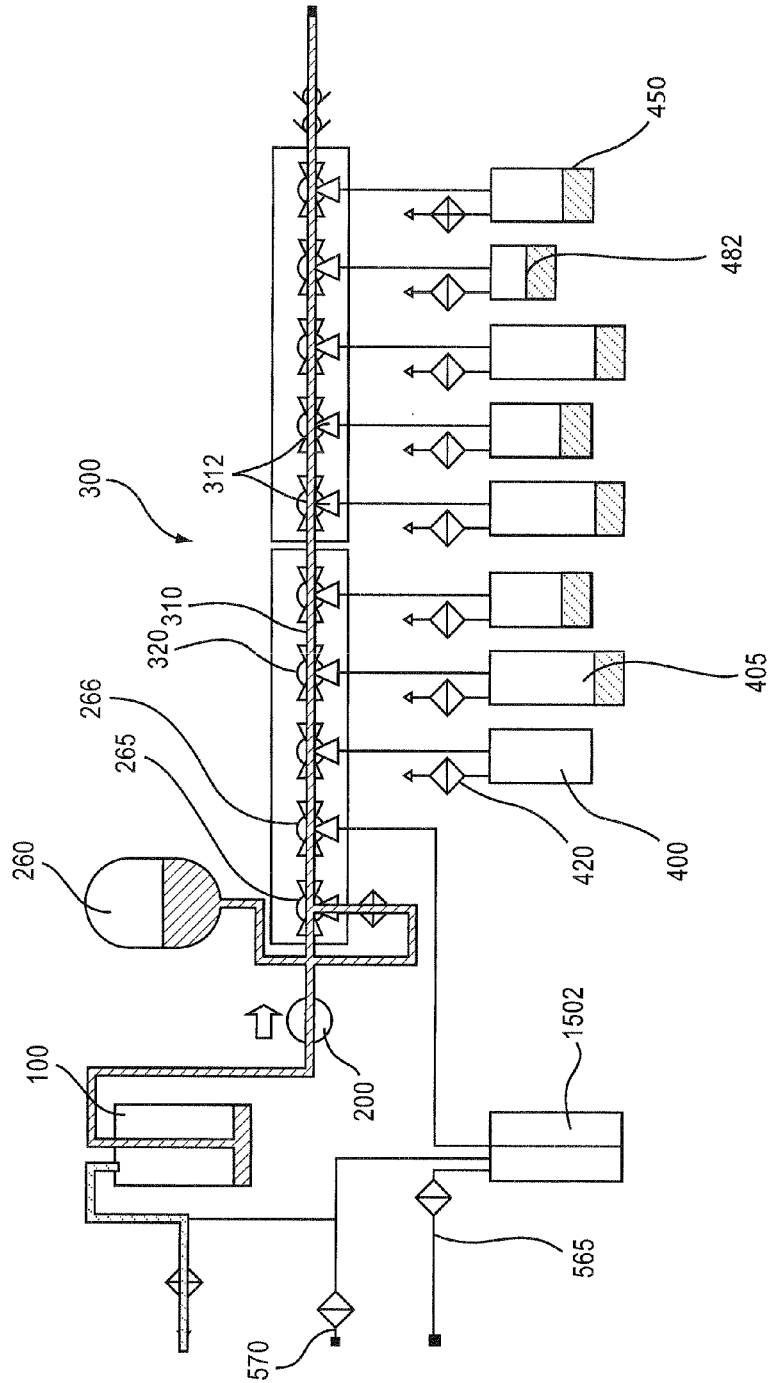
FIG. 59 is a schematic diagram to illustrate exemplary aspects of a closed vial fill system incorporating a CAV sensor and a method of using the closed vial fill system, in accordance with certain aspects of the present invention.
Figure 60:
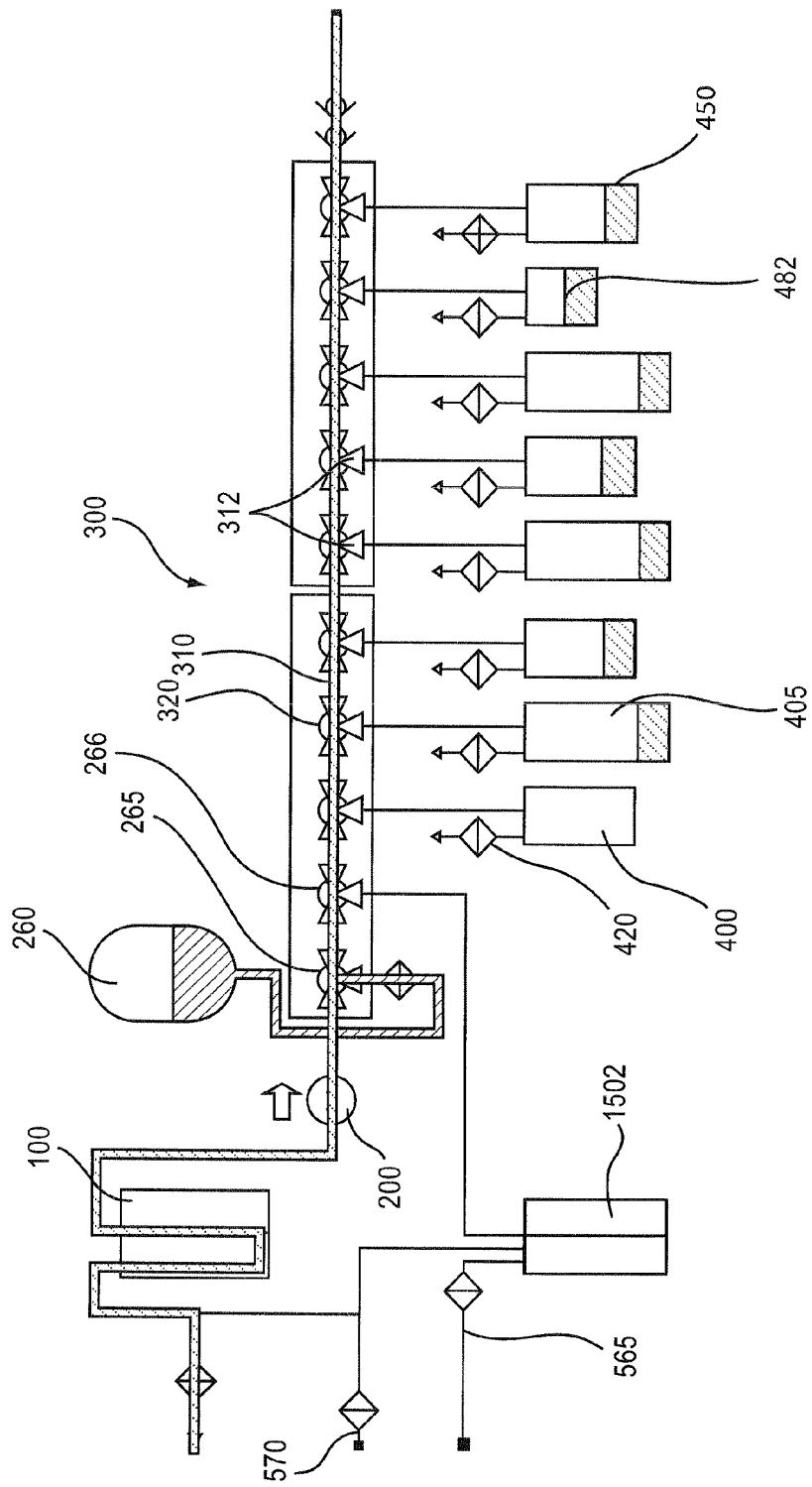
FIG. 60 is a schematic diagram to illustrate exemplary aspects of a closed vial fill system incorporating a CAV sensor and a method of using the closed vial fill system, in accordance with certain aspects of the present invention.

In accordance with another aspect of the present invention, as shown in FIG. 56, a rinse, such as water, or any other suitable cleansing fluid, may be provided from the synthesis unit to further clean the disposables of possible radioactive residue. The rinse may be delivered from the synthesis unit through the line 565 and deposited into the CAV container 1502. Once the rinse is delivered to the CAV container 1502, the user may select a "Start Rinse" command, for example, to begin the rinse process. As shown in FIGS. 57 and 58, the control system 700 may actuate the peristaltic pump 200 to operate in a reverse direction in order to transfer the rinse from the CAV container 1502 to the bulk product vial 100. As shown in FIG. 59, with the CAV container 1502 and the fluid lines between the CAV container 1502 and the bulk product vial 100 thus rinsed, the peristaltic pump 200 may be operated to draw the rinse from the bulk product vial 100 and force the rinse through the manifold tubes 310 to the waste receptacle (not shown). In accordance with yet another aspect of the present invention, as shown in FIG. 60, the peristaltic pump 200 may continue to operate in order to draw in atmospheric air, for example, through the vented bulk product vial 100 and pump the air through the lines and the manifold tubes 310 until all of the rinse is deposited into the waste receptacle.

Figure 61:
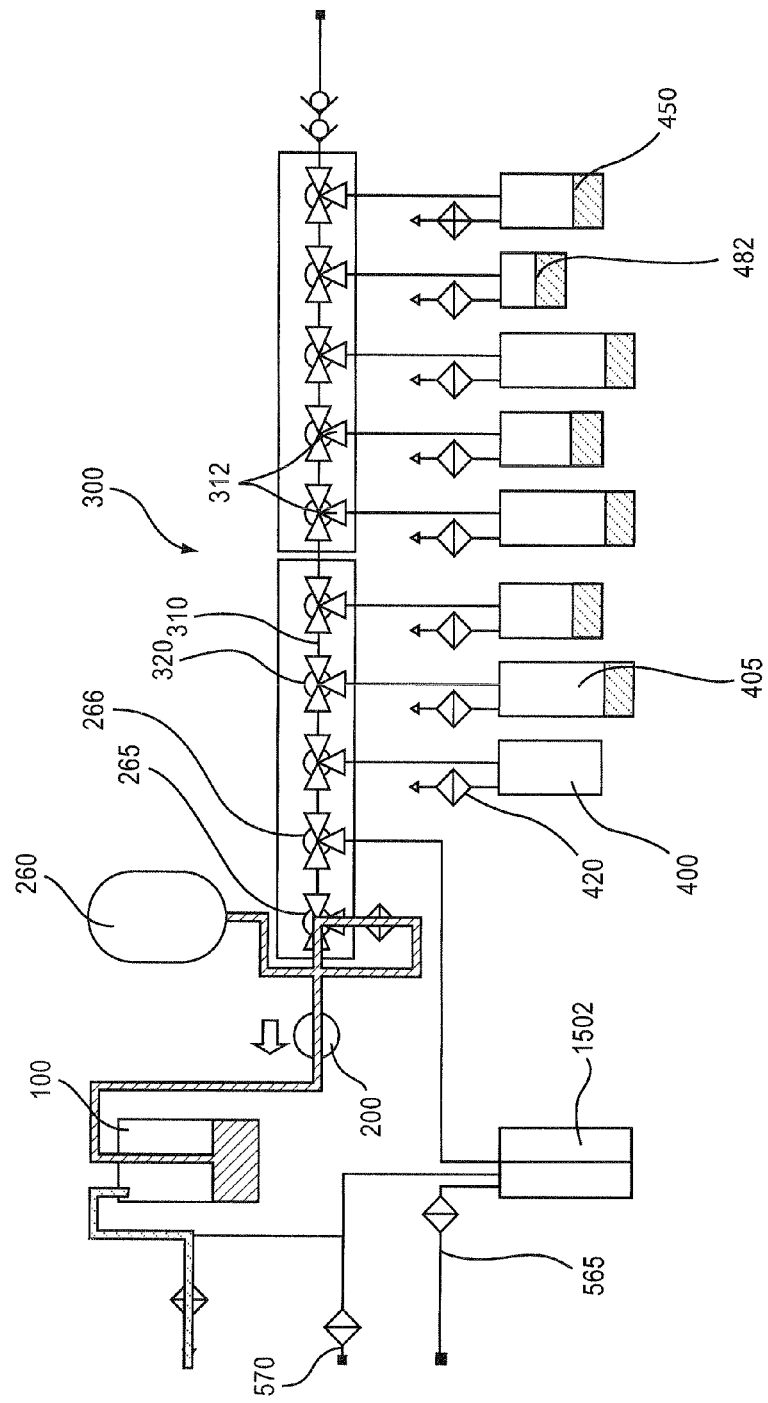
FIG. 61 is a schematic diagram to illustrate exemplary aspects of a closed vial fill system incorporating a CAV sensor and a method of using the closed vial fill system, in accordance with certain aspects of the present invention.
Figure 62:
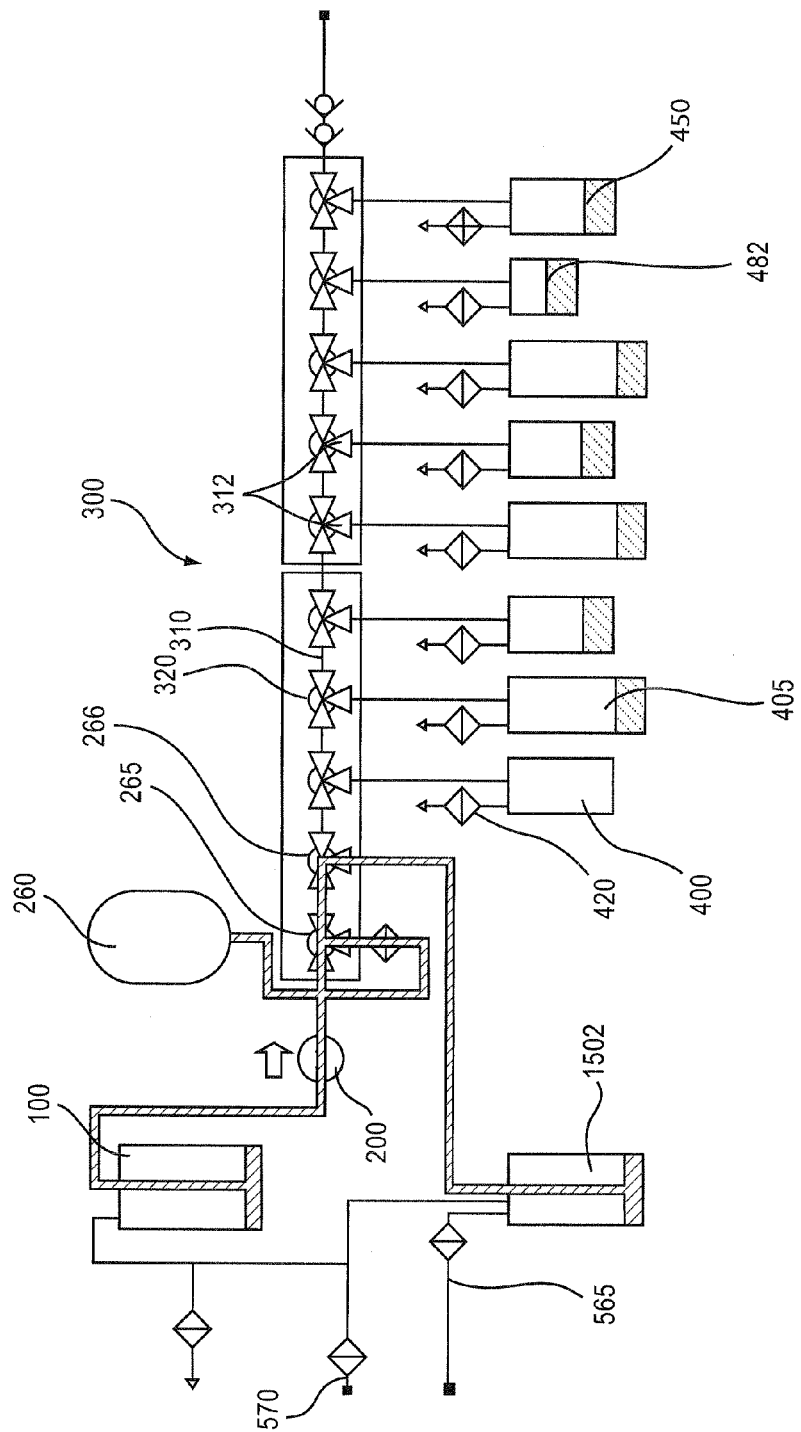
FIG. 62 is a schematic diagram to illustrate exemplary aspects of a closed vial fill system incorporating a CAV sensor and a method of using the closed vial fill system, in accordance with certain aspects of the present invention.

In accordance with yet another aspect of the present invention, as shown in FIGS. 61-65, the remaining dilution solution in the dilution container 260 may be used to perform another rinse of the disposable components. As shown in FIG. 61, the valve 265 may be opened and the peristaltic pump 200 operated to pull the remaining dilution solution from the dilution container 260 into the bulk product vial 100. Once the remaining dilution solution is in the bulk product vial 100, as shown in FIG. 62, the valve 265 may be closed to the dilution container 260, the valve 266 may be opened to allow fluid communication between the bulk product vial 100 and the CAV container 1502, and the peristaltic pump 200 may be operated in reverse to pull the dilution solution from the bulk product vial 100 and pump the dilution solution into the CAV container 1502.

Figure 63:
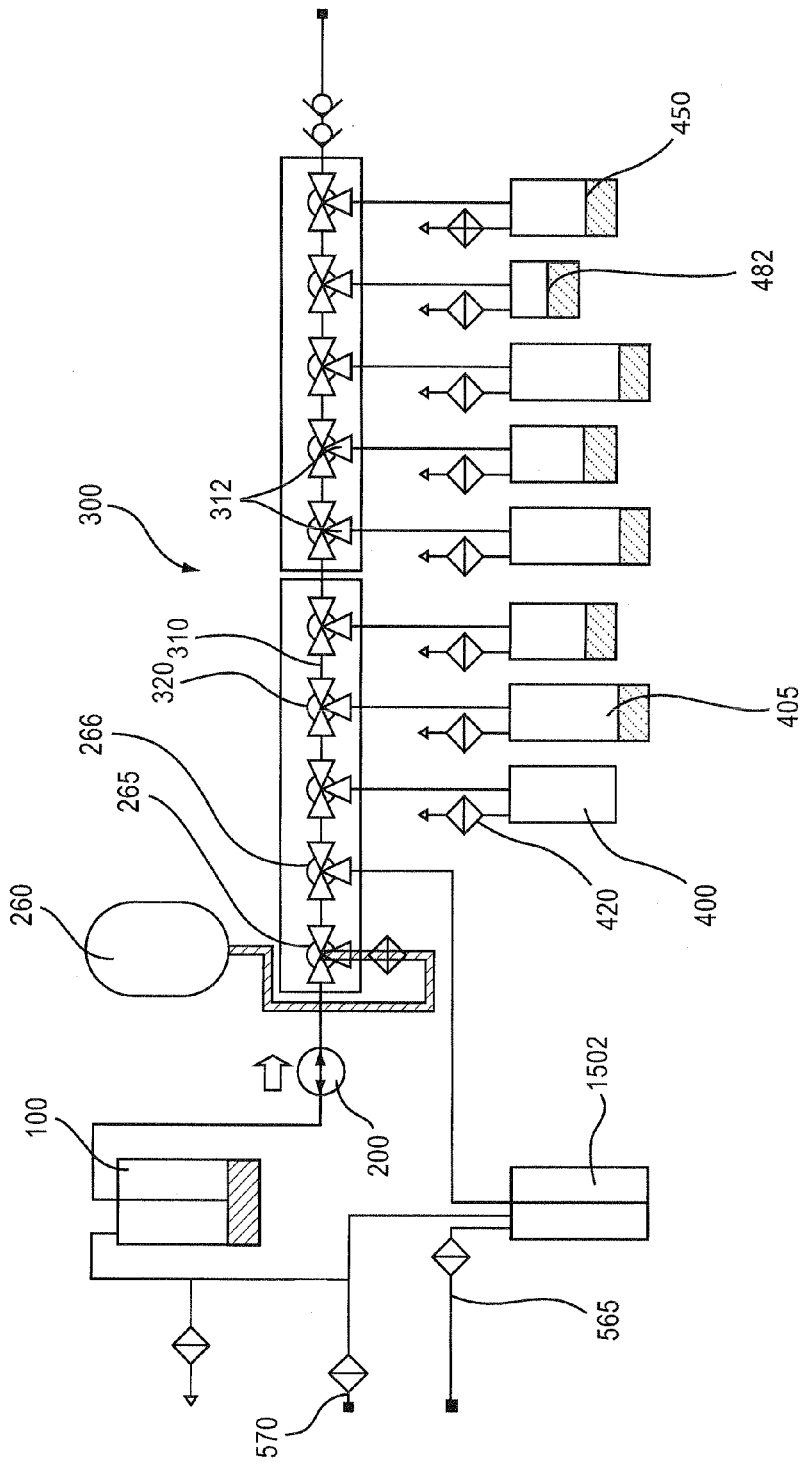
FIG. 63 is a schematic diagram to illustrate exemplary aspects of a closed vial fill system incorporating a CAV sensor and a method of using the closed vial fill system, in accordance with certain aspects of the present invention.
Figure 64:
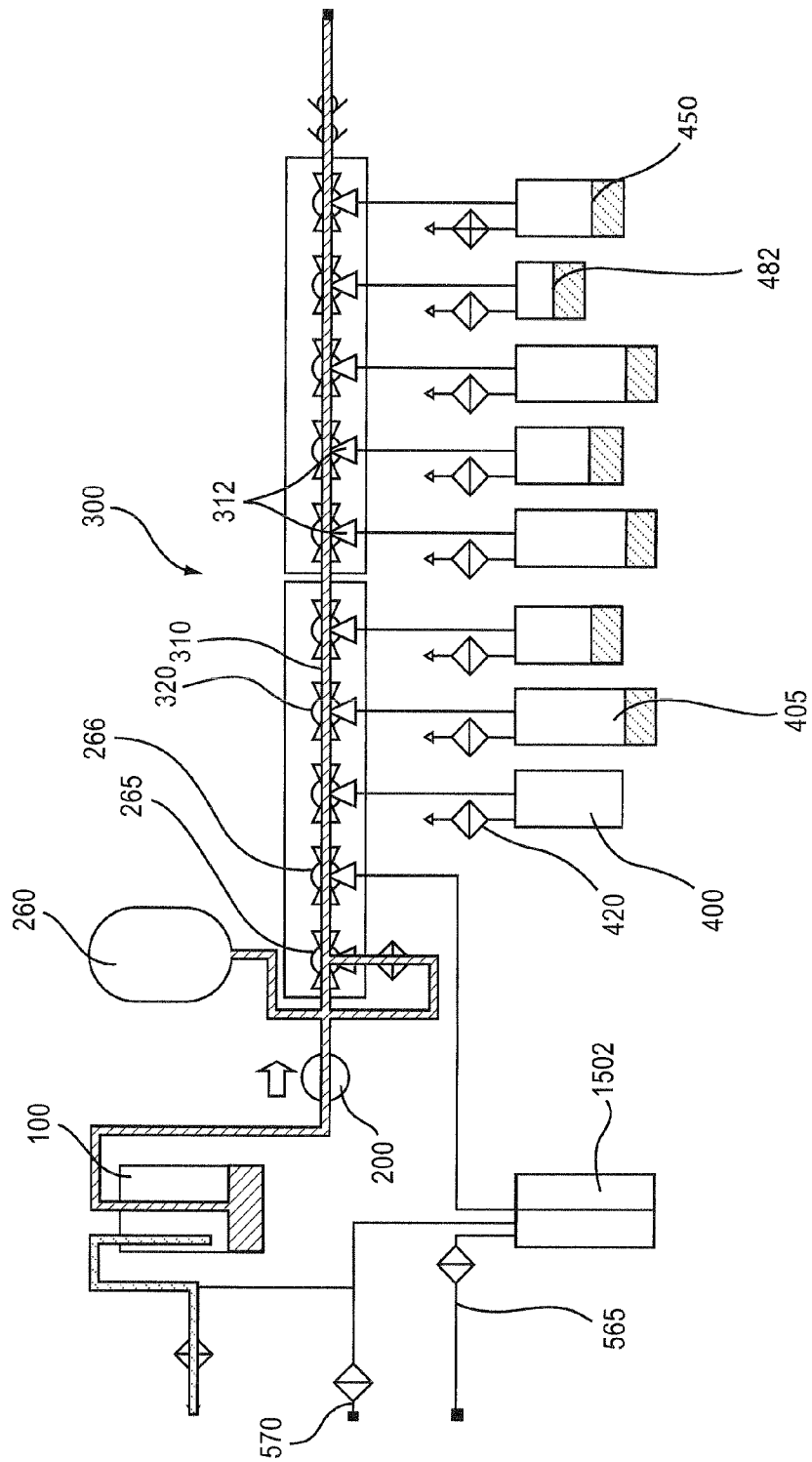
FIG. 64 is a schematic diagram to illustrate exemplary aspects of a closed vial fill system incorporating a CAV sensor and a method of using the closed vial fill system, in accordance with certain aspects of the present invention.

As shown in FIG. 63, once the dilution solution has been pumped into the CAV container 1502, the process may be reversed by reversing the direction of the pump 200 and the dilution solution transferred back to the bulk product vial 100 from the CAV container 1502. With the fluid path between the bulk product vial 100 and the CAV container 1502 thus rinsed, the valves 265 and 266 may be opened to allow fluid flow through the manifold tubes 310. As shown in FIG. 64, the dilution solution may then be pumped out of the bulk product vial 100 and through the manifold tubes 310 to the waste receptacle (not shown). As shown in FIG. 65, the peristaltic pump 200 may continue to operate in order to draw in atmospheric air, for example, through the vented bulk product vial 100 and pump the air through the system until all or substantially all of the dilution solution is forced from the manifold tubes 310 and into the waste receptacle (not shown).

As described previously, the vials may then be removed from the system 10 for transport in a shielded container to the appropriate location for testing and/or use in a procedure. The disposable components of the system 10 may be removed and discarded according to the proper protocol and the system prepared for another run.

The previous description is provided to enable any person skilled in the art to practice the various exemplary implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

The invention claimed is:
1. A closed path vial fill system, comprising:
a bulk product vial containing a bulk product;
a first tube element inserted into a peristaltic pump, wherein the first tube element is coupled with the bulk product vial;
a dispensing manifold assembly coupled with the first tube element;
at least one final product vial coupled to the dispensing manifold assembly;
a valve disposed between the peristaltic pump and the dispensing manifold assembly, the valve having a first position and a second position; and
a dilution container having a dilution solution, wherein the dilution container is coupled to the valve,
wherein in the first position, the valve allows fluid to flow from the dilution container to the bulk product vial, wherein in the second position, the valve allows fluid to flow from the bulk product vial to the dispensing manifold assembly, and wherein the peristaltic pump is configured to transfer a predetermined amount of bulk product from the bulk product vial to the at least one final product vial via the dispensing manifold assembly.

2. The system of claim 1, further comprising:
a stepper motor operably coupled with the peristaltic pump.

3. The system of claim 1, wherein the dilution solution comprises saline solution.

4. The system of claim 1, wherein the bulk product comprises a radiopharmaceutical.

5. The system of claim 4, wherein the radiopharmaceutical comprises one of fluorodeoxyglucose and fluoromisonidazole.

6. The system of claim 4, further comprising:
a radioactive shield surrounding the bulk product vial.

7. The system of claim 1, wherein the dispensing manifold assembly comprises a central manifold tube and a plurality of dispensing ports, and wherein each of the plurality of dispensing ports communicates with one of the at least one final product vial.

8. The system of claim 7,
wherein the dispensing manifold assembly comprises a plurality of valves,
wherein each valve corresponds with one of the plurality of dispensing ports; and
wherein each of the plurality of valves are configured to divert fluid flowing through the dispensing manifold assembly toward one of the plurality of dispensing ports.

9. The system of claim 1, further comprising:
an antimicrobial filter disposed upstream of the at least one final product vial.

10. The system of claim 9, further comprising:
a filter integrity system, the filter integrity system comprising:
a pressurized gas line disposed downstream of the antimicrobial filter; and
a diverter valve disposed downstream of the antimicrobial filter and coupled with the pressurized gas line,
wherein the diverter valve is configured to divert pressurized gas from the pressurized gas line toward the antimicrobial filter.

11. The system of claim 10, wherein the filter integrity system further comprises a pressure sensor configured to record a pressure on a downstream side of the antimicrobial filter.

12. The system of claim 10, wherein the filter integrity system further comprises a gas flow detector element disposed on an upstream side of the antimicrobial filter.

13. The system of claim 1, further comprising:
at least one vial cap coupled to the at least one final product vial,
wherein the at least one vial cap is configured to provide a sealed disconnect between the at least one final product vial and the dispensing manifold assembly.

14. The system of claim 1, further comprising:
a quality check station disposed on a downstream distal end of the dispensing manifold assembly configured to receive fluid flowing through the dispensing manifold assembly.

15. The system of claim 1, wherein one of the at least one final product vial contains a growth medium.

16. The system of claim 15, wherein the final product vial containing the growth medium is in fluid communication with a high performance liquid chromatography (HPLC) load loop.

17. The system of claim 1, further comprising:
a waste collection system coupled to a downstream distal end of the dispensing manifold assembly.

18. The system of claim 13,
wherein the at least one final product vial comprises an elastomeric septum and the at least one vial cap comprises a spike; and
wherein inserting the spike into the elastomeric septum establishes fluid communication between the at least one final product vial and the dispensing manifold assembly.

19. The system of claim 1, wherein the dispensing manifold assembly comprises a frame configured to support a plurality of rows of the least one final product vial.

20. The system of claim 19, further comprising a vial bracket attached to the frame and configured to mount the bulk product vial.

21. The system of claim 20, wherein the vial bracket comprises an orienting feature to seat the bulk vial product at an angle.

22. The system of claim 20, further comprising:
a precision scale coupled with the vial bracket.

23. The system of claim 1, further comprising:
a concentration, activity, and volume (CAV) container; and
a CAV sensor configured to detect radionuclide content in the CAV container,
wherein the CAV container is in fluid communication with the bulk product vial via a second tube element.

24. The system of claim 1, wherein the valve is disposed in-line between the peristaltic pump and the dispensing manifold assembly.

25. A sterilized kit, comprising:
one or more sterilized bulk product vials;
a sterilized dispensing manifold assembly;
a plurality of sterilized final product vials configured to receive a predetermined amount of bulk product from one of the one or more sterilized bulk product vials, wherein the plurality of sterilized final product vials are coupleable to the sterilized dispensing manifold assembly;
a sterilized tube element that couples the one or more sterilized bulk product vials to the sterilized dispensing manifold assembly, wherein the sterilized tube element is coupleable with a peristaltic pump; and
a sterilized dilution container comprising a dilution solution, wherein the dilution solution is capable of being transferred from the sterilized dilution container to the one or more sterilized bulk product vials through the sterilized tube element.

26. The sterilized kit of claim 25, further comprising:
a plurality of sterilized valves, wherein the plurality of sterilized valves are capable of diverting a flow of fluid within the sterilized dispensing manifold assembly.

27. The sterilized kit of claim 25, further comprising:
a sterilized antimicrobial filter, capable of being disposed upstream of the one or more sterilized final product vials.

28. The sterilized kit of claim 25, further comprising:
one or more sterilized ventilated caps coupleable to the one or more sterilized final product vials, wherein the one or more sterilized ventilated caps is configured to provide a sealed disconnect between the one or more sterilized final product vials and the sterilized dispensing manifold assembly.

29. The sterilized kit of claim 28, further comprising:
a sterilized packaging device capable of storing the one or more sterilized final product vials.

30. The sterilized kit of claim 29, wherein the sterilized packaging device comprises:
at least one base portion;
a vial containment portion coupled with each of the at least one base portion and sized to receive the one or more sterilized final product vials;
a cap retention portion coupled with a proximal end portion of each of the at least one base portion.

31. The sterilized kit of claim 30, wherein the at least one base portion comprises a plurality of base portions, and wherein each base portion of the plurality of base portions is connected to another base portion via a perforation.

32. The sterilized kit of claim 30, wherein the vial containment portion comprises a cylinder shape having an open distal end relative to the proximal end portion.

33. The sterilized kit of claim 30, wherein the vial containment portion has an inner diameter equal to or smaller than an outer diameter of the one or more sterilized final product vials providing a friction fit between the vial containment portion and the one or more sterilized final product vials.

34. The sterilized kit of claim 30, wherein the one or more ventilated caps comprise:
one or more cap retention devices; and
a spike capable of piercing a septum of the one or more sterilized final product vials.

35. The sterilized kit of claim 30, wherein the sterilized packaging device further comprises:
vial guides extending between the vial containment portion and the cap retention portion.

36. The sterilized kit of claim 30, wherein the sterilized packaging device further comprises:
a plurality of extension clips extending from a lower portion of the cap retention portion and configured to extend circumferentially around the spike.

37. The sterilized kit of claim 36, wherein a distal end of the plurality of extension clips form a circle having an inner diameter equal to or smaller than an outer diameter of the one or more sterilized final product vials to provide a friction fit between the one or more sterilized final product vials and the vial containment portion.

38. The sterilized kit of claim 31, wherein the sterilized packaging device further comprises:
at least one detent clip mateable with the one or more sterilized final product vials and configured to secure the one or more product vials in the vial containment portion.

39. The sterilized kit of claim 30, wherein the sterilized packaging device further comprises:
a tray comprising the at least one base portion,
wherein the vial containment portion comprises a first cavity formed in the tray, and
wherein the cap retention portion comprises a second cavity formed in the tray.

40. The sterilized kit of claim 39,
wherein the at least one base portion comprises a plurality of base portions, and
wherein the tray comprises the plurality of base portions.

41. The sterilized kit of claim 40, wherein the vial containment portion corresponding to a first base portion of the plurality of base portions has a different size than the vial containment portion corresponding to a second base portion of the plurality of base portions.

42. The sterilized kit of claim 40, wherein the sterilized packaging device further comprises:
one or more cap retention devices; and
a spike capable of piercing a septum of the one or more sterilized final product vials.

43. The sterilized kit of claim 42,
wherein the one or more cap retention devices comprises a plurality of fill cap retention arms and a transverse cap retention member, and
wherein the plurality of fill cap retention arms extend from distal ends of the transverse cap retention member.

44. The sterilized kit of claim 43, wherein the sterilized packaging device further comprises a lower slot extending away from a lower surface of the vial containment portion sized to receive a finger.

45. The sterilized kit of claim 43, wherein the plurality of fill cap retention arms comprises a securing mechanism mateable with the one or more sterilized final product vials.

46. The sterilized kit of claim 30, wherein the one or more sterilized final product vials is disposed in the vial containment portion.

47. The sterilized kit of claim 25, further comprising:
sterilized packaging enclosing the one or more sterilized bulk product vials, the sterilized dispensing manifold assembly, the sterilized tube element, the sterilized dilution container, and the one or more sterilized final product vials.

48. The sterilized kit of claim 47, wherein the sterilized packaging includes at least one mitt shaped to receive a hand.

49. A closed path vial fill system, comprising:
a bulk product vial containing a bulk product;
a first tube element inserted into a peristaltic pump, wherein the first tube element is coupled with the bulk product vial;
a dispensing manifold assembly coupled with the first tube element;
at least one final product vial coupled to the dispensing manifold assembly;
a valve disposed between the peristaltic pump and the dispensing manifold assembly, the valve having a first position and a second position; and
a dilution container having a dilution solution, wherein the dilution container is coupled to the valve,
wherein in the first position, the valve is closed to the dispensing manifold assembly and allows fluid to flow from the dilution container to the bulk product vial,
wherein in the second position, the valve is closed to the dilution container and allows fluid to flow from the bulk product vial to the dispensing manifold assembly, and
wherein the peristaltic pump is configured to transfer a predetermined amount of bulk product from the bulk product vial to the at least one final product vial via the dispensing manifold assembly.

* * * * *